United States Patent
Huang et al.

(10) Patent No.: US 11,376,242 B2
(45) Date of Patent: Jul. 5, 2022

(54) METHODS AND COMPOSITIONS FOR TREATING OBESITY AND/OR DIABETES AND FOR IDENTIFYING CANDIDATE TREATMENT AGENTS

(71) Applicant: The J. David Gladstone Institutes, a testamentary trust established under the Will of J. David Gladstone, San Francisco, CA (US)

(72) Inventors: Yadong Huang, San Francisco, CA (US); Qin Xu, Burlingame, CA (US); Robert W. Mahley, San Francisco, CA (US)

(73) Assignee: The J. David Gladstone Institutes, San Francisco, CA (US), a testamentary trust established under the Will of J. David Gladstone ( * ) Notice: Subject to any disclaimer, the term of this patent is extended or adjusted under 35 U.S.C. 154(b) by 0 days.

(21) Appl. No.: 16/129,296

(22) Filed: Sep. 12, 2018

(65) Prior Publication Data

US 2019/0000817 A1    Jan. 3, 2019

Related U.S. Application Data

(63) Continuation-in-part of application No. PCT/US2017/022584, filed on Mar. 15, 2017.
(Continued)

(51) Int. Cl.
*A61K 31/365* (2006.01)
*A61P 1/16* (2006.01)
(Continued)

(52) U.S. Cl.
CPC ........... *A61K 31/44* (2013.01); *A61K 9/0019* (2013.01); *A61K 31/365* (2013.01); *A61P 1/16* (2018.01);
(Continued)

(58) Field of Classification Search
CPC ........... G01N 2500/02; G01N 2500/04; G01N 2500/10; A61K 31/365
See application file for complete search history.

(56) References Cited

U.S. PATENT DOCUMENTS 8,008,468 B2    8/2011    Roelvink et al.
8,524,679 B2    9/2013    Pachuk
(Continued)

FOREIGN PATENT DOCUMENTS

CN    109414414 A    3/2019
EP    3429567 A1    1/2019
(Continued)

OTHER PUBLICATIONS

Lisanti et al, Cell Reports 2014, vol. 8, pp. 671-677. (Year: 2014).*
(Continued)

*Primary Examiner* — Craig D Ricci
*Assistant Examiner* — Janet L Coppins
(74) *Attorney, Agent, or Firm* — Schwegman Lundberg & Woessner, P.A.

(57) ABSTRACT

Provided are methods and compositions for identifying candidate agents for treatment of obesity, liver disease, and/or diabetes. Such methods include, e.g., contacting a mammalian cell or cell population with a test agent, and measuring an expression level and/or activity level of ClpP in the mammalian cell or in cells of the cell population. Also provided are methods and compositions for treating an individual (e.g., one who is obese and/or has diabetes). Treatment methods include administering an inhibitor of ClpP to the individual (e.g., to prevent or reduce weight gain, to increase insulin sensitivity, and/or to increase glucose tolerance).

11 Claims, 35 Drawing Sheets

Specification includes a Sequence Listing.

Related U.S. Application Data

(60) Provisional application No. 62/309,311, filed on Mar. 16, 2016.

(51) Int. Cl.
| | | |
|---|---|---|
| *A61P 3/04* | (2006.01) | |
| *A61K 31/44* | (2006.01) | |
| *C12Q 1/37* | (2006.01) | |
| *A61P 3/10* | (2006.01) | |
| *A61K 9/00* | (2006.01) | |
| *G01N 33/50* | (2006.01) | |
| *C12Q 1/686* | (2018.01) | |
| *G01N 33/68* | (2006.01) | |

(52) U.S. Cl.
CPC .............. *A61P 3/04* (2018.01); *A61P 3/10* (2018.01); *C12Q 1/37* (2013.01); *G01N 33/5067* (2013.01); *C12Q 1/686* (2013.01); *G01N 33/5091* (2013.01); *G01N 33/6848* (2013.01); *G01N 2500/10* (2013.01); *G01N 2800/042* (2013.01); *G01N 2800/044* (2013.01)

(56) References Cited

U.S. PATENT DOCUMENTS

| | | | |
|---|---|---|---|
| 2012/0129782 A1* | 5/2012 | Huang | A61P 9/00 514/17.8 |
| 2014/0163094 A1 | 6/2014 | Sieber et al. | |
| 2014/0243255 A1 | 8/2014 | Kandror et al. | |
| 2016/0221977 A1 | 8/2016 | Sello et al. | |

FOREIGN PATENT DOCUMENTS

| | | |
|---|---|---|
| JP | 2001509173 | 7/2001 |
| JP | 2012509888 | 4/2012 |
| JP | 2019515654 A | 6/2019 |
| WO | WO 2003031939 | 4/2003 |
| WO | WO 2010059942 | 5/2010 |
| WO | WO-2017161043 A1 | 9/2017 |

OTHER PUBLICATIONS

Hackl et al, JACS 2015, vol. 137, pp. 8475-8483. (Year: 2015).*
Anderson, Chemistry & Biology 2003, vol. 10, 787-797 (Year: 2003).*
Thiel, Nature Biotechnology vol. 22 No. 5 May 2004 (Year: 2004).*
Botticher Thomas, et al. (2012) "β-Lactams and β-lactones as activity-based probes in chemical biology" MedChemComm,vol. 3, No. 4; pp. 408-417.
Larkin and Byrd (2015) "Antagonizing ClpP: A New Power Play in Targeted Therapy for AML"; Cancer Cell. 27(6); pp. 747-749.
Kyriakos et al. (2009) "Mechanisms of obesity and related pathologies: role of apolipoprotein E in the development of obesity"; FEBS Journal, vol. 276, No. 20; pp. 5720-5728.
Al-Furoukh et al. (2014) "NOA1, a novel ClpXP substrate, takes an unexpected nuclear detour prior to mitochondrial import"; PLoS ONE 9(7): e103141.
Baker et al., (2012) "ClpXP, an ATP-powered unfolding and protein-degradation machine"; *Biochim Biophys Acta*.1823(1); pp. 15-28.
Burton et al., (2003) "Energy-dependent degradation: Linkage between ClpX-catalyzed nucleotide hydrolysis and protein-substrate processing"; Protein Sci.12(5); pp. 893-902.
Cole et al. "Inhibition of the mitochondrial protease, ClpP, as a therapeutic strategy for human acute myeloid leuekmia," Cancer Cell, Jun. 8, 2015 (Jun. 8, 2015), vol. 27, Iss. 6, pp. 864-876.
Hackl et al. (2015). "Phenyl Esters Are Potent Inhibitors of Caseinolytic Protease P and Reveal a Stereogenic Switch for Deoligomerization"; J. Am. Chem. Soc., 137; pp. 8475-8483.

Joshi et al. (2004) "Communication between ClpX and ClpP during substrate processing and degradation"; *Nat Struct Mol Biol*.11(5): pp. 404-411.
Kang et al. (2005) "Human mitochondrial ClpP is a stable heptamer that assembles into a tetradecamer in the presence of ClpX"; *J Biol Chem*. 280(42): pp. 35424-35432.
Kobayashi et al. (2000) "The db/db mouse, a model for diabetic dyslipidemia: molecular characterization and effects of Western diet feeding"; Metabolism. 49(1): pp. 22-31.
Lee et al. " ApoE Polymorphism May Determine Low-Density Lipoprotein Cholesterol Level in Association with Obesity and Metabolic Syndrome in Postmenopausal Korean Women," Yonsei Med J, Apr. 6, 2011 (Apr. 6, 2011), vol. 52, No. 3, pp. 429-434, entire document.
Rath et al. "Induction of dsRNA-activated protein kinase links mitochondrial unfolded protein response to the pathogenesis of intestinal inflammation," Gut, Oct. 13, 2011 (Oct. 13, 2011), vol. 61, Iss. 9, pp. 1269-1278.
"European Application Serial No. 17767473.6, Response filed Jun. 15, 2020 to Extended European Search Report dated Nov. 13, 2019", 12 pgs.
"European Application Serial No. 17767473.6, Response to Communication pursuant to Rules 161(1) and 162 EPC filed May 1, 2019", 9 pgs.
"International Application Serial No. PCT/US2017/022584, International Preliminary Report on Patentability dated Sep. 27, 2018", 8 pgs.
"International Application Serial No. PCT/US2017/022584, International Search Report dated Jun. 5, 2017", 4 pgs.
"International Application Serial No. PCT/US2017/022584, Written Opinion dated Jun. 5, 2017", 6 pgs.
"Japanese Application Serial No. 2018-548758, Preliminary Amendment filed Mar. 12, 2020", w/English Claims, 5 pgs.
"Chinese Application Serial No. 201780024269.5, Office Action dated Jul. 22, 2021", With English translation, 11 pages.
"Chinese Application Serial No. 201780024269.5, Response filed Oct. 8, 2021 to Office Action dated Jul. 22, 2021", With English translation, 19 pages.
"Japanese Application Serial No. 2018-548758, Examiners Decision of Final Refusal dated Oct. 12, 2021", With English translation, 6 pages.
"Chinese Application Serial No. 201780024269.5, Decision of Rejection dated Oct. 26, 2021", With English translation, 9 pgs.
"European Application Serial No. 17767473.6, Response filed Oct. 26, 2021 to Communication Pursuant to Article 94(3) EPC dated Apr. 26, 2021", 96 pgs.
"Japanese Application Serial No. 2018-548758, Response filed Jun. 14, 2021 to Notification of Reasons for Refusal dated Mar. 16, 2021", w/o English claims.
"Chinese Application Serial No. 201780024269.5, Office Action dated Oct. 26, 2020", w English translation, 15 pgs.
"Chinese Application Serial No. 201780024269.5, Response filed Mar. 10, 2021 to Office Action dated Oct. 26, 2020", w English claims, 10 pgs.
"Japanese Application Serial No. 2018-548758, Notification of Reasons for Refusal dated Mar. 16, 2021", w English Translation, 8 pgs.
Med. Chem. Commun, vol. 3, No. 4, (2012), 408-417.
"European Application Serial No. 17767473.6, Communication Pursuant to Article 94(3) EPC dated Apr. 26, 2021", 8 pgs.
Cole, Alicia, "Inhibition of the mitochondrial protease, CipP, as a therapeutic strategy for human acute myeloid leuekmia", Cancer Cell, vol. 27, No. 6, (2015), 864-876.
"European Application Serial No. 17767473.6, Extended European Search Report dated Nov. 13, 2019", 7 pgs.
Kyriakos, E Kypreos, "Mechanisms of obesity and related pathologies: Role of apolipoprotein E in the development of obesity: ApoE and obesity", FEBS Journal, vol. 276, No. 20,, (Sep. 15, 2009), 18 pgs.
Larkin, Karilyn, "Antagonizing ClpP: A New Power Play in Targeted Therapy for AML", Cancer Cell, Cell Press, US, vol. 27, No. 6, (Jun. 8, 2015), 747-749.

(56) References Cited

OTHER PUBLICATIONS

Thomas, Bottcher, "[beta]-Lactams and [beta]-lactones as activity-based probes in chemical biology", MEDCHEMCOMM, vol. 3, No. 4, (Jan. 1, 2012), 10 pgs.
"Chinese Application Serial No. 201780024269.5, Response filed Feb. 10, 2022 to Decision of Rejection dated Oct. 26, 2021", With English machine translation, 11 pgs.
"Japanese Application Serial No. 2018-548758, Examiners Decision of Final Refusal dated Oct. 12, 2021", With English machine translation, 22 pgs.

\* cited by examiner

Fig. 17
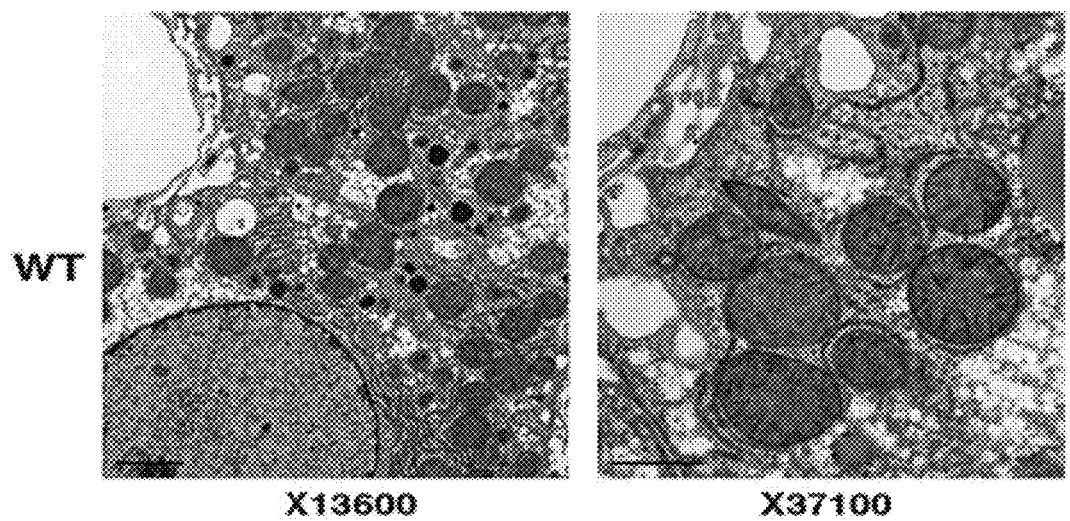
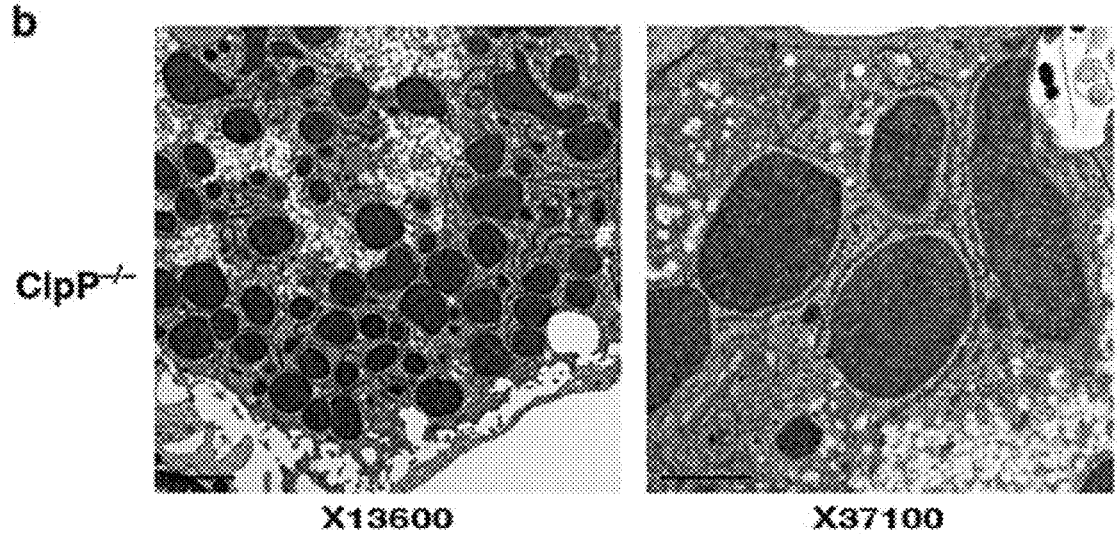
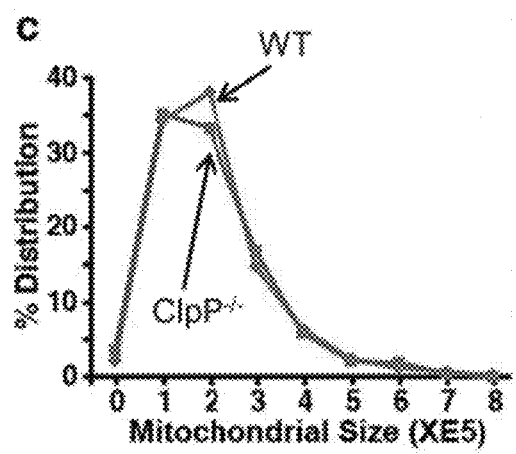
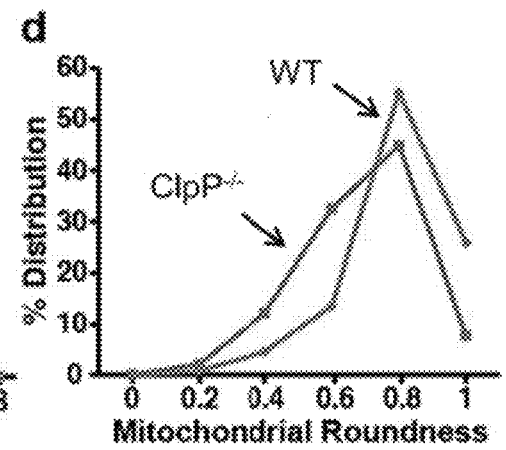

Fig. 20

| Tissue | Change in ClpP-KO tissue compared to WT | Top Rank ID |
|---|---|---|
| Hippocamus | Increase | Ornithine aminotransferase, mitochondrial |
| | | Heat shock protein 75KD, mitochondrial |
| | | Glycerol-3-phosphate dehydrogenase, mitochondrial |
| | | Stress-70 protein, mitochondrial |
| | | V-type proton ATPase catalytic subunit A |
| | | Heat shock protein HSP90 |
| | | Leucine-rich PPR motif-containing protein, mitochondrial |
| | | Tripeptidyl-peptidase 2 |
| | | Lysyl-tRNA synthetase |
| | | 2-oxoisovalerate dehydrogenase subunit alpha |
| | | Glyoxalase domain-containing protein 4 |
| | | Tubulin alpha-1B chain |
| | | Succinate dehydrogenase [ubiquinone] flavoprotein, mitochondrial |
| | | Histone H4 |
| | | Dynein light chain roadblock-type 1 |
| | | Cytochrome b-c1 complex subunit 1, mitochondrial |
| | | Creatine kinase B-type |
| | Decrease | Endoplasmic reticulum resident protein 29 |
| | | NADH dehydrogenase [ubiquinone] 1 alpha |
| | | Cytochrome c1, heme protein, mitochondrial |
| | | NmrA-like family domain-containing protein 1 |
| | | Calcineurin subunit B type 1 |
| | | Glutathione S-transferase P |
| | | Proteasome subunit beta type-1 |

Fig. 20 (Cont.)

| | | |
|---|---|---|
| Liver | Increase | Glutathione S-transferase A4 |
| | | Glutathione S-transferase P 1 |
| | | Glutathione S-transferase P 2 |
| | | Aldehyde dehydrogenase, mitochondrial |
| | | Peroxiredoxin-1 |
| | | Peroxiredoxin-4 |
| | | Stress-70 protein, mitochondrial |
| | | Heat shock protein 75 kDa, mitochondrial |
| | | 5-oxoprolinase |
| | | Carbamoyl-phosphate synthase, mitochondria |
| | | Proteasome subunit beta type-2 |
| | | Ornithine aminotransferase, mitochondria |
| | | Leucine-rich PPR motif-containing protein, mitochondria |
| | | Phenylalanine-4-hydroxylase |
| | | Protein SERAC1 |
| | Decrease | Cytochrome b5 type B |
| | | Myosin regulatory light chain 12B |
| | | Fatty acid-binding protein, intestinal |
| | | Thyroid hormone-inducible hepatic protein |
| | | Major urinary protein 2 |
| | | Major urinary proteins 11 and 8 |
| | | Fatty acid-binding protein, liver |
| | | Carbonic anhydrase 3 |
| | | Non-specific lipid-transfer protein |
| | | ATP-citrate synthase |
| | | Dihydropyrimidine dehydrogenase [NADP+] |
| Muscle | Increase | Peroxiredoxin-5, mitochondrial |
| | | Ornithine aminotransferase, mitochondrial |
| | | Protein SERAC1 |
| | | Myosin-binding protein H |
| | | Regulator of telomere elongation helicase 1 |
| | | Ataxin-7 |
| | | Stress-70 protein, mitochondrial |
| | | Myosin-4 |
| | Decrease | Myoglobin |
| | | NADH dehydrogenase [ubiquinone] 1 alpha subcomplex subunit 8 |
| | | Hemoglobin subunit beta-1 |
| | | Histone H4 |
| | | actin |
| | | NADH dehydrogenase [ubiquinone] iron-sulfur protein, mitochondrial |
| | | Lactoylglutathione lyase |
| | | NADH dehydrogenase [ubiquinone] 1 alpha subcomplex subunit 10 |
| | | NADH-ubiquinone oxidoreductase 75 kDa subunit, mitochondrial |

Fig. 21

| ClpX | Caseinolytic Peptidase X Homolog |
|---|---|
| Trap1 | Heat shock protein 75 KD (mitochondria) |
| Grp75 | Stress 70 protein (mitochondria) |
| LRPPRC | Leu rich PPR contain protein (mitochondria) |
| OAT | Ornithine aminotransferase (mitochondria) |
| LonP1 | Lon Peptidase 1 (mitochondria) |

Fig. 22

|  | Hippocampus | | Liver | | Muscle | | adipose | |
|---|---|---|---|---|---|---|---|---|
|  | Fold change (KO vs WT) | FDR | Fold change (KO vs WT) | FDR | Fold change (KO vs WT) | FDR | Fold change (KO vs WT) | FDR |
| ClpX | 0.973 | 1.000 | 1.880 | 0.207 | 0.887 | 1.000 | 0.898 | 1.000 |
| Trap1 | 0.835 | 0.973 | 1.020 | 1.000 | 1.070 | 1.000 | 0.760 | 0.844 |
| Grp75 | 1.140 | 1.000 | 1.030 | 1.000 | 1.220 | 0.997 | 0.841 | 1.000 |
| LRPPRC | 1.090 | 1.000 | 0.942 | 1.000 | 0.940 | 1.000 | 0.857 | 1.000 |
| OAT | 0.982 | 1.000 | 0.613 | 0.525 | 1.080 | 1.000 | 0.740 | 0.885 |
| LONP1 | 0.883 | 0.999 | 0.975 | 1.000 | 1.050 | 1.000 | 0.734 | 0.656 | mRNA Levels of ClpP Substrates Remain Unchanged After A2-32-01 Treatment

A2-32-01 in vivo Study Design

A2-32-01 Treatment Significantly Improves Insulin Sensitivity as Measured by Glucose Tolerance in Mice on High Fat Diet

US 11,376,242 B2

METHODS AND COMPOSITIONS FOR TREATING OBESITY AND/OR DIABETES AND FOR IDENTIFYING CANDIDATE TREATMENT AGENTS

CROSS-REFERENCE

This application is a continuation-in-part of International Application No. PCT/US2017/022584, filed Mar. 15, 2017, which application claims the benefit of U.S. Provisional Patent Application No. 62/309,311, filed Mar. 16, 2016, which applications are incorporated herein by reference in their entireties.

INCORPORATION BY REFERENCE OF SEQUENCE LISTING PROVIDED AS A TEXT FILE

A Sequence Listing is provided herewith as a text file, "GLAD-408WO_SEQUENCE_LISTING_ST25.txt" created on Mar. 13, 2017 and having a size of 9 KB. The contents of the text file are incorporated by reference herein in their entirety.

INTRODUCTION

Mammalian ClpXP is a mitochondrial matrix protease complex that requires ATP to unfold and hydrolyze protein substrates. The ClpXP complex includes a catalytic subunit (ClpP) and a regulatory subunit (ClpX). The *Escherichia coli* ClpP homolog forms a barrel-shaped complex with hydrolytic active sites sequestered inside, while the *Escherichia coli* ClpX homolog forms a hexamer ring that attaches to each end of the barrel and is responsible for substrate recognition and unfolding. Prokaryotic ClpXP protease facilitates the degradation of damaged or unneeded polypeptides for protein quality control. Like *E. coli* ClpP, human ClpP also forms a chamber-like structure in the presence of ClpX. The physiological functions of ClpP in mitochondria, the prime energy generators of mammalian cells that play critical roles in energy homeostasis and metabolic regulation, are largely unknown.

There is a need in the art for methods and compositions for identifying candidate agents for treating diseases related to energy homeostasis and metabolic regulation, such as obesity, liver disease, and/or diabetes. For example, there is a need in the art for methods and compositions for identifying candidate agents for increasing insulin sensitivity, preventing and/or reducing weight gain, preventing and/or reducing fat tissue, e.g., white adipose tissue, and the like. There is also a need in the art for methods and compositions for treating obesity, liver disease, and/or diabetes (e.g., by increasing insulin sensitivity, preventing and/or reducing weight gain, preventing and/or reducing fat tissue, e.g., white adipose tissue, and the like).

SUMMARY

Provided are methods and compositions for identifying candidate agents for treating obesity, liver disease, and/or diabetes (e.g., candidate agents for decreasing an amount of fat tissue in an individual, preventing or reducing weight gain of an individual, increasing insulin sensitivity of an individual, and/or increasing glucose tolerance of an individual). In some embodiments of the present disclosure, such methods include (a) contacting a mammalian cell or cell population (e.g., a rodent cell, a mouse cell, a rat cell, a non-human primate cell, a monkey cell, a human cell, or a cell population thereof) with a test agent, and (b) measuring an expression level (e.g., protein and/or mRNA) and/or activity level of ClpP in the mammalian cell (the agent-contacted cell) or in cells of the agent-contacted cell population. It is then determined whether the test agent caused a reduction of ClpP expression and/or activity. Those test agents that reduce ClpP expression (e.g., protein and/or mRNA) and/or activity, can be identified as candidate agents for treatment. Thus, a compound is considered to be a "test agent" prior to contact with a cell or cell population (e.g., in vitro, ex vivo, or in vivo), and if the compound (the test agent) reduces ClpP expression (e.g., as can be shown by measuring levels of ClpP protein and/or ClpP-encoding mRNA) and/or activity, it is then considered to be a "candidate agent" (e.g., a candidate agent for treatment, such as for treating obesity, liver disease and/or diabetes). Thus, in some cases a subject method further includes a step (c): determining whether the test agent caused a reduction of ClpP expression (e.g., where a reduction of ClpP expression is indicative that the test agent is a candidate agent for treatment) and/or activity. In some cases, a subject method includes either: (step c) determining that the test agent caused a decrease in the expression level and/or activity level of ClpP (e.g., relative to a reference value, e.g., an expression level and/or activity level of ClpP prior to contact with the test agent, an expression level and/or activity level of ClpP after contact with a control agent that is known not to reduce ClpP expression, and the like), and identifying the test agent as a candidate agent for treating obesity, liver disease, and/or diabetes, or (step d) determining that the test agent did not cause a decrease in the expression level and/or activity level of ClpP (e.g., relative to the reference value).

In some cases, the test agent is a small molecule or a polypeptide. In some cases, the expression level (of ClpP) is an RNA expression level and the measuring includes, e.g., the use of quantitative RT-PCR, a microarray, or RNA sequencing. In some cases, the expression level (of ClpP) is a protein expression level and the measuring includes detecting ClpP protein (e.g., using an anti-ClpP antibody, mass spectrometry, and/or an enzyme-linked immunosorbent assay (ELISA) assay). In some cases, the method includes screening a plurality of test agents to identify one or more candidate agents for treating obesity, liver disease, and/or diabetes.

In some cases, the mammalian cell (the target cell to be contacted with the test agent) is a liver cell (a hepatocyte). In some cases, the contacting is in vitro (e.g., the mammalian cell is in vitro). In some cases, the contacting is ex vivo (e.g., the mammalian cell is ex vivo). In some cases, the contacting is in vivo (e.g., the mammalian cell is in vivo). In some cases, the contacting includes administering the test agent to a mouse. In some cases, the method includes a step of measuring an expression level and/or activity level of ClpP in the mouse prior to the contacting of step (a) in order to obtain the reference value. In some cases, the method includes a step of generating a report that the test agent is a candidate agent for treating obesity, liver disease, and/or diabetes.

In some cases, a subject method includes, after determining that the test agent is a candidate agent for treatment, a step of administering the identified candidate agent to an individual that has obesity, liver disease, and/or diabetes (e.g., as a treatment, or as a way to test whether the candidate agent causes a desired outcome). In some cases, the individual is a mouse, a non-human primate, or a human. In some cases, the method includes, after administering the identified candidate agent to the individual, measuring one or more features of the individual selected from: insulin sensitivity; blood glucose level; glucose tolerance; body fat mass; an amount of fat tissue; an amount of white adipose tissue; percent fat mass; body weight; visceral adipose adipocyte size; plasma leptin level; growth hormone level; basal energy expenditure; a level of phosphorylated AKT (p-AKT) in muscles and/or fibroblasts; percent lean mass; mitochondrial number in hepatocytes; mitochondrial mass in hepatocytes; mitochondrial morphology in hepatocytes; fibroblast respiratory capacity; fibroblast maximal oxygen consumption rate (OCR); and fibroblast resistance to $H_2O_2$-induced cytotoxicity.

Also provided are methods and compositions for treating an individual (e.g., one who is obese and/or has diabetes or who has been diagnosed as being obese and/or having diabetes). Treatment methods include administering an inhibitor of ClpP (e.g., an agent that reduces the amount and/or activity of ClpP protein) to the individual in an amount effective for decreasing an amount of fat tissue in the individual, preventing or reducing weight gain of the individual, increasing insulin sensitivity of the individual, and/or increasing glucose tolerance of the individual. In some cases, the inhibitor of ClpP is a small molecule, e.g., any small molecule ClpP inhibitor described herein, e.g., a β-Lactone, such as any β-Lactone molecule described herein. In some cases, the small molecule is (3RS,4RS)-3-(non-8-en-1-yl)-4-(2-(pyridin-3-yl)ethyl)oxetan-2-one. In some cases, the inhibitor of ClpP is an RNAi agent or a gene editing agent that targets ClpP (e.g., specifically reduces the expression level of the ClpP protein). In some cases, the inhibitor of ClpP is administered such that reduction of ClpP expression is substantially liver-specific, and the amount administered is effective for increasing insulin sensitivity of the individual. In some cases, the inhibitor of ClpP is delivered directly to the individual's liver, and the amount administered is effective for increasing insulin sensitivity of the individual. In some cases, the administering includes local injection. In some cases, a subject treatment method includes a step of measuring insulin sensitivity of the individual.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 (panel a) provides images showing that ClpP$^{-/-}$ mice were smaller and had lower body fat. FIG. 1 (panel b) provides graphs showing that body weights of ClpP$^{-/-}$ mice were lower than those of wild-type (WT) and ClpP$^{+/-}$ littermates (n=9 for WT female, n=10 for ClpP$^{+/-}$ female, n=13 for ClpP$^{-/-}$ female, n=13 for WT male, n=13 for ClpP$^{+/-}$ male, n=10 for ClpP$^{-/-}$ male). FIG. 1 (panel c) provides a graph showing that new-born ClpP$^{-/-}$ pups (postnatal day 1) had similar body weights to WT and ClpP$^{+/-}$ pups (n=5 for WT, n=7 for ClpP$^{+/-}$, n=6 for ClpP$^{-/-}$). FIG. 1 (panel d), FIG. 1 (panel e) provide graphs depicting the fat mass and fat content of 5-month-old male mice (n=7). FIG. 1 (panel f), FIG. 1 (panel g) provide graphs depicting lean mass and lean content of 5-month-old male mice (n=7). FIG. 1 (panel h), FIG. 1 (panel i) provide data depicting brown adipose tissue mass and content of 8-month-old male mice (n=7 for WT and ClpP$^{+/-}$, n=4 for ClpP$^{-/-}$). FIG. 1 (panel j) provides a graph depicting body weight gain of 8-month-old male mice on a high-fat diet (HFD) (n=8 for WT and ClpP$^{+/-}$, n=7 for ClpP$^{-/-}$). FIG. 1 (panel k), FIG. 1 (panel l) provide graphs of fat mass and content of 8-month-old male mice after 40 days on HFD (n=8 for WT, n=7 for ClpP$^{+/-}$ and ClpP$^{-/-}$). FIG. 1 (panel m) provides a histogram of adipocyte size distribution of WT, ClpP$^{+/-}$, and ClpP$^{-/-}$ mice. Data are mean±SD. *P<0.05, P<0.01, *P<0.005 versus WT.

FIG. 2 (panel a), FIG. 2 (panel b) provide graphs depicting food intake of 7-8-month-old male mice (n=12 for WT and ClpP$^{-/-}$, n=15 for ClpP$^{+/-}$). FIG. 2 (panel c) provides a timeline of fasting-refeeding experiments. FIG. 2 (panel d), FIG. 2 (panel e) provide graphs depicting body weight loss of 7-8-month-old male mice after a 24-h fast (n=14 for WT and ClpP$^{-/-}$, n=15 for ClpP$^{+/-}$). FIG. 2 (panel f) provides graphs depicting food intake of 7-8month-old male mice during 0-8 hour or 8-24 hour refeeding periods (n=3 for WT and ClpP$^{-/-}$, n=4 for ClpP$^{+/-}$). FIG. 2 (panel g) provides graphs depicting the percentage body weight gain of 7-8-month-old male mice after 8 hour or 24 hour refeeding (n=14 for WT and ClpP$^{-/-}$, n=15 for ClpP$^{+/-}$). FIG. 2 (panel h), FIG. 2 (panel i) provide graphs depicting body temperature of 8-month-old male mice after a 16-h fast or during free feeding (n=13 for WT and ClpP$^{+/-}$, n=14 for ClpP$^{-/-}$). Data are mean±SD. *P<0.05, P<0.01, *P<0.005 versus WT.

FIG. 3 (panels a-c) provide graphs depicting blood glucose and plasma insulin levels of 8-month-old male mice on chow diet (n=8 for each group). FIG. 3 (panel d), FIG. 3 (panel e) provide graphs depicting blood glucose and plasma insulin levels of 8-month-old male mice on a high-fat diet (n=5 for each group). FIG. 3 (panel f) provides a graph depicting glucose tolerance curve of 6-10-month-old male mice (n=9 for each group). FIG. 3 (panel g) provides graphs depicting plasma insulin levels of 6-10-month-old male mice after glucose challenge (n=5 for each group). FIG. 3 (panel h) provides a graph depicting an insulin tolerance curve of 12-month-old male mice (n=7 for each group). FIG. 3 (panel i) provides a graph depicting a pyruvate tolerance curve of 14-month-old male mice (n=5 for WT and ClpP$^{-/-}$, n=7 for ClpP$^{+/-}$). FIG. 3 (panel j), FIG. 3 (panel k) provide a representative image (j) and quantification (k) of pAKT immunoblot of mouse fibroblasts from WT, ClpP$^{+/-}$, or ClpP$^{-/-}$ mice. FIG. 3 (panel l) provides a graph depicting pAKT levels in gastrocnemius muscles of 10-month-old male mice (n=3 for each group). FIG. 3 (panel m) provides a graph depicting pAKT levels in mouse fibroblasts after IGF treatment (n=6 per dose for each group). FIG. 3 (panel n) provides a graph depicting blood glucose levels of 3-7-month-old db/db mice with different ClpP genotypes after a 4-h fast (n=8 for WT, n=7 for ClpP$^{+/-}$, n=6 for ClpP$^{-/-}$). FIG. 3 (panel o) provides a glucose tolerance curve of 3-7-month-old db/db mice with different ClpP genotypes (n=8 for WT, n=7 for ClpP$^{+/-}$, n=6 for ClpP$^{-/-}$). Data are mean±SD. *P<0.05, P<0.01, *P<0.005 versus WT.

FIG. 4 (panels a-h) provide representative western blots and quantification of TRAP1, Grp75, LRPPRC, and ClpX in lysates from various organs of mice (n=3 for each group). FIG. 4 (panel i), FIG. 4 (panel j) provide representative western blots (i) and quantification (j) of ClpX, TRAP1, LRPPRC, and OAT in lysates of WT or ClpP$^{-/-}$ mouse fibroblasts. FIG. 4 (panel k), FIG. 4 (panel l) provide representative western blots (k) and quantification (l) of ClpX, TRAP1, LRPPRC, and OAT in ClpP$^{-/-}$ fibroblasts transfected with an empty vector (control) or a mouse ClpP cDNA construct. Data are mean±SD. *P<0.05, P<0.01, *P<0.005 versus WT.

FIG. 5 (panel a) provides representative electron microscopic image of mitochondria in WT and ClpP$^{-/-}$ mouse hepatocytes. Scale bars are 2 μm. FIG. 5 (panel b), FIG. 5 (panel c) provide graphs of mitochondrial number (b) and mass (c, measured by mitochondrial area) increased in ClpP$^{-/-}$ mouse hepatocytes. The mitochondrial numbers were counted for each random field at ×13,600 magnification (n=17 for WT, n=12 for ClpP$^{-/-}$). The total mitochondrial area per field was measured by Image J at ×13,600 magnification (n=17 for WT, n=12 for ClpP$^{-/-}$). FIG. 5 (panel d) provides an oxygen consumption rate (OCR) curve of fibroblasts from ClpP$^{-/-}$ and WT mice under basal and uncoupling conditions (n=12 for each group). FIG. 5 (panel e) provides a graph showing that fibroblasts from ClpP$^{-/-}$ mice were resistant to $H_2O_2$-induced cell death compared with fibroblasts from WT mice (n=8 for each group). FIG. 5 (panel f) provides a graph showing that overexpression of mouse ClpP decreased the respiratory capacity of ClpP$^{-/-}$ fibroblasts (n=12 for each group). FIG. 5 (panel g) provides a graph showing that overexpression of mouse ClpP abolished the $H_2O_2$ resistance of ClpP$^{-/-}$ fibroblasts (n=8 for each group). FIG. 5 (panel h), FIG. 5 (panel i) provide graphs showing that lentiviral shRNA-mediated knockdown of TRAP1 or Grp75 lowered the resistance of ClpP$^{-/-}$ fibroblasts to $H_2O_2$ cytotoxicity (n=8 for each group). FIG. 5 (panel j) provides a graph showing the effects of lentiviral shRNA-mediated knockdown of different mitochondrial proteins on the maximum respiration capacity of ClpP$^{-/-}$ fibroblasts (n=9 for each group). Data are mean±SD. *P<0.01, P<0.01, *P<0.005 versus WT (b-e) or ClpP$^{-/-}$ (f-j).

FIG. 6 (panel a) provides images of ClpP immunostaining, showing a significant reduction of ClpP in livers of AAV-Cre-injected ClpP-cKO mice compared to control AAV-injected mice. Scale bars are 50 μm. FIG. 6 (panels b-d) provide graphs of body weights (b and c) of ClpP-cKO mice before and 3 weeks after AAV injection. The body weight gain of the AAV-Cre-injected mice was significant lower than that of control AAV-injected mice (d). FIG. 6 (panel e) provides a graph of plasma insulin levels of ClpP-cKO mice before and 3 weeks after AAV injection. FIG. 6 (panel f) provides a graph of blood glucose levels of ClpP-cKO mice before and 3 weeks after AAV injection. FIG. 6 (panel g) provides a glucose tolerance curve of ClpP-cKO mice 4 weeks after AAV injection. FIG. 6 (panel h) provides a glucose tolerance curve of ClpP-cKO mice injected with AAV-Cre or control AAV and on HFD for 2 weeks. FIG. 6 (panel i) provides a graph of data collected after HFD was given to mice 6 weeks after AAV injection. No differences of body weight gain were detected after 2 or 4 weeks on HFD. Data are mean±SD. *P<0.01, ***P<0.005 versus control.

FIG. 7 (panel a) provides a schematic of the gene-trapping strategy used to generate ClpP$^{-/-}$ mice. FIG. 7 (panels b-i) provide western blots and quantification of ClpP protein levels in lysates of the liver, adipose tissue, muscle, and brain. Data are mean±SD. ***P<0.005 versus WT.

FIG. 8 (panel a), FIG. 8 (panel b) provide representative H&E-stained images of the liver (a) and gastrocnemius muscle (b) in WT, ClpP$^{+/-}$, and ClpP$^{-/-}$ mice. Scale bars are 50 μm.

FIG. 9 (panels a-e) provide graphs of data collected from performing the grip test, incline test, tail suspense test, and rotarod test of 8-month-old male mice (n=8 for each group). FIG. 9 (panel f) provides a graph from the elevated plus maze test performed with 8-9-month-old male mice (n=8 for each group). FIG. 9 (panels g-j) provide graphs from the Morris water maze test performed with 8-9-month-old male and female mice (n=8 for each group) (-♦- WT, -■- ClpP$^{+/-}$, -▲- ClpP$^{-/-}$). H, hidden trial; V, visible trial. Data are mean±SEM.

FIG. 10 (panels a-d) provide representative images of H&E-stained adipose tissues from WT, ClpP$^{+/-}$, and ClpP$^{-/-}$ mice.

FIG. 11 (panel a), FIG. 11 (panel b) provide representative H&E-stained images of the brown adipose tissue (a) and pancreas (b) in WT, ClpP$^{+/-}$, and ClpP$^{-/-}$ mice. Scale bars are 100 μm.

FIG. 12 (panel a), FIG. 12 (panel b) provide graphs of body weight gain of 8-month-old male mice after being on an HFD for 10 days and 20 days (n=8 for WT and ClpP$^{+/-}$, n=7 for ClpP$^{-/-}$). FIG. 12 (panel c), FIG. 12 (panel d) provide graphs of the lean body mass of 8-month-old male mice after being on the HFD for 40 days (n=6 for WT, n=7 for ClpP$^{+/-}$ and ClpP$^{-/-}$). Data are mean±SD. P<0.01, *P<0.005 versus WT.

FIG. 13 (panel a), FIG. 13 (panel b) provide graphs depicting the total movement and the ratio of center to total movement for 8-10-month-old male mice during an open field test (n=10 for WT, n=12 for ClpP$^{+/-}$ and ClpP$^{-/-}$). Data are mean±SEM.

FIG. 14 (panel a) provides a graph of the body weight of 4-8-month-old db/db mice with different ClpP genotypes (n=10 for WT, n=17 for ClpP$^{+/-}$, n=8 for ClpP$^{-/-}$). FIG. 14 (panel b), FIG. 14 (panel c) provide graphs depicting the levels of blood glucose and plasma insulin of 3-7-month-old db/db mice with different ClpP genotypes after a 16-h fast (n=8 for WT, n=7 for ClpP$^{+/-}$, n=6 for ClpP$^{-/-}$). Data are mean±SD. *P<0.05 versus WT.

FIG. 15 (panel a) provides an image of 2D-DIGE profiles of WT versus ClpP$^{-/-}$ or WT versus ClpP$^{+/-}$ livers. FIG. 15 (panel b) provides an image of 2D-DIGE profiles of WT versus ClpP$^{-/-}$ or WT versus ClpP$^{+/-}$ muscles. FIG. 15 (panel c) provides an image of 2D-DIGE profiles of WT versus ClpP$^{-/-}$ or WT versus ClpP$^{+/-}$ hippocampi. Green, WT; red, ClpP$^{-/-}$ or ClpP$^{+/-}$.

FIG. 16 (panel a), FIG. 16 (panel b) provide Western blots and quantification of OAT, LonP, SDH2, ATP6V1A, VDAC, Hsp60, CPS1, Hsp70, Grp78, and Hsp60 in lysates of different organs. Data are mean±SD. *P<0.05, P<0.01, *P<0.005 versus WT.

FIG. 17 (panels a-d) provide data showing that knocking out ClpP altered mitochondrial numbers and morphology in mouse hepatocytes. FIG. 17 (panel a), FIG. 17 (panel b) provide representative electron microscopic image of mitochondria in WT (a) and ClpP$^{-/-}$ (b) mouse hepatocytes. Scale bars are 2 µm. FIG. 17 (panel c) provides a histogram of mitochondrial size distribution in WT and ClpP$^{-/-}$ mouse hepatocytes (n=507 for WT, n=529 for ClpP$^{-/-}$). FIG. 17 (panel d) provides a histogram of mitochondrial roundness distribution in WT and ClpP$^{-/-}$ mouse hepatocytes (n=507 for WT, n=529 for ClpP$^{-/-}$). The roundness was defined as $4\times(area)/(\pi\times(major\ axis)^2)$ and measured via Image J at ×13,600 magnification.

FIG. 18 (panels a-d) provide representative western blots and quantifications of LRPPRC, TRAP1, Grp75, and ClpX protein levels in ClpP$^{-/-}$ fibroblasts treated by different lentiviral shRNAs for 48 hours. FIG. 18 (panel e) provides a graph depicting cell viability in response to H$_2$O$_2$ treatment of ClpP$^{-/-}$ fibroblasts treated with LRPPRC lentiviral shRNAs (n=8 for each group) (-♦- ClpP$^{-/-}$, -■- ClpP$^{-/-}$+LRPPRC-shRNA). FIG. 18 (panel f) provides a graph depicting cell viability in response to H$_2$O$_2$ treatment of ClpP$^{-/-}$ fibroblasts treated with ClpX lentiviral shRNAs (n=8 for each group) (-♦- ClpP$^{-/-}$, -■- ClpP$^{-/-}$+ ClpX-shRNA). Data are mean±SD. P<0.01, *P<0.005 versus ClpP$^{-/-}$.

FIG. 19 (panels a-b) provide a western blot of ClpP levels in adipose tissues of adipocyte-specific ClpP-cKO mice, and a graph of the data. FIG. 19 (panel c) provides a graph of body weights of 5-10-month-old adipocyte-specific ClpP-cKO mice compared to controls (no Cre littermates) (n=30 for no Cre, n=24 for Ad-Cre). FIG. 19 (panel d) provides a graph of the blood glucose levels of 5-10-month-old adipocyte-specific ClpP-cKO mice compared to controls (no Cre littermates) (n=30 for no Cre, n=24 for Ad-Cre). FIG. 19 (panel e) provides a glucose tolerance curve of 3-6-month-old adipocyte-specific ClpP-cKO mice compared to controls (no Cre littermates) (n=13 for no Cre, n=11 for Ad-Cre) (-♦- no Cre, -■- Ad-Cre). FIG. 19 (panel f) provides a graph of body weight gain of 9-12-month-old adipocyte-specific ClpP-cKO mice in response to HFD (n=9 for no Cre, n=11 for Ad-Cre). FIG. 19 (panel g) provides a glucose tolerance curve of 9-12-month-old adipocyte-specific ClpP-cKO mice after 4 Week on HFD (n=9 for no Cre, n=11 for Ad-Cre). ***P<0.005 versus No Cre.

FIG. 20 provides a table of proteins differentially expressed in ClpP-KO tissues.

FIG. 21 provides a table of potential substrates of ClpXP.

FIG. 22 provides a table showing that the expression of potential ClpXP substrates were not upregulated at transcription levels, as determined by microarray assays.

FIG. 31 also provides a graph showing the results of a glucose tolerance test showing increased insulin sensitivity in HFD-fed WT mice treated with A2-32-01 compared to those treated with vehicle (n=9 for vehicle group, n=10 for A2-32-01 group) (right panel).

FIG. 32 also provides a graph showing that the levels of tentative ClpP effectors, measured by western, were higher in liver mitochondrion lysates from A2-32-01-treated mice compared to those from vehicle-treated mice (n=8 for vehicle group, n=10 for A2-32-01 group) (right panel).

FIG. 34, Panel B, provides a graph showing body weight change of db/db mice in response to A2-32-01 treatment. (n=7 for vehicle group, n=9 for A2-32-01 group).

FIG. 35, Panel D, provides a graph showing that fasting blood glucose levels in db/db mice treated with A2-32-01 are significantly lower than those treated with vehicle (n=7 for vehicle group, n=9 for A2-32-01 group). FIG. 35, Panel E, provides a graph showing that ClpP activity was lower in liver mitochondria lysates from db/db mice treated with A2-32-01 compared to those treated with vehicle (n=7 for vehicle group, n=9 for A2-32-01 group).

DETAILED DESCRIPTION

Figure 1:
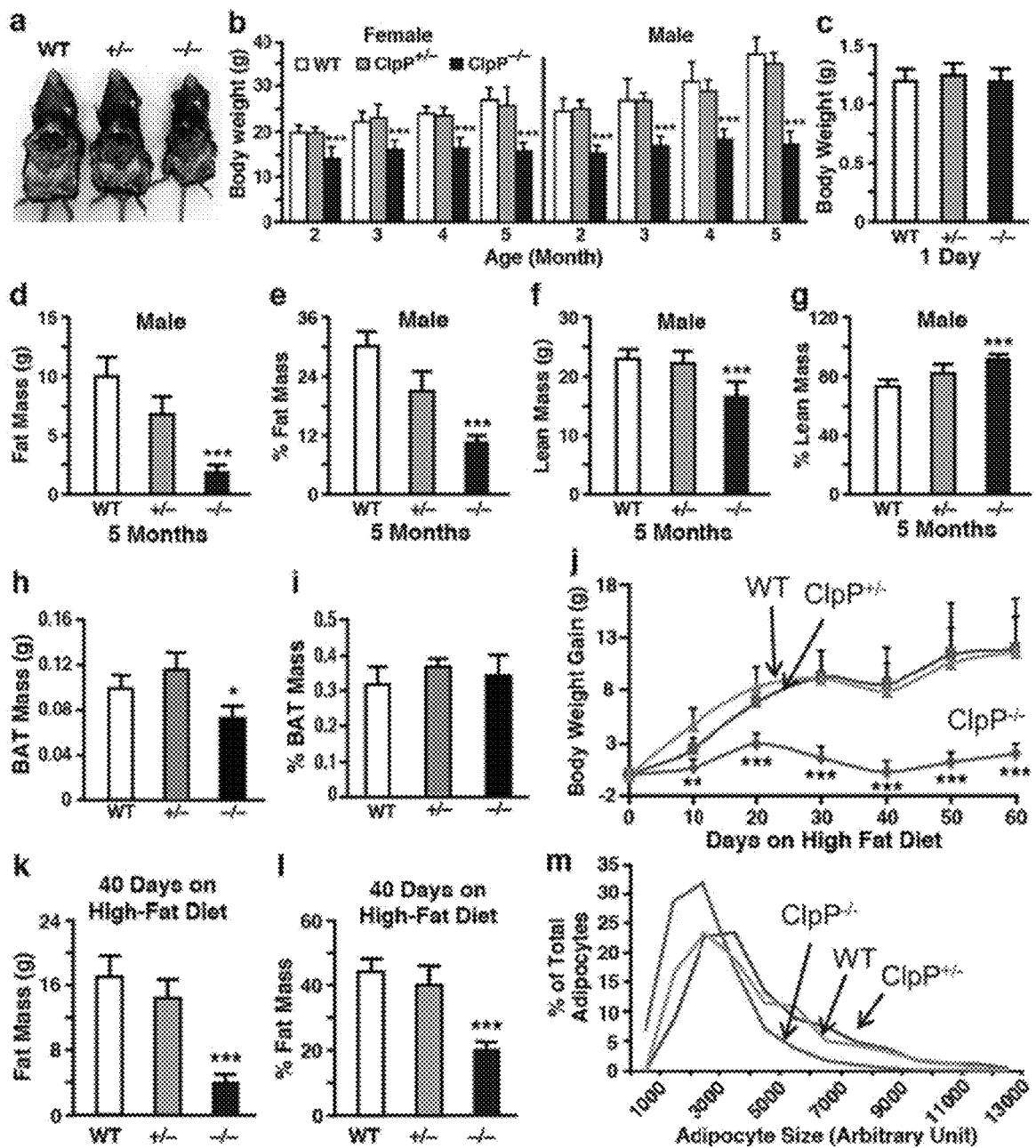
FIG. 1 (panels a-m) provides data showing that ClpP$^{-/-}$ mice had less body fat and a resistance to high-fat diet-induced obesity.

Provided are methods and compositions for identifying candidate agents for the treatment of obesity, liver disease, and/or diabetes. In some embodiments, such methods include (a) contacting a mammalian cell or cell population with a test agent, and (b) measuring an expression level (e.g., protein and/or mRNA) and/or activity level of ClpP in the mammalian cell (the agent-contacted cell) or in cells of the agent-contacted cell population. If the compound (the test agent) reduces ClpP expression (e.g., as can be show by measuring levels of ClpP protein and/or ClpP-encoding mRNA) and/or activity level, it is then considered to be a "candidate agent" (e.g., a candidate agent for treatment). Also provided are methods and compositions for treating an individual (e.g., one who is obese and/or has diabetes or who has been diagnosed as such). Treatment methods include administering an inhibitor of ClpP (e.g., an RNAi agent or a gene editing agent that targets ClpP) to the individual (e.g., to prevent or reduce weight gain, to increase insulin sensitivity, and/or to increase glucose tolerance).

Before the present methods and compositions are described, it is to be understood that this invention is not limited to the particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

ClpP Protein

Mammalian ClpXP is a protein complex (a protease) that has a catalytic subunit (the ClpP protein) and a regulatory subunit (the ClpX protein). As described herein, it has been discovered that the ClpP protein plays an important biological role in mitochondrial function in mammalian cells, and that altering the expression/function of ClpP has wide-ranging physiological consequences.

The wild type mouse and human ClpP protein amino acid sequences (and their encoding mRNAs) are depicted here.

```
Wild type human ClpP (NP_006003.1)
*also known as "caseinolytic mitochondrial matrix peptidase
proteolytic subunit", DFNB81, and PRLTS3
                                                       (SEQ ID NO: 1)
MWPGILVGGARVASCRYPALGPRLAAHFPAQRPPQRTLQNGLALQRCLHAT

ATRALPLIPIVVEQTGRGERAYDIYSRLLRERIVCVMGPIDDSVASLVIAQLLFL

QSESNKKPIHMYINSPGGVVTAGLAIYDTMQYILNPICTWCVGQAASMGSLLL

AAGTPGMRHSLPNSRIMIHQPSGGARGQATDIAIQAEEIMKLKKQLYNIYAKHT

KQSLQVIESAMERDRYMSPMEAQEFGILDKVLVHPPQDGEDEPTLVQKEPVE

AAPAAEPVPAST
```

-continued

DNA version of the mRNA encoding human ClpP (above) (NM_006012.2)
*ORF is underlined (SEQ ID NO: 3)
CCTTAATGGCGCCCGCCCAGACTCCTGGAAGTGAGCGGCCTAGCGAGCG

AGCTCCCAGGCGCAAAGCACGCCGGAAGCTGTAGTTCCGCCATCGGACG

GAAGCCGACCGGGGCGTGCGGAGG<u>ATGTGGCCCGGAATATTGGTAGG</u>

<u>GGGGGCCCGGGTGGCGTCATGCAGGTACCCCGCGCTGGGGCCTCGCCT</u>

<u>CGCCGCTCACTTTCCAGCGCAGCGGCCGCCGCAGCGGACACTCCAGAAC</u>

<u>GGCCTGGCCCTGCAGCGGTGCCTGCACGCGACGGCGACCCGGGCTCTC</u>

<u>CCGCTCATTCCCATCGTGGTGGAGCAGACGGGTCGCGGCGAGCGCGCCT</u>

<u>ATGACATCTACTCGCGGCTGCTGCGGGAGCGCATCGTGTGCGTCATGGG</u>

<u>CCCGATCGATGACAGCGTTGCCAGCCTTGTTATCGCACAGCTCCTCTTCC</u>

<u>TGCAATCCGAGAGCAACAAGAAGCCCATCCACATGTACATCAACAGCCCT</u>

<u>GGTGGTGTGGTGACCGCGGGCCTGGCCATCTACGACACGATGCAGTACA</u>

<u>TCCTCAACCCGATCTGCACCTGGTGCGTGGGCCAGGCCGCCAGCATGGG</u>

<u>CTCCCTGCTTCTCGCCGCCGGCACCCCAGGCATGCGCCACTCGCTCCCC</u>

<u>AACTCCCGTATCATGATCCACCAGCCCTCAGGAGGCGCCCGGGGCCAAG</u>

<u>CCACAGACATTGCCATCCAGGCAGAGGAGATCATGAAGCTCAAGAAGCAG</u>

<u>CTCTATAACATCTACGCCAAGCACACCAAACAGAGCCTGCAGGTGATCGA</u>

<u>GTCCGCCATGGAGAGGGACCGCTACATGAGCCCCATGGAGGCCCAGGA</u>

<u>GTTTGGCATCTTAGACAAGGTTCTGGTCCACCCTCCCCAGGACGGTGAGG</u>

<u>ATGAGCCCACGCTGGTGCAGAAGGAGCCTGTAGAAGCAGCGCCGGCAGC</u>

<u>AGAACCTGTCCCAGCTAGCACCT</u>GAGAGCTGGGCCTCCTCTCCAGAATCA

TGTGGAGGGGCCAGAGGCCTGCCAGACCCCCAGCTGGGCCCTGCTCAC

CCCTTGTTGCTGGGCTTGGAGGGGCCTCTTGAGGAACTTTTAATTTGCAG

GGGTGCCCGCTATGGACGGGGCATTCCAGCTGAGACACTGTGATTTTAAA

TTAAATCTTTGTGGTCTTTGCAAAAAAAAAAAAAAAAAAAAAAAAAAAAA

AAAAAAAAAAA

Wild type mouse ClpP (NP_059089.1)
*also known as "caseinolytic mitochondrial matrix peptidase
proteolytic subunit", AU019820, and D17Wsu160e (SEQ ID NO: 2)
MWPRVLLGEARVAVDGCRALLSRLAVHFSPPWTAVSCSPLRRSLHGTATRA

FPLIPIVVEQTGRGERAYDIYSRLLRERIVCVMGPIDDSVASLVIAQLLFLQSES

NKKPIHMYINSPGGVVTAGLAIYDTMQYILNPICTWCVGQAASMGSLLLAAGS

PGMRHSLPNSRIMIHQPSGGARGQATDIAIQAEEIMKLKKQLYNIYAKHTKQSL

QVIESAMERDRYMSPMEAQEFGILDKVLVHPPQDGEDEPELVQKETATAPTD

PPAPTST

DNA version of the mRNA encoding mouse ClpP (above) (NM_017393.2)
*ORF is underlined (SEQ ID NO: 4)
AGTGACTCCCGCAAAGCACGCCGGGTGTTGTAGTTCCGGAAGCCAAGCC GGAGTGCGCGTCGTC<u>ATGTGGCCCAGAGTGCTGCTGGGGGAGGCCCGG</u>

<u>GTGGCTGTGGACGGATGTCGCGCTCTGTTGTCTCGCCTTGCCGTGCATTT</u>

<u>CTCCCCGCCATGGACTGCTGTGAGCTGCTCACCCCTGCGGAGGAGCCTG</u>

<u>CATGGAACTGCGACGCGAGCTTTCCCGCTCATCCCCATAGTGGTGGAGC</u>

-continued

```
AGACGGGTCGAGGCGAGCGCGCTTATGACATATACTCGAGGCTGTTGCG

GGAACGCATCGTGTGCGTCATGGGCCCGATTGACGACAGTGTGGCCAGT

CTGGTCATTGCCCAGCTGTTGTTCTTACAGTCTGAAAGCAACAAGAAGCC

CATTCATATGTATATCAACAGCCCAGGTGGTGTGGTAACTGCGGGCCTGG

CCATCTACGACACAATGCAGTACATCCTGAACCCCATCTGCACGTGGTGT

GTTGGACAGGCTGCCAGCATGGGCTCCCTGCTCCTCGCTGCTGGCAGCC

CGGGCATGCGCCATTCACTGCCCAATTCCAGAATCATGATCCACCAGCCC

TCTGGAGGAGCCAGGGGCCAAGCCACAGACATCGCCATCCAGGCAGAGG

AAATCATGAAGCTGAAAAAGCAGCTATACAACATCTACGCCAAACACACCA

AGCAGAGCCTACAGGTGATCGAGTCAGCAATGGAGAGGGACCGCTACAT

GAGCCCCATGGAGGCCCAAGAGTTTGGCATCTTGGACAAGGTCTTGGTC

CACCCACCTCAGGACGGGGAGGATGAGCCAGAACTGGTACAGAAGGAGA

CTGCCACAGCGCCGACGGATCCTCCTGCCCCGACAAGCACCTAAGGAGT

GGAGACCAGACTGAAACTTCCTCTGCTGGGCCCAAGAACAACCCCTAGAG

GAGATGTGGATTGAGGTTGCCCTCAGAGCAGGGCAGACTGCCTGAGACA

CTGTGATTTAAATTAAATCTTTGTAGTCTTTGTCCCATGTCTGAAGCACCTT

CCATTACTTCTCCAAGACAGCAGGCCTCCTTCACCTTGACAAACCACTTCA

GTAAGCAAACCCTGGCTCTCCTGGAACTAAACCAATCTAGCCTCAGACTC

AGGTACCCACCTGCCTCACCTCCTGAGTGCTAGGATTAAAGGTGTACACC

ACCACACCTGACTTCAA
```

Screening Methods

Provided are screening methods for identifying candidate agents for treating obesity, liver disease, and/or diabetes. By way of example, such candidate agents may include candidate agents for decreasing an amount of fat tissue in an individual, preventing or reducing weight gain of an individual, increasing insulin sensitivity of an individual, and/or increasing glucose tolerance of an individual. In some embodiments, screening methods provided herein include (a) contacting a mammalian cell or cell population (e.g., a mouse cell, a rat cell, a non-human primate cell, a human cell, or a cell population thereof) with a test agent, and (b) measuring an expression level and/or activity level of ClpP (e.g., a protein and/or mRNA expression level or an activity level of ClpP) in the mammalian cell (the agent-contacted cell) or in cells of the agent-contacted cell population to determine whether the test agent caused a reduction of ClpP expression and/or activity level in the cell or cells of the cell population.

Test agents that reduce ClpP expression (e.g., protein and/or mRNA) and/or activity level, can be identified as candidate agents for use in the treatment of obesity, liver disease, and/or diabetes. Thus, a compound is considered to be a "test agent" prior to contact with a cell or cell population (e.g., in vitro, ex vivo, or in vivo), and if the compound (the test agent) reduces ClpP expression (e.g., as can be show by measuring levels of ClpP protein and/or ClpP-encoding mRNA) and/or activity level, it is then considered to be a "candidate agent" (e.g., a candidate agent for the treatment of diseases in which ClpP reduction is beneficial, such as obesity, liver disease, and/or diabetes). Thus, the provided screening methods can also be referred to as methods of identifying an inhibitor of ClpP, methods of identifying an agent that reduces ClpP expression and/or activity level, methods of identifying an inhibitor of ClpP expression and/or activity level, and the like.

In some embodiments, a subject method (e.g., a method as described above) includes (a) contacting a mammalian cell (e.g., a mouse cell, a rat cell, a non-human primate cell, a human cell) with a test agent; (b) measuring a decrease in the expression level and/or activity level of ClpP caused by the contacting step (e.g., relative to a reference value, e.g., an expression level and/or activity level of ClpP prior to contact with the test agent, an expression level and/or activity level of ClpP after contact with a control agent that is known not to reduce ClpP expression, and the like); (c) determining that the test agent caused a decrease in the expression level and/or activity level relative to the reference value; and (d) identifying the test agent as a candidate agent for treating obesity, liver disease, and/or diabetes.

In some cases, the contacting is in vitro (e.g., the cell is in culture and is contacted in vitro). In some cases, the contacting is ex vivo (e.g., the cell is in culture and is a primary cell isolated from an individual).

A subject screening method includes a step of contacting a cell (or cell population) with a test agent. When a test agent reduces a ClpP expression level (e.g., at the level of ClpP protein or mRNA encoding the ClpP protein) and/or activity level, that agent is determined to be a candidate agent (e.g., for treating obesity, liver disease, and/or diabetes). Thus, the contacting will generally be for a period of time such that a change in an expression level and/or activity level of ClpP (e.g., protein and/or mRNA expression level) can potentially be detected. In other words, the period of contact will be for a suitable period of time after which one may reasonably expect that if a test agent is in fact a candidate agent for treatment, a change in ClpP expression and/or activity level will be detectable. In some cases, the contacting is for a period of time of 2 or more minutes (e.g., 5 or more minutes, 10 or more minutes, 15 or more minutes, 30 or more minutes, 1 or more hours, 2 or more hours, 5 or more hours, 6 or more hours, 12 or more hours 18 or more hours, etc.). In some cases, the contacting is for a period in a range of from 2 minutes to 48 hours (e.g., 5 minutes to 24 hours, 5 minutes to 6 hours, 5 minutes to 2 hours, 15 minutes to 24 hours, 15 minutes to 6 hours, 15 minutes to 2 hours, 1 hour to 24 hours, 1 hour to 6 hours, or 1 hour to 2 hours).

In some cases, the contacting is in vivo. For example, in some cases, a subject method (e.g., a screening method) includes a step of administering an agent (e.g., a test agent or a candidate agent) to an individual. A step of administering can serve a number of different purposes. For example, in some cases a subject method includes a step of administering a test agent to an individual (e.g., a mouse or a rat), and then measuring an expression level and/or activity level of ClpP in order to determine whether the test agent is a candidate agent for treatment. Such administration can be performed as part of the screen for identifying those test agents that are candidate agents for treatment.

As another example, in some cases a subject method (e.g., a screening method) includes a step of administering a candidate agent (i.e., an agent that has already been determined to reduce an expression level and/or activity level of ClpP, e.g., using a subject method and contacting a cell in vitro, ex vivo, or in vivo). Such administration can be performed as a treatment step, or for example, in order to determine whether the candidate agent causes a measurable change in features associated with obesity, liver disease, and/or diabetes (e.g., decrease in an amount of fat tissue, prevention or reduction of weight gain, increase in insulin sensitivity, increase in glucose tolerance, and the like).

Target Cells

Any suitable mammalian cell or cell population can be used in the provided screening methods as a target cell or cell population (i.e., a cell or cell population that is contacted with a test agent). For example, in some cases, the target cell or cell population (the cell or cell population contacted with the test agent) is a mammalian cell, a rodent cell (e.g., a mouse cell, a rat cell), a rabbit cell, a non-human primate cell, a human cell, etc. As noted above, the target cell or cell population can be in vitro (e.g., from an establish cell line), ex vivo (e.g., primary cells), or in vivo. The target cell can be any suitable type of cell (e.g., a stem cell, a progenitor cell, an adipocyte, a neuron, a cell of the pancreas, a fibroblast, an epithelial cells, a kidney cell, an embryonic cell, and the like), and in some cases, the contacted cell (the target cell) is a hepatocyte.

Examples of suitable mammalian cells for the subject screening methods include, but are not limited to: monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2).

Test Agents

A "test agent" (e.g., "test compound") to be used in the provided screening methods can be any suitable agent (e.g., including, but not limited to, organic molecules, small molecules, polynucleotides, RNA, DNA, proteins, antibodies, peptides, lipids, carbohydrates, and the like). A test agent can also be a mixture of chemical compounds. In some cases, an array of spatially localized test agents can be used (e.g., a peptide array, polynucleotide array, and/or combinatorial small molecule array; where "array" refers to a collection of different molecular species immobilized on a surface). In some cases, a small molecule library is screened (i.e., a test agent can be a member of a small molecule library). Test agents can be biological macromolecules, can be part of a bacteriophage peptide display library, can be part of a bacteriophage antibody (e.g., scFv) display library, a polysome peptide display library, and the like. A test agent can be an extract made from biological materials such as bacteria, plants, fungi, or animal (e.g., mammalian) cells and/or tissues. As provided in the subject screening methods, test agents are evaluated for potential activity as agents for treating obesity, liver disease, and/or diabetes (e.g., candidate agents for decreasing an amount of fat tissue in an individual, preventing or reducing weight gain of an individual, increasing insulin sensitivity of an individual, and/or increasing glucose tolerance of an individual). In some cases, a subject method is for screening a plurality of test agents. Test agents can be evaluated (screened) individually (sequentially), or in parallel.

In some cases, a test agent (e.g., a test compound) can have a formula weight of less than 10,000 grams per mole (e.g., less than 5,000 grams per mole, less than 1,000 grams per mole, or less than 500 grams per mole). A test agent can be naturally occurring (e.g., an herb or a natural product), synthetic, or can include both natural and synthetic components. Examples of small molecules include peptides, peptidomimetics (e.g., peptoids), amino acids, amino acid analogs, polynucleotides, polynucleotide analogs, nucleotides, nucleotide analogs, and small molecules, such as organic or inorganic compounds, e.g., heteroorganic or organometallic compounds.

ClpP Expression Level and/or Activity Level

In some cases, a subject screening method includes a step of measuring a ClpP expression level and/or activity level. Because reduction of ClpP mRNA can result in reduced ClpP protein level, either assay (one to measure ClpP-encoding mRNA or one to measure ClpP protein) can be used for measuring an expression level. For example, in some cases, a test agent that reduces the level of ClpP protein in the target cell (or in cells of the target cell population) will be identified as a candidate agent for use in treating obesity, liver disease, and/or diabetes. In some cases, a test agent that reduces the level of ClpP-encoding mRNA in the target cell (or in cells of the target cell population) will be identified as a candidate agent for use in treating obesity, liver disease, and/or diabetes.

The terms "assaying" and "measuring" are used herein to include the physical steps of manipulating a biological sample (e.g., cell sample) to generate data related to the sample (e.g., measuring an expression level and/or activity level in a biological sample). In practicing the subject methods, the expression level of a ClpP expression product (e.g., mRNA or protein) and/or an activity level of ClpP can be measured. The expression level may be the expression level in a cell, in a population of cells, in a biological sample from an individual, and the like. The expression level(s) and/or activity level(s) can be measured by any suitable method. For example, an RNA expression level can be measured by measuring the levels/amounts of one or more nucleic acid transcripts, e.g. mRNAs, of ClpP. Protein expression levels of ClpP can be detected by measuring the levels/amounts of the ClpP protein.

"Measuring" can be used to determine whether the measured expression level and/or activity level is less than, greater than, "less than or equal to", or "greater than or equal to" a particular threshold, (the threshold can be pre-determined or can be determined by assaying a control sample). On the other hand, "measuring to determine the expression level" (and/or activity level) or simply "measuring expression levels" (and/or activity levels) can mean determining a quantitative value (using any suitable metric) that represents the level of expression (e.g., the amount of protein and/or RNA, e.g., mRNA) of a particular expression product (e.g., a ClpP expression product) and/or the activity level of ClpP. The level of expression and/or activity can be expressed in arbitrary units associated with a particular assay (e.g., fluorescence units, e.g., mean fluorescence intensity (MFI), threshold cycle ($C_t$), quantification cycle ($C_q$), and the like), or can be expressed as an absolute value with defined units (e.g., number of mRNA transcripts, number of protein molecules, concentration of protein, amount of substrate cleaved, etc.).

An expression level and/or activity level can be a raw measured value, or can be a normalized and/or weighted value derived from the raw measured value. The terms "expression level" and "measured expression level" are used herein to encompass raw measured values as well as values that have been manipulated in some way (e.g., normalized and/or weighted). In some cases, a normalized expression level and/or activity level is a measured expression level of an expression product and/or an activity level from a sample where the raw measured value for the expression product and/or activity level has been normalized. For example, the expression level of an expression product (e.g., an RNA encoding ClpP, a ClpP protein) can be compared to the expression level of one or more other expression products (e.g., the expression level of a housekeeping gene, the averaged expression levels of multiple genes, etc.) to derive a normalized value that represents a normalized expression level. Methods of normalization will be known to one of ordinary skill in the art and any suitable normalization method can be used. The specific metric (or units) chosen is not crucial as long as the same units are used (or conversion to the same units is performed) when evaluating multiple markers and/or multiple biological samples (e.g., samples from multiple individuals or multiple samples from the same individual).

A reduction of a ClpP expression level and/or activity level can be determined in a number of different ways. For example, in some cases, a ClpP expression level and/or activity level is measured in a cell (or in an individual, e.g., in a biological sample from the individual) prior to and after contact with a test agent (or prior to and after administration of an agent to an individual), and a determination is made as to whether a reduction was caused by the contacting (or the administration). In some cases, some cells of a cell population are not contacted with an agent (e.g., a test agent) and other cells of the cell population are contacted with an agent (e.g., a test agent) and a comparison can be made among the contacted and non-contacted cells. In some cases, some cells of a cell population are not contacted with an agent (e.g., a test agent) and other cells of the cell population are contacted with a mock agent (e.g., an agent known not to cause a change) and a comparison can be made among the cells contacted with the test agent and those (control cells) contacted with the mock agent (control agent).

Such comparisons can generally be referred to as comparing a measured value to a reference value, or determining that an agent caused a reduction in a ClpP expression level and/or activity level as compared to a reference value. A reference value can be a level of ClpP (protein and/or mRNA) and/or activity level of ClpP measured prior to contact with an agent, a level of ClpP (protein and/or mRNA) and/or activity level of ClpP measured after contact with a mock agent (control agent), a level of ClpP (protein and/or mRNA) and/or activity level of ClpP measured in the absence of contact with an agent, etc. A reference value can also be in some cases a pre-determined (threshold) value.

In some cases, a subject method includes determining that a test agent or a candidate agent caused a decrease in the expression level and/or activity level of ClpP. In some cases, the expression level and/or activity level is reduced by 10% or more (e.g., 20% or more, 30% or more, 40% or more, 50% or more, 60% or more, 70% or more, 80% or more, or 90% or more) compared to a reference value (e.g., an activity level and/or expression level, e.g., of ClpP protein and/or mRNA, prior to contact with the agent; an activity level and/or expression level, e.g., of ClpP protein and/or mRNA, in mock-treated cells or in mock-treated control individuals; etc.). In some cases, the measured expression level and/or activity level is 95% of a reference value or less (e.g., 90% of the reference value or less, 85% of the reference value or less, 80% of the reference value or less, 75% of the reference value or less, 70% of the reference value or less, 65% of the reference value or less, 60% of the reference value or less, 55% of the reference value or less, 50% of the reference value or less, 45% of the reference value or less, 40% of the reference value or less, 35% of the reference value or less, 30% of the reference value or less, 25% of the reference value or less, 20% of the reference value or less, 15% of the reference value or less, 10% of the reference value or less, or 5% of the reference value or less). In some cases, the reference value of the expression level and/or activity level of ClpP is 1.1-fold or more (e.g., 1.2-fold or more, 1.3-fold or more, 1.4-fold or more, 1.5-fold or more, 2-fold or more, 2.5-fold or more, 3-fold or more, 4-fold or more, 5-fold or more, 7.5-fold or more, or 10-fold or more) greater than the measured value.

Measuring RNA

An expression level of an expression product of ClpP may be measured by detecting the amount or level of one or more RNA transcripts or a fragment thereof encoded by the gene of interest (ClpP). Such detection may include detecting the level of one or more RNA transcripts or a fragment thereof encoded by the ClpP gene in a cell extract, in a fixed cell, in a living cell, in a biological sample, etc. For measuring RNA levels, the amount or level of an RNA in the sample is determined, e.g., the expression level of an mRNA. In some instances, the expression level of one or more additional RNAs may also be measured, and the level of ClpP RNA expression compared to the level of the one or more additional RNAs to provide a normalized value for the ClpP expression level.

The expression level of nucleic acids in a sample (e.g., the expression level of a ClpP mRNA) may be detected using any suitable protocol. A number of exemplary methods for measuring RNA (e.g., mRNA) expression levels in a sample are known by one of ordinary skill in the art, such as those methods employed in the field of differential gene expression analysis, and any suitable method can be used. Exemplary methods include, but are not limited to: hybridization-based methods (e.g., Northern blotting, array hybridization (e.g., microarray); in situ hybridization; in situ hybridization followed by FACS; and the like) (Parker & Barnes, Methods in Molecular Biology 106:247-283 (1999)); RNAse protection assays (Hod, Biotechniques 13:852-854 (1992)); PCR-based methods (e.g., reverse transcription PCR (RT-PCR), quantitative RT-PCR (qRT-PCR), real-time RT-PCR, etc.) (Weis et al., Trends in Genetics 8:263-264 (1992)); nucleic acid sequencing methods (e.g., Sanger sequencing, Next Generation sequencing (i.e., massive parallel high throughput sequencing, e.g., Illumina's reversible terminator method, Roche's pyrosequencing method (454), Life Technologies' sequencing by ligation (the SOLiD platform), Life Technologies' Ion Torrent platform, single molecule sequencing, etc.); nanopore based sequencing methods; and the like.

In some embodiments, the biological sample can be assayed directly. In some embodiments, nucleic acid of the biological sample is amplified (e.g., by PCR) prior to assaying. As such, techniques such as PCR (Polymerase Chain Reaction), RT-PCR (reverse transcriptase PCR), qRT-PCR (quantitative RT-PCR, real time RT-PCR), etc. can be used prior to the hybridization methods and/or the sequencing methods discussed above.

Examples of some of the methods listed above are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39); Soni et al Clin Chem 53: 1996-2001 2007; and Morozova (Genomics. 2008 92:255-64), which are herein incorporated by reference for the general descriptions of the methods and the particular steps of the methods, including starting products, reagents, and final products for each of the steps.

Measuring Protein

An expression level of an expression product of ClpP may be measured by detecting the amount or level of one or more proteins (e.g., ClpP) or a fragment thereof. Such detection may include detecting the level of a ClpP protein or a fragment thereof in a cell extract, in a fixed cell, in a living cell, in a biological sample, etc. For measuring a protein level, the amount or level of protein the sample (e.g., in a cell, in a population of cells, in a cell extract, etc.) is determined. In some instances, the concentration of one or more additional proteins may also be measured, and the measured expression level compared to the level of the one or more additional proteins to provide a normalized value for the measured expression level. In some embodiments, the measured expression level is a relative value calculated by comparing the level of one protein relative to another protein. In other embodiments the concentration is an absolute measurement (e.g., weight/volume or weight/weight).

The expression level of a protein (e.g., ClpP) may be measured by detecting in a sample the amount or level of one or more proteins/polypeptides or fragments thereof. The terms "polypeptide," "peptide" and "protein" are used interchangeably herein to refer to a polymer of amino acid residues. "Polypeptide" refers to a polymer of amino acids (amino acid sequence) and does not refer to a specific length of the molecule. Thus peptides and oligopeptides are included within the definition of polypeptide. In some cases, cells are removed from a biological sample (e.g., via centrifugation, via adhering cells to a dish or to plastic, etc.) prior to measuring the expression level. In some cases, the intracellular protein level is measured by lysing cells of the sample to measure the level of protein in the cellular contents. In some cases, a level of protein can be measured without disrupting cell morphology (e.g., a protein level can be visualized, e.g., via fluorescent antibody staining, etc.)

When protein levels are to be detected, any suitable protocol for measuring protein levels may be employed. Examples of methods for assaying protein levels include but are not limited to antibody-based methods as well as methods that are not antibody based. Examples of suitable methods include but are not limited to: enzyme-linked immunosorbent assay (ELISA), mass spectrometry, proteomic arrays, xMAP™ microsphere technology, flow cytometry, western blotting, immunofluorescence, and immunohistochemistry.

Some protein detection methods are antibody-based methods. The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. Examples of antibody fragments include Fab, Fab', Fab'-SH, F(ab')$_2$, and Fv fragments; scFvs, diabodies; and multispecific or multivalent structures formed from antibody fragments.

ClpP Activity Level

As noted above, ClpP functions as part of a complex (ClpXP) that includes both ClpP and ClpX, and requires ATP to unfold and hydrolyze protein substrates. As such, any agent that disrupts the interaction between ClpP and ClpX, or that reduces the activity of the ClpP/ClpX complex (e.g., reduces the hydrolysis of protein substrates) can be considered an agent that reduces an activity level of ClpP. An activity level of ClpP can be measured using any suitable method. For example, an enzymatic assay can be used to measure ClpP activity. Parameters such as the kinetics of hydrolysis of ATP by ClpXP and/or degradation of substrate by ClpXP can be measured using any suitable method. For examples of various ways to measure ClpP activity level, see, e.g., Burton et al., Protein Sci. 2003 May; 12(5):893-902; Joshi et al., Nat Struct Mol Biol. 2004 May; 11(5): 404-11; Kang et al., J Biol Chem. 2005 Oct. 21; 280(42): 35424-32; Baker et al., Biochim Biophys Acta. 2012 January; 1823(1):15-28, and Al-Furoukh et al. (2014) PLoS ONE 9(7): e103141, the disclosure of each of which are incorporated by reference herein.

Furthermore, as demonstrated in the examples below, a decrease in ClpP activity level (in this case caused by an absence of ClpP in knockout mice) results in an increase in the amounts of the following proteins: TNF receptor-associated protein 1 (TRAP1) (mitochondrial Hsp90), heat shock protein family A (Hsp70) member 9 (Grp75) (mitochondrial Hsp70), leucine rich pentatricopeptide repeat containing (LRPPRC), caseinolytic mitochondrial matrix peptidase chaperone subunit (ClpX) (mitochondrial Hsp100), ornithine aminotransferase (OAT), and Ion peptidase 1, mitochondrial (LonP1) (a mitochondrial protease). As such, in some cases, measuring an activity level of ClpP can include measuring an amount of one or more (e.g., two or more, three or more, four or more, 5 or more, or all 6) of the following proteins: TRAP1, Grp75, LRPPRC, ClpX, OAT, and LonP. For example, a decrease in ClpP activity can be detected by measuring an increase in the levels of one or more (e.g., two or more, three or more, four or more, 5 or more, or all 6) of: TRAP1, Grp75, LRPPRC, ClpX, OAT, and LonP, e.g., relative to a suitable control, such as a level of one or more of TRAP1, Grp75, LRPPRC, ClpX, OAT, and LonP prior to contacting with a test agent as described herein.

Evaluation Steps

As described in the examples below, the inventors have discovered that mice with decreased ClpP expression (due to knockout in the genome of the ClpP gene, designated ClpP$^{(-/-)}$) exhibit a number of phenotypes, including but not limited to decreased: white adipose tissue, body fat (as measured by total body fat mass or body fat content (% fat mass)), body weight, visceral adipose adipocyte size, levels of plasma leptin, and blood glucose level (e.g., after fasting); and increased: insulin sensitivity, glucose tolerance, growth hormone levels, energy consumption (e.g., increased basal energy expenditure), levels of phosphorylated AKT (p-AKT) in muscles and/or fibroblasts, and lean content (% lean mass). ClpP$^{-/-}$ mice gained less weight and generated less fat while consuming more food, and ClpP$^{-/-}$ mice were resistant to high fat diet (HFD)-induced weight gain (e.g., the increase in fat mass and body weight due to HFD was less than the increase seen in wild type controls).

In some cases, a subject method (e.g. a screening method or a treatment method) includes, after administration of an agent to an individual (e.g., a candidate agent for treatment as identified with a subject screening method, an inhibitor of ClpP such as an RNAi agent or a genome editing agent specific for ClpP, etc.), a step of measuring one or more features of the individual (e.g., to verify that the agent produces a desired outcome). Suitable features that can be measured include, but are not limited to insulin sensitivity, blood glucose level, glucose tolerance, body fat mass, an amount of fat tissue, an amount of white adipose tissue, percent fat mass, body weight, visceral adipose adipocyte size, plasma leptin level, growth hormone level, basal energy expenditure, a level of phosphorylated AKT (p-AKT) in muscles and/or fibroblasts, percent lean mass, mitochondrial number in hepatocytes, mitochondrial mass in hepatocytes, mitochondrial morphology in hepatocytes, fibroblast respiratory capacity, fibroblast maximal oxygen consumption rate (OCR), and fibroblast resistance to $H_2O_2$-induced cytotoxicity. An evaluation step (e.g., a step of measuring one or more of the above features), can be included as part of a subject screening method (e.g., a method of identifying a candidate agent). An evaluation step (e.g., a step of measuring one or more of the above features), can also be included as part of a subject treatment method.

Generating a Report

In some cases, a subject method (e.g., any of the screening methods described above) includes a step of generating a report (e.g., a report that the test agent is a candidate agent for treating obesity, liver disease, and/or diabetes). A "report," as described herein, is an electronic or tangible document which includes report elements that provide information of interest relating to the results and/or assessments of such results of a subject method (e.g., a screening method). In some embodiments, a subject report includes a measured expression level and/or activity level as discussed in greater detail above (e.g., a raw value, a normalized value, a normalized and weighted value, etc.) (e.g., an activity level of ClpP or an expression level of a ClpP expression product, such as a ClpP protein and/or a ClpP-encoding mRNA). In some embodiments, a subject report includes a ClpP expression level and/or activity level. In some cases, a subject report includes an assessment (e.g. a determination of whether one or more test agents caused a reduction in a ClpP expression level and/or activity level). For example, a report can state whether a given test agent or list of test agents caused a reduction in a ClpP expression level and/or activity level (e.g., at the level of protein and/or mRNA), and/or whether a given test agent or list of test agents is a candidate agent for treatment.

Treatment Methods

Provided are methods that include administering to an individual an inhibitor of ClpP (such as an RNAi agent or gene editing agent specific for ClpP), where the inhibitor of ClpP reduces an activity level and/or expression level of ClpP (e.g., as can be detected at the level of protein and/or mRNA). Such methods can be referred to as methods of reducing an expression level and/or activity level of ClpP, and/or methods of treating an individual with obesity, liver disease, and/or diabetes. A discussion of ClpP activity levels and expression levels (e.g., at the level of protein and/or mRNA), and methods for measuring such levels can be found elsewhere herein.

In some embodiments, such methods are methods of treating an individual with obesity, liver disease, and/or diabetes, methods of increasing energy output, methods of reducing an amount of adipose tissue (e.g., white adipose tissue), methods of preventing or reducing weight gain, methods of increasing insulin sensitivity, and/or methods of increasing glucose tolerance. For example, in some cases, a subject method is a method of increasing energy output, reducing an amount of adipose tissue, increasing insulin sensitivity, increasing glucose tolerance, and/or preventing or reducing weight gain, and the method includes administering to the individual a ClpP inhibitor (such as an RNAi agent or gene editing agent specific for ClpP) that reduces the expression level and/or activity level of ClpP. In some embodiments, a subject method is a method of treating an individual with obesity, liver disease, and/or diabetes, and the method includes administering to the individual an inhibitor of ClpP (such as an RNAi agent or gene editing agent specific for ClpP) that reduces the expression level and/or activity level of ClpP.

In some embodiments, a subject method is a method of administering an inhibitor of ClpP to an individual (e.g., an individual who has obesity, liver disease, and/or diabetes) in an amount effective for decreasing an amount of fat tissue in the individual, preventing or reducing weight gain of the individual, increasing insulin sensitivity of the individual, and/or increasing glucose tolerance of the individual.

In some cases, any of the above subject treatment methods can include a step of measuring a ClpP expression level and/or activity level in a biological sample from the individual that is being treated (e.g., in a hepatocyte of/from the individual to whom a ClpP inhibitor was administered). In some cases, a subject treatment method includes a step of obtaining a biological sample from the individual and measuring a ClpP expression level and/or activity level of the sample. In some cases, such a step is performed before and after treatment (e.g., to verify that administration had the desired outcome).

In some cases, an inhibitor of ClpP (e.g., an RNAi agent or a gene editing agent that targets ClpP) is administered to an individual (e.g., an individual who is obese and/or has diabetes), in an amount effective for decreasing an amount of fat tissue in the individual, preventing or reducing weight gain of the individual, increasing insulin sensitivity of the individual, and/or increasing glucose tolerance of the individual.

RNAi Agents and Genome Editing Agents

In some cases, an inhibitor of ClpP (e.g., an agent that reduces an expression level and/or activity level of ClpP) is an RNAi agent or a genome editing agent that targets ClpP (e.g., is specific for ClpP). The term "RNAi agent" is used herein to mean any agent that can be used to induce a gene specific RNA interference (RNAi) response in a cell. Suitable examples of RNAi agents include, but are not limited to short interfering RNAs (siRNAs) and short hairpin RNAs (shRNAs), and micro RNAs (miRNA). An RNAi agent (e.g., shRNA, siRNA, miRNA) specific for ClpP is an agent that targets the mRNA encoding the ClpP protein. RNAi agents can readily be designed to specifically target any desired mRNA (e.g., one encoding ClpP) by choosing an appropriate nucleotide sequence.

Various RNAi agent designs (RNAi agents with various features) are known in the art and any suitable RNAi agent that targets ClpP can be used. For example, various designs of RNAi agents (as well as methods of their delivery) can be found in numerous patents, including, but not limited to U.S. Pat. Nos. 7,022,828; 7,176,304; 7,592,324; 7,667,028; 7,718,625; 7,732,593; 7,772,203; 7,781,414; 7,807,650; 7,879,813; 7,892,793; 7,910,722; 7,947,658; 7,973,019; 7,973,155; 7,981,446; 7,993,925; 8,008,271; 8,008,468; 8,017,759; 8,034,922; 8,399,653; 8,415,319; 8,426,675; 8,466,274; 8,524,679; 8,524,679; 8,569,065; 8,569,256; 8,569,258; 9,233,102; 9,233,170; and 9,233,174; all of which are incorporated herein by reference. Where appropriate, an RNAi agent may be provided in the form of a DNA encoding the agent (e.g., an expression vector encoding a shRNA). shRNAs targeting the ClpP (accession no. NM_003321) coding sequence are provided for example in Cole et al., 2015, *Cancer Cell* 27, 864-876, the disclosure of which is incorporated by reference herein in its entirety and for all purposes. These shRNAs include 5'-GCCCATCCA-CATGTACATCAA-3' (SEQ ID NO:5); 5'-CAC-GATGCAGTACATCCTCAA-3' (SEQ ID NO:6); and 5'-GCTCAAGAAGCAGCTCTATAA-3' (SEQ ID NO:7).

The terms "genome editing agent" and "genome targeting composition" are used interchangeably herein to mean a composition that includes a genome editing nuclease. In some embodiments, the genome editing nuclease binds a native or endogenous recognition sequence. In some embodiments, the genome editing nuclease is a modified endonuclease that binds a non-native or exogenous recognition sequence and does not bind a native or endogenous recognition sequence.

Examples of suitable genome editing nucleases include but are not limited to zinc finger nucleases (ZFNs), TAL-effector DNA binding domain-nuclease fusion proteins (transcription activator-like effector nucleases (TALENs)), CRISPR/Cas endonucleases (e.g., class 2 CRISPR/Cas endonucleases such as a type II, type V, or type VI CRISPR/Cas endonucleases), and recombinases (e.g., Cre recombinase, Hin recombinase, RecA, RAD51, Tre, FLP, and the like). Thus, in some embodiments, a genome editing agent is a composition that can include one or more genome editing nucleases selected from: a ZFN, a TALEN, a recombinase (e.g., Cre recombinase, Hin recombinase, RecA, RAD51, Tre, FLP, and the like), and a CRISPR/Cas endonuclease (e.g., a class 2 CRISPR/Cas endonuclease such as a type II, type V, or type VI CRISPR/Cas endonuclease).

Recombinases include but are not limited to Cre recombinase, Hin recombinase, RecA, RAD51, Tre, and FLP.

Information related to class 2 type II CRISPR/Cas endonuclease Cas9 proteins and Cas9 guide RNAs (as well as methods of their delivery) (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10): 1163-71; Cho et. al., Genetics. 2013 November; 195(3): 1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2): 333-9; and U.S. patents and patent applications: U.S. Pat. Nos. 8,906,616; 8,895,308; 8,889,418; 8,889,356; 8,871, 445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety. Examples and guidance related to type V or type VI CRISPR/Cas endonucleases and guide RNAs (as well as information regarding requirements related to protospacer adjacent motif (PAM) sequences present in targeted nucleic acids) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

Useful designer zinc finger modules include those that recognize various GNN and ANN triplets (Dreier, et al., (2001) J Biol Chem 276:29466-78; Dreier, et al., (2000) J Mol Biol 303:489-502; Liu, et al., (2002) J Biol Chem 277:3850-6), as well as those that recognize various CNN or TNN triplets (Dreier, et al., (2005) J Biol Chem 280:35588-97; Jamieson, et al., (2003) Nature Rev Drug Discov 2:361-8). See also, Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000) Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301.

For more information on ZFNs and TALENs (as well as methods of their delivery), refer to Sanjana et al., Nat Protoc. 2012 Jan. 5; 7(1):171-92 as well as international patent applications WO2002099084; WO00/42219; WO02/42459; WO2003062455; WO03/080809; WO05/014791; WO05/084190; WO08/021207; WO09/042186; WO09/054985; WO10/079430; and WO10/065123; U.S. Pat. Nos. 8,685,737; 6,140,466; 6,511,808; and 6,453,242; and US Patent Application Nos. 2011/0145940, 2003/0059767, and 2003/0108880; all of which are hereby incorporated by reference in their entirety.

Small Molecule ClpP Inhibitors

Small molecule inhibitors of ClpP are known which may find use in one or more of the screening or treatment methods described herein. For example β-Lactones, such as (3RS,4RS)-3-(non-8-en-1-yl)-4-(2-(pyridin-3-yl)ethyl) oxetan-2-one (also known as A2-32-01 and referred to herein interchangeably as A2-32-01 and A2-32) have been identified as inhibitors of both bacterial and mammalian ClpP. See, e.g., Cole et al., 2015, *Cancer Cell* 27, 864-876, the disclosure of which is incorporated by reference herein in its entirety and for all purposes.

Beta-lactones are described, for example, in U.S. Patent Application Publication 2014/0243255, the disclosure of which is incorporated by reference herein in its entirety and for all purposes, and can include, but are not limited to, trans-beta-lactones, beta-propiolactone, saturated aliphatic beta-lactones, beta-butyrolactone, beta-isobutyrolactone, beta-valerolactone, beta-isovalerolactone, beta-n-caprolactone, alpha-ethylbeta-propiolactone, alpha-isopropyl-beta-propiolactone, alpha-butyl-beta-propiolactone, alpha isopropyl-beta-propiolactone, beta isopropyl-beta-propiolactone, alpha-methyl-beta-butyrolactone, beta-ethyl-beta-butyrolactone, alpha-ethyl-beta-butyrolactone, alpha-methyl beta-propiolactone, lactones of betahydroxy-mono-carboxylic acids containing cycloalkyl, aryl and aralkyl substituents such as betacyclohexyl-beta-propiolactone, beta-phenyl-betapropiolactone, alpha-phenyl-beta-propiolactone, beta-taenzyl-beta-propiolactone and derivatives thereof.

β-Lactones inhibitors of ClpP, which may be utilized in the context of the disclosed methods, include those described in U.S. Patent Application Publication No. 2016/0221977, the disclosure of which is incorporated by reference herein in its entirety and for all purposes. Such β-Lactones inhibitors of ClpP include compounds of the following structures:

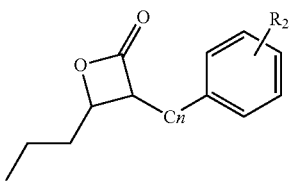

wherein $R_2$ is a single substitution of a hydrogen at any position on the benzene ring where the substituted moiety is selected from the group consisting of alkyl, substituted alkyl, alkynyl, substituted alkyl, vinyl, nitro, halo (e.g., includes bromine, chlorine, fluorine and iodine), cyano, aryl, hetero aryl, alkoxy; and $C_n$ is carbon and n is a number of from 1 to 5.

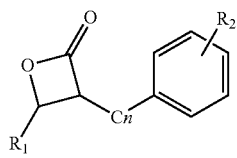

wherein $R_1$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, NH2, NHR, NR2, mono- or polyhydroxy-substituted alkyl, aryl, substituted aryl, heteroaryl, and substituted heteroaryl; $R_2$ is a single substitution of a hydrogen at any position on the benzene ring where the substituted moiety is selected from the group consisting of alkyl, substituted alkyl, alkynyl, substituted alkyl, vinyl, nitro, halo, cyano, aryl, heteroaryl, alkoxy; and, $C_n$ is carbon and n is a number of from 1 to 5. Specific forms of the above structure are provided below:

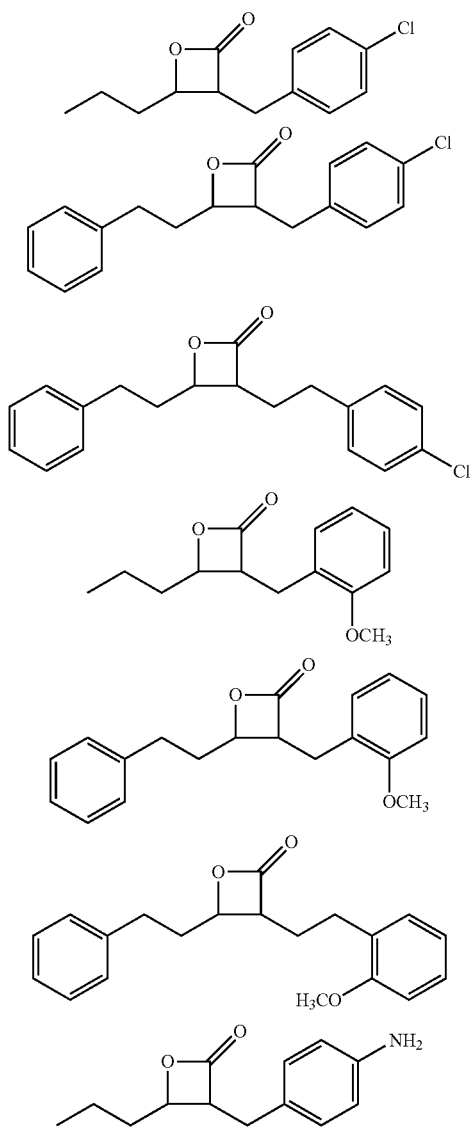

-continued

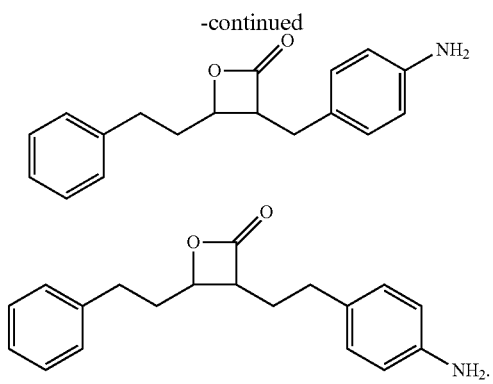

Small molecule phenyl esters have also been shown to inhibit bacterial ClpP. See, e.g., Hackl et al., *J. Am. Chem. Soc.*, 137, 8475-8483 (2015), the disclosure of which is incorporated by reference herein in its entirety and for all purposes. Such small molecule inhibitors include, e.g.:

AV167

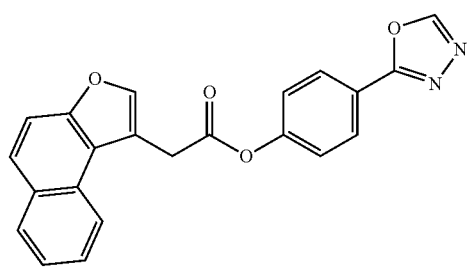

AV170

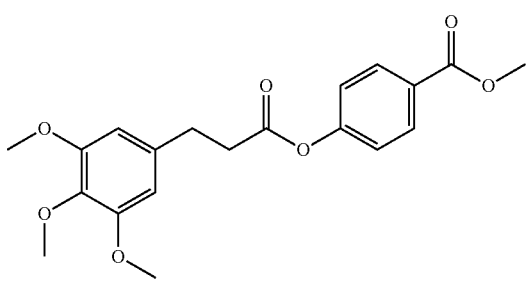

In addition to the compounds described above, pharmaceutically acceptable salts and pro-drugs thereof may be utilized in the methods disclosed herein.

Agent Delivery

In some embodiments, a subject method (e.g., a screening method or a treatment method as described herein) includes a step of administering an agent to an individual (e.g., a test agent, a candidate agent, a ClpP inhibitor that reduces an expression level and/or activity level of ClpP, e.g., an RNAi agent or a gene editing agent that specifically reduces expression of ClpP, and the like). Depending on context, the individual can be of any suitable species (e.g., a mammal, a rodent, a mouse, a rat, a non-human primate, a human, etc.). For example, in some cases a test agent is administered to a mouse. In some cases, a candidate agent (e.g., as identified by a subject screening method) is administered to a mouse, a rat, a non-human primate, or a human (e.g., an individual with obesity, diabetes, reduced insulin sensitivity, reduced glucose tolerance, etc. In some cases, a ClpP inhibitor that reduces an expression level and/or activity level of ClpP as described herein is administered to a mouse, a rat, a non-human primate, or a human.

In some cases, an agent as described herein is administered systemically. In some cases, an agent as described herein is administered locally (e.g., directly to a desired tissue such as the liver). In some cases, an agent as described herein is administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective. In some cases, an agent as described herein is administered via injection. In some cases, an agent as described herein is administered in a tissue-specific manner (e.g., administration is directed to a specific tissue such as the liver).

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

In some embodiments, a single dose of a ClpP inhibitor is administered. In other embodiments, multiple doses of a ClpP inhibitor are administered. Where multiple doses are administered over a period of time, a ClpP inhibitor is administered twice daily (qid), daily (qd), every other day (qod), every third day, three times per week (tiw), or twice per week (biw) over a period of time. For example, a ClpP inhibitor is administered qid, qd, qod, tiw, or biw over a period of from one day to about 2 years or more. For example, a ClpP inhibitor is administered at any of the aforementioned frequencies for one week, two weeks, one month, two months, six months, one year, or two years, or more, depending on various factors.

In some cases, a small molecule inhibitor of ClpP as described herein, e.g., a β-Lactone, such as (3RS,4RS)-3-(non-8-en-1-yl)-4-(2-(pyridin-3-yl)ethyl)oxetan-2-one or a pharmaceutically acceptable salt or pro-drug thereof is administered to a subject in need thereof, e.g., a subject as described herein, in an amount from about 50 mg/kg to about 1000 mg/kg per day, e.g., from about 100 mg/kg to about 900 mg/kg per day, from about 200 mg/kg to about 800 mg/kg per day, from about 300 mg/kg to about 700 mg/kg per day, or from about 400 mg/kg to about 600 mg/kg per day. In some cases, a small molecule inhibitor of ClpP as described herein, e.g., a β-Lactone, such as (3RS,4RS)-3-(non-8-en-1-yl)-4-(2-(pyridin-3-yl)ethyl)oxetan-2-one or a pharmaceutically acceptable salt or pro-drug thereof is administered to a subject as a once daily dose or a twice daily dose.

In some cases, a RNAi agent or genome editing agent is configured such that the reduction of ClpP expression brought about by the agent is limited to a particular tissue type (e.g., the liver). For example, the components of an RNAi agent (e.g., shRNA, siRNA) or genome editing agent (CRISPR/Cas protein plus guide RNA) can be active only in a particular tissue, e.g., the components can be delivered to the particular tissue, the components can be operably linked to a tissue-specific promoter, etc. For example, as described in the examples below, delivery of the Cre recombinase to the liver in mice that harbor a floxed allele of the ClpP gene in their genome, recapitulates the increase in insulin sensitivity exhibited by ClpP knockout mice. Thus, reduction of ClpP expression in the liver can result in an increase in insulin sensitivity without the potential side effects of reducing ClpP expression throughout the whole individual. In some cases, the inhibitor of ClpP that reduces ClpP expression and/or activity (e.g., a small molecule inhibitor, an RNAi agent or gene editing agent specific for ClpP) is administered systemically, and in some cases locally (e.g., to the liver, e.g., see U.S. Pat. Nos. 8,524,679; and 8,008,468, both of which are incorporated by reference in their entirety).

In some cases, the effect of an agent as described herein is substantially liver-specific (e.g., the genome editing nuclease such as Cre recombinase, a CRISPR/Cas endonuclease, a ZFN, a TALEN, etc., can be delivered in a tissue specific manner or can be under the control of a tissue specific promoter). By "substantially liver-specific" it is meant that the majority of the reduction of ClpP expression is in the liver. Such can be achieved in a number of different ways. It is understood that the reduction of ClpP expression may not be limited only to the liver, but that one or more other tissues may exhibit reduction of ClpP expression as well. For example, if a promoter is used (e.g., as part of an expression vector to drive expression of a ClpP inhibitor, e.g., a genome editing nuclease, or a component of a ClpP inhibitor, e.g., a CRISPR/Cas guide RNA), that promoter need not be perfectly limited only to the liver. Such a promoter may exhibit 'leaky' expression in other tissues or may be limited to tissues other than just the liver (e.g., the liver plus one or more additional tissues, but not all tissues, i.e., the promoter is not constitutive). As another example, if an agent is locally delivered (e.g., via direct injection), it is understood that some of the agent may also affect tissues in addition to the liver (e.g., neighboring organs, the blood, etc.). Thus, when the term "substantially liver-specific" is used, it is meant that global ClpP expression (e.g., throughout the whole body) is not reduced, while liver ClpP expression is reduced.

For example, when the agent is an RNAi agent, liver-specificity can be accomplished by delivering the agent directly to the liver (e.g., injection into the liver etc.). On the other hand, liver-specificity can be accomplished by expressing the RNAi agent from a DNA encoding the agent (e.g., an expression vector encoding an shRNA) where the promoter driving expression of the agent drives expression of the agent in the liver (e.g., a liver-specific promoter). Likewise, genome editing agents can be delivered directly to the liver, or can be functional in the liver (e.g., by expressing one or more of the components from an expression vector that has a promoter that drives expression in the liver, e.g., a liver-specific promoter). In some cases, the inhibitor of ClpP is administered such that reduction of ClpP expression is substantially liver-specific, and the amount administered is effective for increasing insulin sensitivity of the individual.

Liver-specificity can also be accomplished when the inhibitor of ClpP that reduces ClpP expression and/or activity is in an inactive form unless converted to an active form by a liver-specific enzyme. For example, the inhibitor of ClpP can be delivered in the form of a prodrug, which is then converted to an active form in the liver, for example by a carboxylesterase such as human liver carboxylesterase 1 (hCE1), a paraoxonase such as PON3, an alkaline phosphatase, human valacyclovirase (VACVase), a purine-nucleosidephosphorylase (PNP), and the like). See, e.g., Yang, et. al., *Enzyme-mediated hydrolytic activation of prodrugs*, Acta PharmaceuticaSinica B 2011; 1(3):143-159.

Agents can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. Subject agents can be administered in the form of a depot injection or implant preparation which can be formulated in such a manner as to permit a sustained or pulsatile release of the active ingredient. The agents can be formulated as sterile, substantially isotonic and are in full compliance with all Good Manufacturing Practice (GMP) regulations of the U.S. Food and Drug Administration.

Also within the scope of the disclosure are kits. For example, in some cases a subject kit can include (i) a detection reagent for detecting a ClpP activity level and/or expression level (e.g., protein, mRNA), e.g., an anti-ClpP antibody, and (ii) a control agent (e.g. a positive control agent that is known to reduce a ClpP activity level and/or expression level, and/or a negative control agent that is known not to reduce a ClpP activity level and/or expression level). In some cases, a subject kit can include instructions for use. Kits typically include a label indicating the intended use of the contents of the kit. The term label includes any writing, or recorded material supplied on or with the kit, or which otherwise accompanies the kit.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-26 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of identifying a candidate agent for treating obesity, liver disease, and/or diabetes, the method comprising:
   (a) contacting a mammalian cell with a test agent;
   (b) measuring the expression level and/or activity level of ClpP in the mammalian cell relative to a reference value following the contacting;
   (c) determining that the test agent caused a decrease in the expression level and/or activity level relative to the reference value; and
   (d) identifying the test agent as a candidate agent for treating obesity, liver disease, and/or diabetes.
2. The method according to 1, wherein the mammalian cell is a mouse cell.
3. The method according to 1, wherein the mammalian cell is a human cell.
4. The method according to any of 1-3, wherein the mammalian cell is in vitro.
5. The method according to any of 1-3, wherein the mammalian cell is ex vivo.
6. The method according to any of 1-3, wherein the mammalian cell is in vivo.
7. The method according to any of 1-6, wherein the mammalian cell is a hepatocyte.
8. The method according to 2, wherein the contacting comprises administering the test agent to a mouse.
9. The method according to 8, further comprising, measuring an expression level and/or activity level of ClpP in the mouse prior to the contacting of step (a) in order to obtain the reference value.

10. The method according to any of 1-9, further comprising, after step (d), administering the identified candidate agent to an individual that has obesity, liver disease, and/or diabetes.
11. The method according to 10, wherein the individual is a mouse, a non-human primate, or a human.
12. The method according to 10 or 11, further comprising, after administering the identified candidate agent to the individual, measuring one or more features of the individual selected from: insulin sensitivity, blood glucose level, glucose tolerance, body fat mass, an amount of fat tissue, an amount of white adipose tissue; percent fat mass, body weight, visceral adipose adipocyte size, plasma leptin level, growth hormone level, basal energy expenditure, a level of phosphorylated AKT (p-AKT) in muscles and/or fibroblasts, percent lean mass, mitochondrial number in hepatocytes, mitochondrial mass in hepatocytes, mitochondrial morphology in hepatocytes, fibroblast respiratory capacity, fibroblast maximal oxygen consumption rate (OCR), and fibroblast resistance to $H_2O_2$-induced cytotoxicity.
13. The method according to any of 1-12, wherein in the test agent is a small molecule or a polypeptide.
14. The method according to any of 1-13, comprising measuring an expression level of ClpP, wherein the expression level is an RNA expression level and the measuring comprises the use of quantitative RT-PCR, a microarray, or RNA sequencing.
15. The method according to any of 1-13, comprising measuring an expression level of ClpP, wherein the expression level is a protein expression level and the measuring comprises detecting ClpP protein using an anti-ClpP antibody, mass spectrometry, and/or an enzyme-linked immunosorbent assay (ELISA) assay.
16. The method according to any of 1-13, comprising measuring a decrease in an activity level of ClpP by measuring an increase in an amount of one or more proteins selected from: TNF receptor-associated protein 1 (TRAP1), heat shock protein family A (Hsp70) member 9 (Grp75), leucine rich pentatricopeptide repeat containing (LRPPRC), caseinolytic mitochondrial matrix peptidase chaperone subunit (ClpX), ornithine aminotransferase (OAT), and Ion peptidase 1(LonP1).
17. The method according to any of 1-16, wherein the method comprises screening a plurality of test agents to identify one or more candidate agents for treating obesity, liver disease, and/or diabetes.
18. A method of treating an individual with obesity, liver disease, and/or diabetes, the method comprising:
    administering an inhibitor of ClpP to the individual in an amount effective for decreasing an amount of fat tissue in the individual, preventing or reducing weight gain of the individual, increasing insulin sensitivity of the individual, and/or increasing glucose tolerance of the individual.
19. The method according to 18, wherein the inhibitor of ClpP is an RNAi agent or a gene editing agent that specifically reduces expression of ClpP.
20. The method according to 18 or 19, wherein the inhibitor of ClpP is administered such that reduction of ClpP expression is substantially liver-specific, and the amount administered is effective for increasing insulin sensitivity of the individual.
21. The method according to 18, wherein the inhibitor of ClpP is a small molecule.
22. The method according to 21, wherein the small molecule is a β-Lactone.
23. The method according to 22, wherein the β-Lactone is (3RS,4RS)-3-(non-8-en-1-yl)-4-(2-(pyridin-3-yl)ethyl) oxetan-2-one or a pharmaceutically acceptable salt thereof.
24. The method according to any of 18-23, wherein the inhibitor of ClpP is delivered directly to the individual's liver, and the amount administered is effective for increasing insulin sensitivity of the individual.
25. The method according to any of 18-24, wherein the administering comprises local injection.
26. The method according to any of 18-25, further comprising a step of measuring insulin sensitivity of the individual.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of the invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Materials and Methods

The following methods were utilized in the examples described herein:

Animals. All mice were maintained on a 12-h light/dark cycle in a pathogen-free animal facility. Mice were separately housed by their genotypes for all metabolic studies. For high-fat diet (HFD)-induced obesity studies, animals were fed a HFD (21% by weight, 42% kcal from fat, 0.2% total cholesterol; TD.01064, Harlan-Teklad) for specified periods. Anesthesia was induced with isoflurane (survival procedures) or with avertin (terminal procedures). All procedures were approved by the UCSF Animal Research Committee and followed NIH guidelines. Animal sample sizes for different assays were chosen based on previous literature. Animals were grouped according to genotype; no randomization was used. For all behavior tests, all animal IDs were blinded to tester. Testers were not blinded for other assays.

Generation and maintenance of ClpP knockout (ClpP$^{-/-}$) and ClpP conditional knockout (ClpP-cKO) mice. Frozen ClpP$^{+/-}$ sperm was recovered and ClpP$^{+/-}$ mice were generated. ClpP$^{-/-}$ mice were back-crossed into a C57BL/6 genetic background for three or more generations. Since ClpP$^{-/-}$ mice were infertile, ClpP$^{+/-}$ mice were bred with each other to generate littermates with three different genotypes (WT, ClpP$^{+/-}$, ClpP$^{-/-}$) and used to maintain the line.

Generation and maintenance of ClpP conditional knockout (Clp-cKO) mice. A ClpP-cKO construct was made by flanking ClpP gene with a long arm of homology (5' terminal, about 6 Kb) and a short arm of homology (3' terminal, about 3 Kb). LoxP sites were added to both ends of the region containing ClpP exons 1-3 for future removal. A puromycin resistant gene flanked by F3 sites were inserted right before the 3' terminal loxP site. A mouse ES cell clone carrying the targeted ClpP allele was selected and used for microinjection. Resulting chimeras were bred with Flp mice to generate offspring carrying the targeted ClpP allele. Heterozygous ClpP-cKO mice were then bred to generate homozygous ClpP-cKO mice. The ClpP-cKO mice were generated on a C57BL/6 genetic background. Homozygous ClpP-cKO mice were used to maintain the line.

Body composition analysis. Body composition of mice after a 4-h fast was analyzed under isoflurane anesthesia by dual-energy X-ray absorpitometry (DEXA) with a PIXImus2 scanner (GE Healthcare Lunar).

Food intake study. Mice were separately housed by their genotypes. For each cage, food was weighted every day at 10:00 a.m. for 4 days. The daily food intake for each cage was calculated by subtracting the food weight at the end of a 24-h period from the food weight at the starting time. The daily food intake is normalized by either animal number or body weight.

Fasting-refeeding study. Mice fasted for 24 h and then returned to free feeding. The body weights of mice were measured before and after the fasting. The food intake and body weight gain were monitored after refeeding periods of 8 and 24 h.

Body temperature measurement. The core body temperatures of mice were taken with a rodent rectal thermometer.

Measurement of blood glucose and plasma insulin. Blood glucose was measured with a glucometer and glucose test strips (Free Style Lite). Plasma insulin was quantified with an insulin Elisa kit (Crystal Chem).

Glucose, insulin, and pyruvate tolerance tests. Glucose, insulin, and pyruvate tolerance tests were performed by intraperitoneal injection of glucose (2 g/kg), insulin (0.5 units/kg) or pyruvate (2 g/kg) after an overnight fast for glucose and pyruvate or a 4-h fast for insulin. Blood glucose levels were measured before injection and at different time points after injection. To assess glucose-stimulated insulin release, mice fasted overnight (for 16 h) and were then injected intraperitoneally with glucose (2 g/kg). Blood samples were collected from tail veins before injection and at different time points after injection.

Behavior tests. The general neurological behavior profiles of ClpP$^{-/-}$ mice were assessed by the grip strength, incline, and tail suspense tests. The motor function of these mice was determined by the rotarod test. Anxiety levels were determined by elevated plus maze. Activity levels were studied by an open field test. The learning and memory of these mice were examined using the Morris water maze. The auditory functions were tested by prepulse inhibition test.

Histological analysis. Tissues (liver, visceral adipose, gastrocnemius muscle, interscapular brown adipose, and pancreas) were fixed in 4% paraformaldehyde (pH 7.4) overnight, embedded in paraffin, and serially sectioned at 7-8 μm. Standard haematoxylin and eosin staining was performed.

Adipocyte size measurement. Haematoxylin and eosin staining of adipose tissue sections was performed and images were analyzed with image J.

Electron microscopic analysis of liver sections. WT or ClpP$^{-/-}$ mice were perfused with EM fixative. The liver tissues were collected and fixed in the EM fixative for 2 days. The tissues were processed and electron microscopy images were collected using a JEOL JEM-1230 transmission electron microscope. The mitochondrial number, area, and roundness were measured by Image J software at 13,600 magnifications.

Generation of adipocyte-specific ClpP-cKO mice. Adipocyte-specific ClpP knockout mice were generated through breeding ClpP-cKO mice with ap2Cre mice. The Cre$^+$ mice had greatly reduced ClpP protein levels in adipose tissues and the Cre-littermates were served as controls in metabolic assays.

Tail vein injection of AAV-CMV-Cre. AAV8.2-CMV-Cre and control AAV8.2 were utilized. These viruses were injected into 3-5 month-old ClpP-cKO mice through tail vein at a dose of 5×10$^9$ genome copies/gram (gc/gram) body weight. The body weights of the injected mice were measured once every week. The blood glucose and plasma insulin levels were measured before and 3 weeks after injection. The glucose tolerance test was performed on these mice 4 weeks after injection. HFD was given to these mice 6 weeks after injection. The body weight gain in response to HFD was followed and the glucose tolerance test was performed after two weeks on HFD.

Western blot. Tissues or cells were lysated in low-detergent buffer (50 mM Tris/HCl, pH 8.0, 150 mM NaCl, 0.1% SDS, 0.5% Nonidet P-40, 0.5% sodium deoxycholate) with a mixture of protease inhibitors. Phosphatase inhibitors were also included in the lysate buffer. The lysates were centrifuged at 13,000 rpm for 10 min to remove the pellets. SDS-PAGE was performed with a NuPAGE bis-tris system from Invitrogen, following the vendor's protocol. A standard western blot protocol was used with IRDye-labeled secondary antibodies (Li-cor). A Li-cor image system was used to scan the western blot images.

2D fluorescence difference gel electrophoresis. Organs from ClpP$^{-/-}$, ClpP$^{+/-}$, or WT mice were submitted for 2D fluorescence difference gel electrophoresis analysis. The most dramatically changed spots were cut from the gel for mass spectrometry analysis to identify the proteins, which was done by the same company.

Mouse fibroblast preparation. Mouse fibroblasts were prepared from skin tissue collected from new-born pups. The tissue was cut into small pieces and placed on a 100-mm cell culture dish with the skin side up. After 5-10 min, 10 ml of fibroblast medium (DMEM with 10% FBS) was slowly added to the dishes. The implants were cultured in a humidified 37° C., 5% CO$_2$ incubator. Fibroblasts eventually proliferated after 7-10 day in culture. Mouse fibroblasts were maintained in the same medium for multiple passages.

Overexpression of ClpP in ClpP$^{-/-}$ fibroblasts. Lentiviral overexpression vector for human ClpP was constructed with pLenti7.3TOPO TA Cloning Kit from Life Technologies. The lentiviruses were packed with ViraPower™ lentiviral packaging mix from Life Technologies. Lentivirus carrying either empty vector (control) or human ClpP cDNA were added to ClpP−/− fibroblasts and incubated for 48 hr before further experiments.

shRNA knockdown of different genes in ClpP$^{-/-}$ fibroblasts. Lentiviral shRNA constructs were obtained. The lentiviruses were packed with ViraPower™ lentiviral packaging mix from Life Technologies. Lentivirus carrying either empty vector (control) or different shRNAs were added to ClpP$^{-/-}$ fibroblasts and incubated for 48 hr before further experiments.

Cell viability assay. Mouse fibroblasts were plated on black clear-bottomed 96-well plates at 10,000 cells per well. After incubating for 24 h, the cells were cultured in OPTI-MEM medium overnight. The cells were treated with $H_2O_2$ at various doses for 4 h. Alamar blue reagent (Invitrogen) was then added to the wells (1:10 ratio). After a 2-h incubation, the fluorescence intensity was measured at 590 nm emission (560 nm excitation).

Seahorse OCR assay. Mouse fibroblasts were maintained in fibroblast growth medium until confluence. The day before the assay, fibroblasts were trypsinized and plated on a 96-well Seahorse culture plate at 40,000 cells per well. Before the assay, the culture medium was changed to a $CO_2$-independent medium supplied by Seahorse Bioscience. The cells were then incubated at 37° C. without $CO_2$ for 0.5-1 h. The oxygen consumption rate (OCR) assay was performed with an XF Cell mito-stress test kit and XF Extracellular Flux Analyzers (Seahorse Bioscience) following the vendor's protocol.

Growth hormone (GH) and leptin level determination. The GH and leptin levels in mouse plasma were determine by a mouse GH ELISA kit and ultra sensitive mouse insulin ELISA kit from Crystal Chem, Inc.

Antibodies. The antibodies used were anti-ClpP (rabbit, Novus Biologicals), anti-ClpX (SDI, custom made), anti-Akt (rabbit, Cell Signaling), anti-phospho-Akt (rabbit, Cell Signaling), anti-Grp75 (rabbit, Cell Signaling), anti-TRAP1 (moue mAb, AbCam), anti-LRPPRC (rabbit, Proteintech Group), anti-LonP (rabbit, Sigma-Aldrich), anti-OAT (mouse, Abcam), anti-SDH2 (rabbit, aric antibodies), anti-ATP6V1A (rabbit, Proteintech Group), anti-CPS1 (mouse, Lifespan), anti-Hsp70 (rabbit, Cell Signaling), anti-GAPDH (mouse mAb, Millipore), anti Hsp60 (rabbit, Abcam), anti-VDAC (mouse mAb, EMD Chemical), and anti-actin (rabbit, Sigma-Aldrich).

Statistical analyses. Data are presented as mean±SD unless otherwise specified. All statistical analyses were done using Prism 6 software (GraphPad). Differences between means were assessed by t-test, one-way ANOVA, or repeated measures ANOVA, followed by Bonferroni or Tukey-Kramer post hoc tests. In all cases, P<0.05 was considered statistically significant.

Mammalian ClpXP, an ATPase complex consisting of the catalytic subunit ClpP and the regulatory subunit ClpX, is a mitochondrial protease with unclear physiological functions. The data presented in the following examples show that ClpP knockout (ClpP$^{-/-}$) mice expended more energy and had reduced adipose tissue and enhanced insulin sensitivity compared to wild type controls. Drastic increases in mitochondrial chaperones were detected in various organs of ClpP$^{-/-}$ mice, accompanied with increased mitochondrial numbers. Eliminating ClpP increased mitochondrial function and anti-stress capacity of cells by elevating LRPPRC and/or TRAP1 levels (both of which are proteins with roles in mitochondrial function), which were reversed by knocking down either protein. Hepatic ClpP was responsible for regulating insulin sensitivity while adipocytic ClpP was not. Thus, ClpP is a master regulator of mitochondrial function and stress response, which in turn modulate energy homeostasis, lipid storage, and insulin sensitivity. These data highlight ClpP as a therapeutic target for treating obesity and diabetes.

Example 1

Absence of ClpP in Mice Reduced Adipose Tissue on a Chow or High Fat Diet

Figure 7:
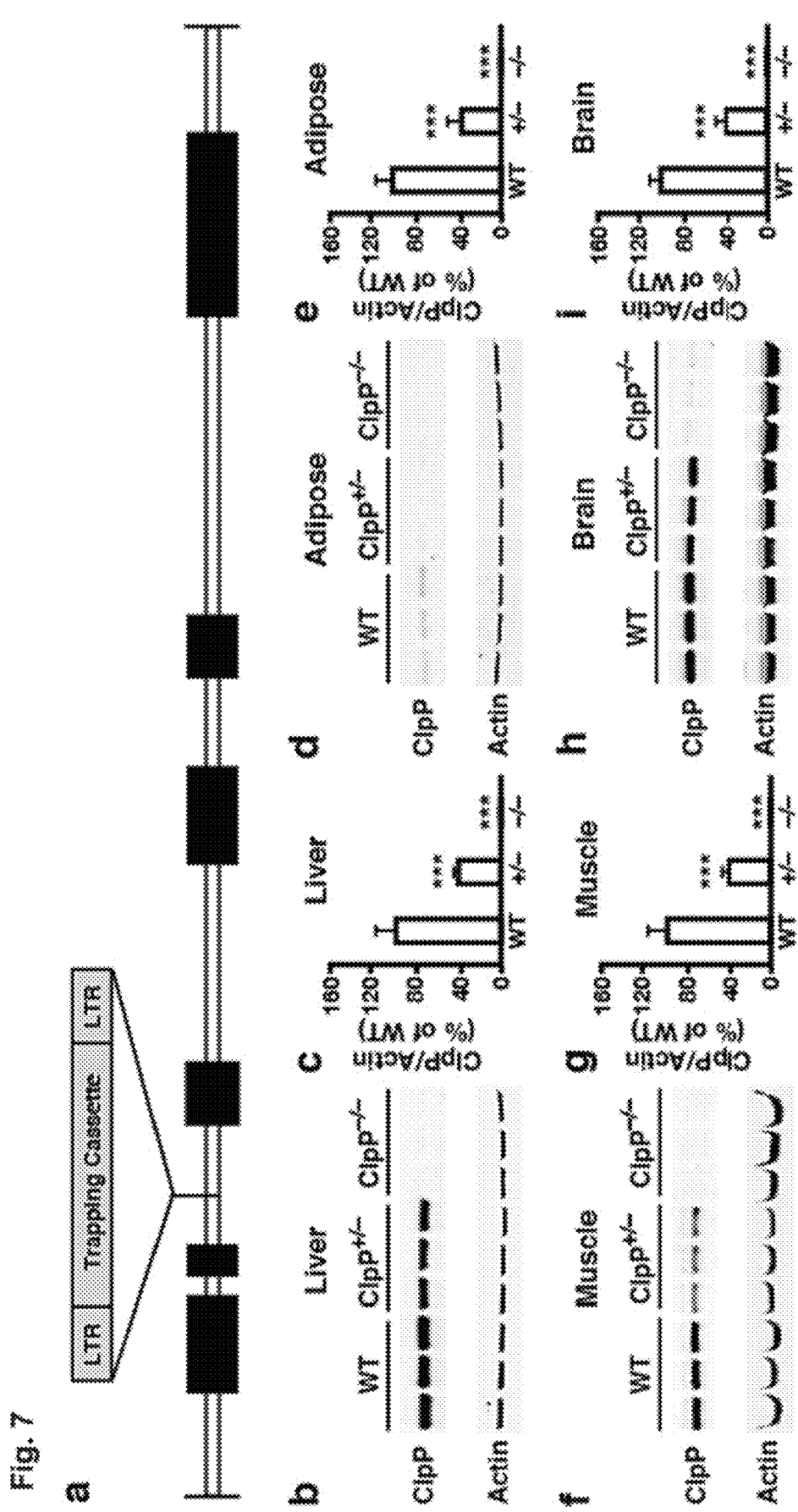
FIG. 7 (panels a-i) provide data showing the generation of ClpP$^{-/-}$ mice.
Figure 8:
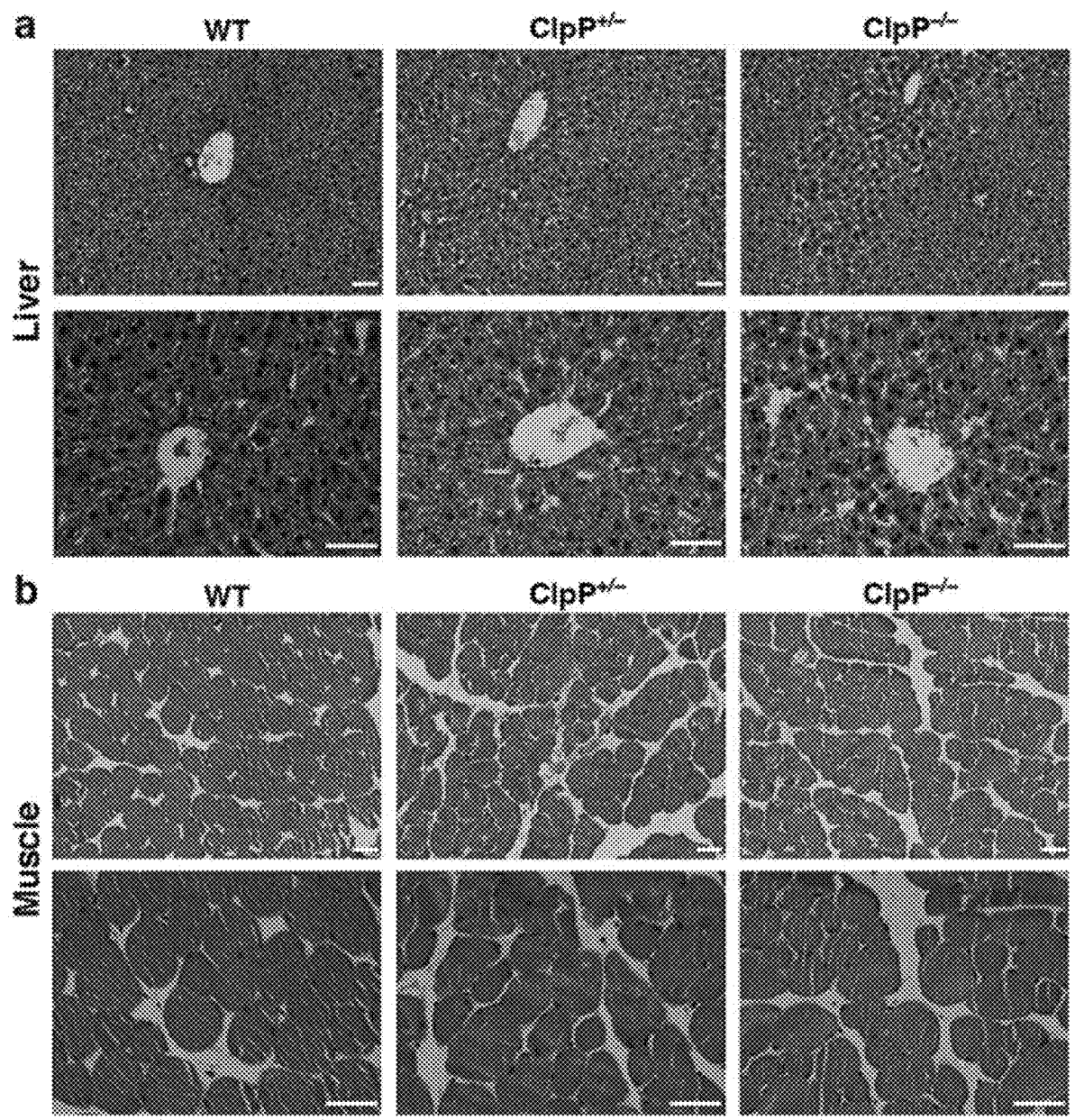
FIG. 8 (panels a-b) provide data showing that ClpP$^{-/-}$ mice have normal histology of the liver and muscle.
Figure 9:
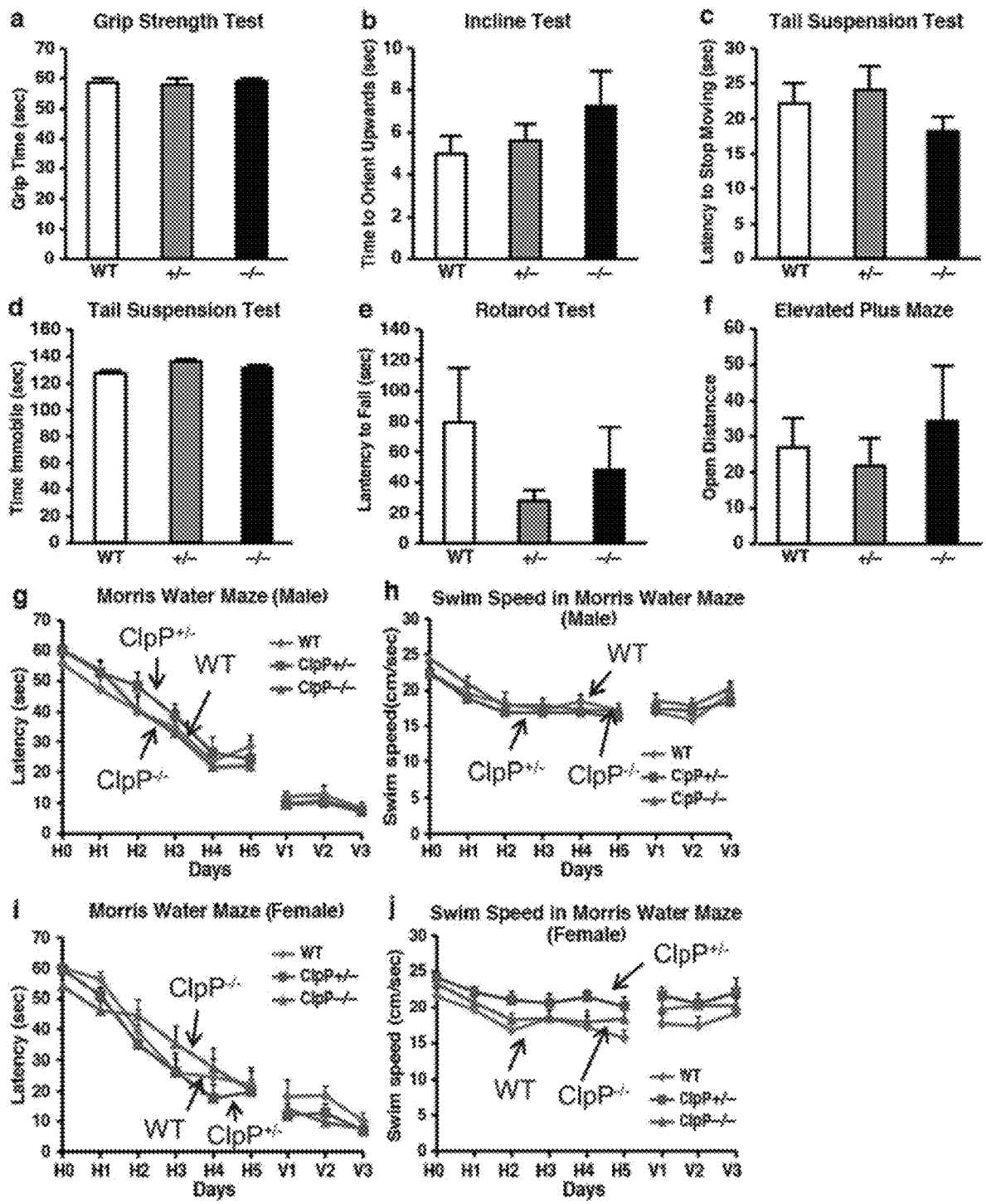
FIG. 9 (panels a-j) provide data showing that ClpP$^{-/-}$ mice have normal neurological profile.

To understand the physiological roles of mammalian ClpXP protease, a ClpP knockout (ClpP$^{-/-}$) mouse model was generated through a gene-trapping strategy (FIG. 7, panel a). Quantitative polymerase chain reaction (qPCR) (not shown) and western blotting confirmed that the Clpp gene was efficiently deleted in different organs (FIG. 7, panels b-i). ClpP$^{-/-}$ pups were born viable and at normal Mendelian ratios. Morphological assessment of liver and muscle revealed no abnormalities in 6-month-old homozygous (ClpP$^{-/-}$) or heterozygous (ClpP$^{+/-}$) knockout mice (FIG. 8). There were no differences between ClpP$^{-/-}$ and WT littermates in general neurological behavior, motor function (rotarod and swim speed tests), anxiety (elevated plus maze test), or learning and memory (Morris water maze test) (FIG. 9), indicating a normal neurological profile.

However, both male and female adult ClpP$^{-/-}$ mice were significantly smaller in weight and size than WT and ClpP$^{+/-}$ littermates (FIG. 1, panels a-b). In contrast, all new-born pups had similar body weights regardless of their ClpP genotypes (FIG. 1, panel c). In addition, growth hormone levels in 5-6-month-old ClpP$^{-/-}$ mice were higher than in other groups of mice (ClpP$^{-/-}$, 8.54±5.41 ng/ml; ClpP$^{+/-}$, 2.48±0.67 ng/ml; WT, 0.91±0.53 ng/ml; n=3-5 mice for each genotype; one way ANOVA, p=0.0053), so body weight differences in adults did not stem from early developmental defects or growth hormone deficiencies.

Figure 10:
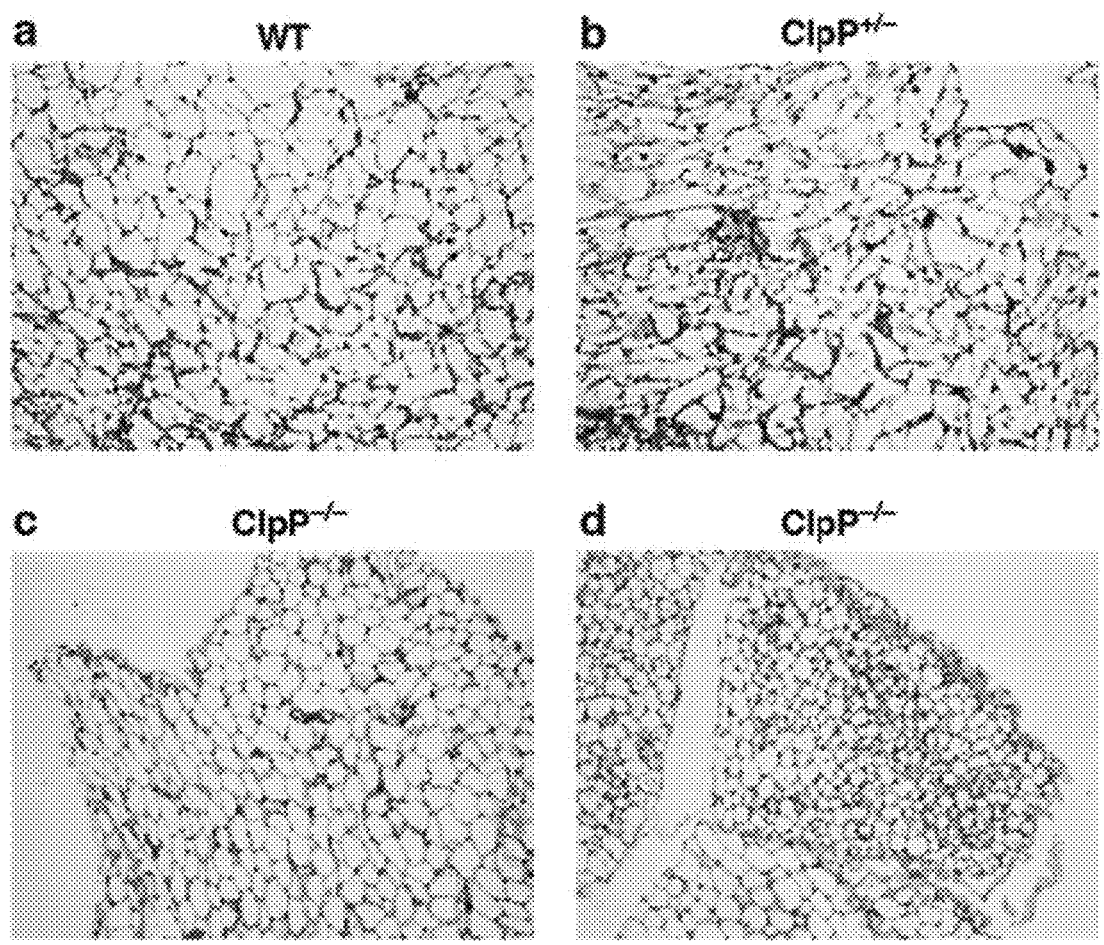
FIG. 10 (panels a-d) provide data showing that ClpP$^{-/-}$ mice have smaller adipocytes.
Figure 11:
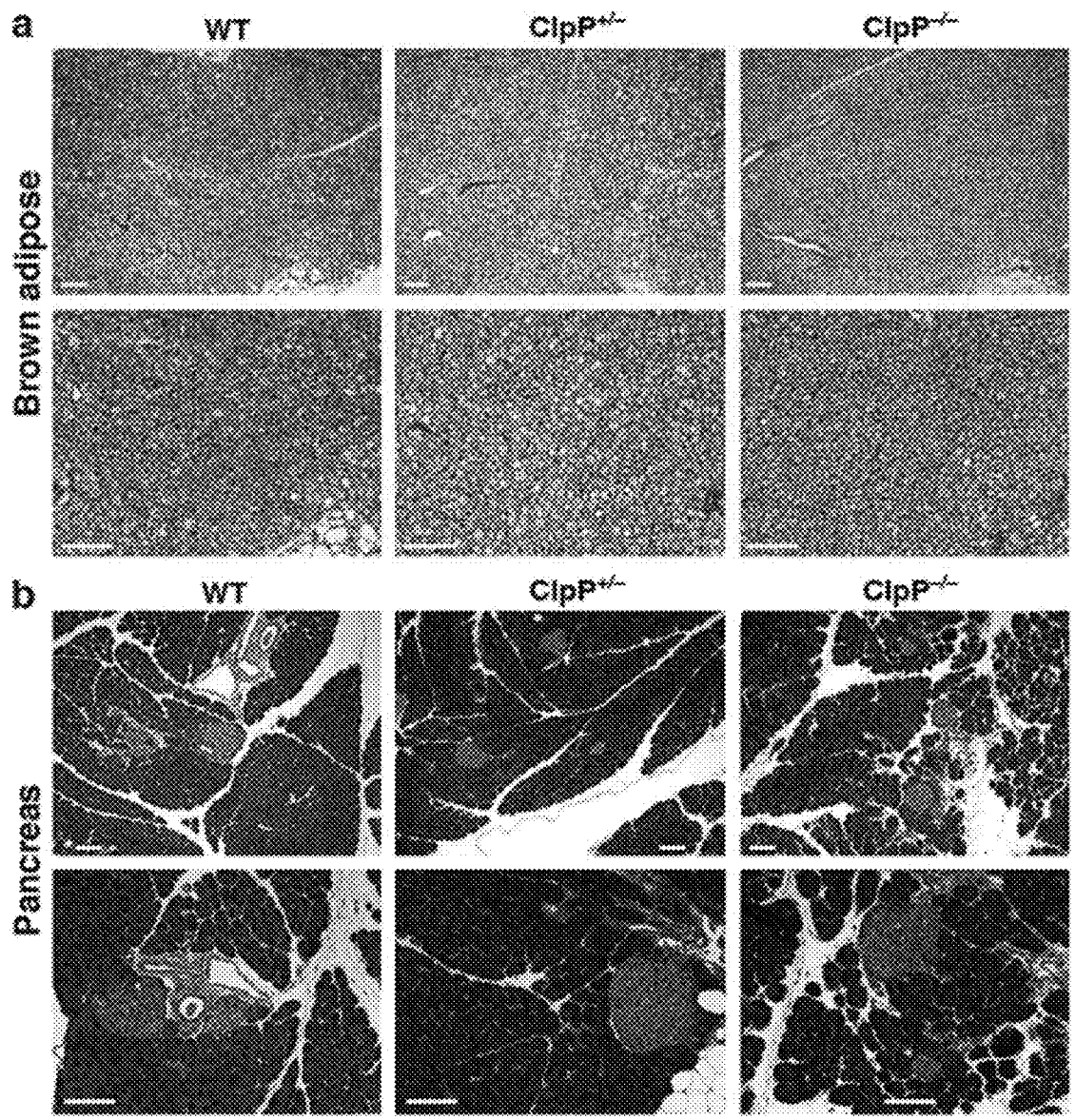
FIG. 11 (panels a-b) provide data showing that ClpP$^{-/-}$ mice have normal histology of brown adipose tissue and pancreas.

ClpP$^{-/-}$ mice had dramatically lower body fat, as measured by total body fat mass or body fat content (% fat mass) (FIG. 1, panels d-e), than WT mice. Although ClpP$^{+/-}$ mice had similar body weight to WT mice, they tended to have lower body fat (FIG. 1, panels d-e). In contrast, the lean content (% lean mass) of ClpP$^{-/-}$ mice was significantly higher than that of ClpP$^{+/-}$ and WT mice (FIG. 1, panel g), although the lean mass was significantly lower (FIG. 1, panel f). Interestingly, quantification of interscapular brown adipose tissue, which is critical in thermogenesis and beneficial in metabolic regulation, showed a similar profile as lean tissue among three ClpP genotypes (FIG. 1, panels h-i). Consistent with their lower body fat content, visceral adipose from ClpP$^{-/-}$ mice had smaller adipocytes compared to those from ClpP$^{+/-}$ and WT mice (FIG. 1, panel m, and FIG. 10). In contrast, the morphology of brown adipose tissue in ClpP$^{-/-}$, ClpP$^{+/-}$, and WT mice were similar (FIG. 11, panel a). Thus, knocking out ClpP greatly reduces white adipose tissue, which likely contributes to the lower body weights seen in adult ClpP$^{-/-}$ mice.

Figure 12:
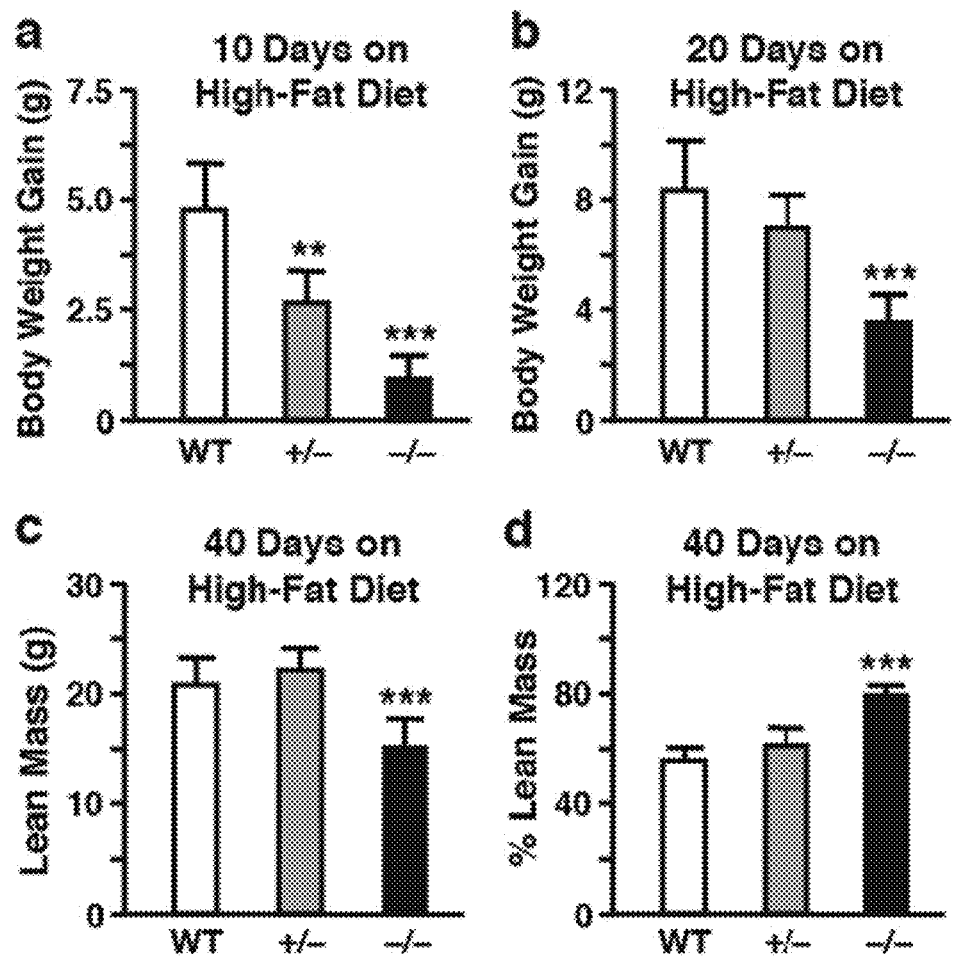
FIG. 12 (panels a-d) provide data showing that ClpP$^{-/-}$ mice are resistant to high-fat diet (HFD)-induced obesity.

Next, mice were fed a high-fat diet (HFD) for 2 months to determine the effect of eliminating ClpP on HFD-induced obesity. ClpP$^{-/-}$ mice were resistant to HFD-induced weight gain, and ClpP$^{+/-}$ mice showed delayed weight gain within the first 10 days (FIG. 1, panel j, and FIG. 12, panel a). At 40 days on the HFD, when body weight changes in all three groups had plateaued, ClpP$^{-/-}$ mice showed only a small increase in fat mass and body weight, while ClpP$^{+/-}$ and WT mice gained significantly more (FIG. 1, panel k, Fig., 1, panel l). Thus, ClpP$^{-/-}$ mice are resistant to HFD-induced obesity. HFD did not change the differences in lean mass and content among various groups of mice (comparing FIG. 1, panels f-g, with FIG. 12, panels c-d).

Also consistent with lower body fat content, ClpP$^{-/-}$ mice had much lower levels of plasma leptin than other groups of mice (ClpP$^{-/-}$, 0.409±0.224 ng/ml; ClpP$^{+/-}$, 1.927±1.928 ng/ml; WT, 2.056±2.022; n=11-12 mice at 5-6 months of age; one way ANOVA, p<0.05). Interestingly, ClpP$^{-/-}$ mice were infertile, as observed in leptin depleted animal models. While not intending to be bound by any particular theory, it is possible that low leptin levels are responsible for the reproductive defect in ClpP$^{-/-}$ mice.

Example 2

Absence of ClpP in Mice Altered the Energy Expenditure Profiles

Figure 2:
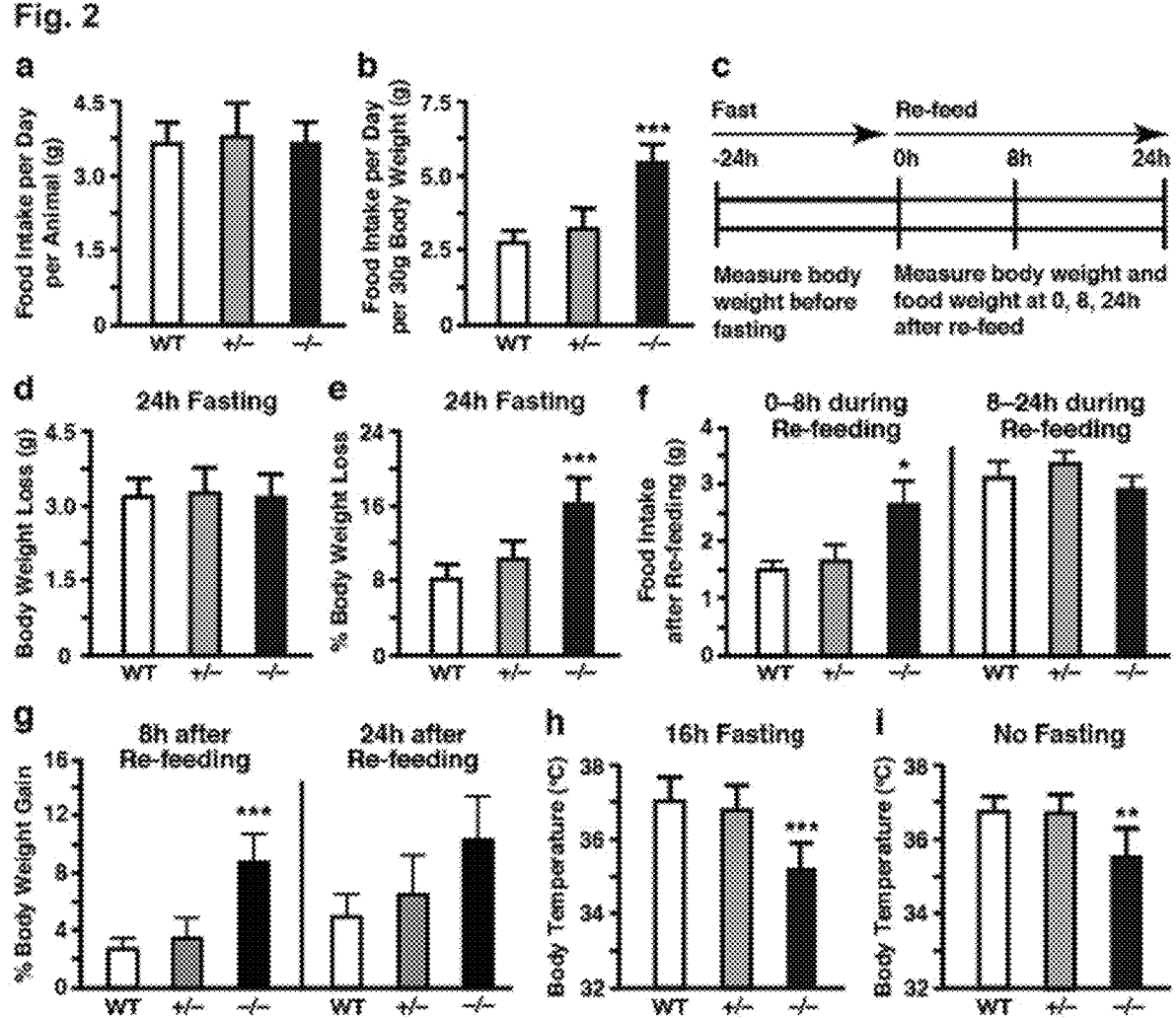
FIG. 2 (panels a-i) provide data showing that ClpP$^{-/-}$ mice had altered whole-body energy expenditure.

Low leptin levels lead to feeding behavior and adipose deposition in WT mice. Consistent with lower serum leptin levels, the food intake normalized to body weight was significantly higher in ClpP$^{-/-}$ mice than in WT and ClpP$^{+/-}$ mice (FIG. 2, panel b), although mice in all groups had similar food intake per animal per day (FIG. 2, panel a). Thus, ClpP$^{-/-}$ mice gained less weight and generated less fat while consuming more food, suggesting that they either expended more energy or did not utilize nutrition properly.

A fasting-refeeding approach was used to dissect these two possibilities (FIG. 2, panel c). After 24 h of fasting, ClpP$^{-/-}$ mice lost the same amount of weight as WT and ClpP$^{+/-}$ mice (FIG. 2, panel d). Since ClpP$^{-/-}$ mice had lower body weight, their percentage of body weight loss was significantly higher than that of WT and ClpP$^{+/-}$ littermates (FIG. 2, panel e), suggesting that ClpP$^{-/-}$ mice expend more energy. During the refeeding period, ClpP$^{-/-}$ mice consumed significantly more food and gained a significantly higher percentage of weight compared with WT and ClpP$^{+/-}$ littermates (FIG. 2, panels f-g).

Figure 13:
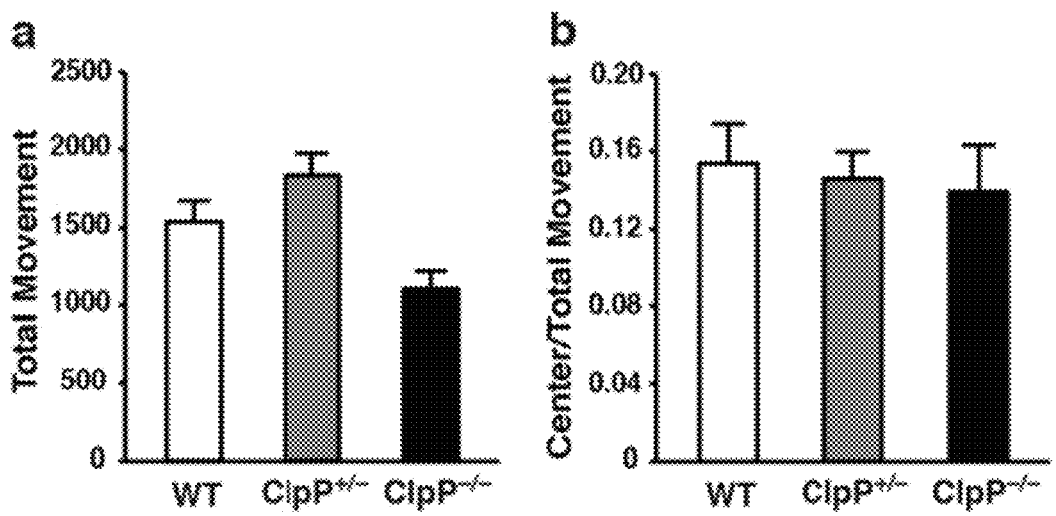
FIG. 13 (panels a-b) provide data showing that ClpP$^{-/-}$ mice have normal locomotor activities.

Higher energy consumption may be attributable to hyperactivity or high thermogenesis. The open field test showed similar activity levels among all groups (FIG. 13). Surprisingly, the core body temperature was significantly lower in ClpP$^{-/-}$ mice than in WT and ClpP$^{+/-}$ mice (FIG. 2, panels h-i), suggesting that ClpP$^{-/-}$ mice did not use more energy for thermogenesis. Thus, it is likely that the ClpP$^{-/-}$ mice had higher basal energy expenditure.

Example 3

Absence of ClpP in Mice Improved Insulin Sensitivity

Figure 3:
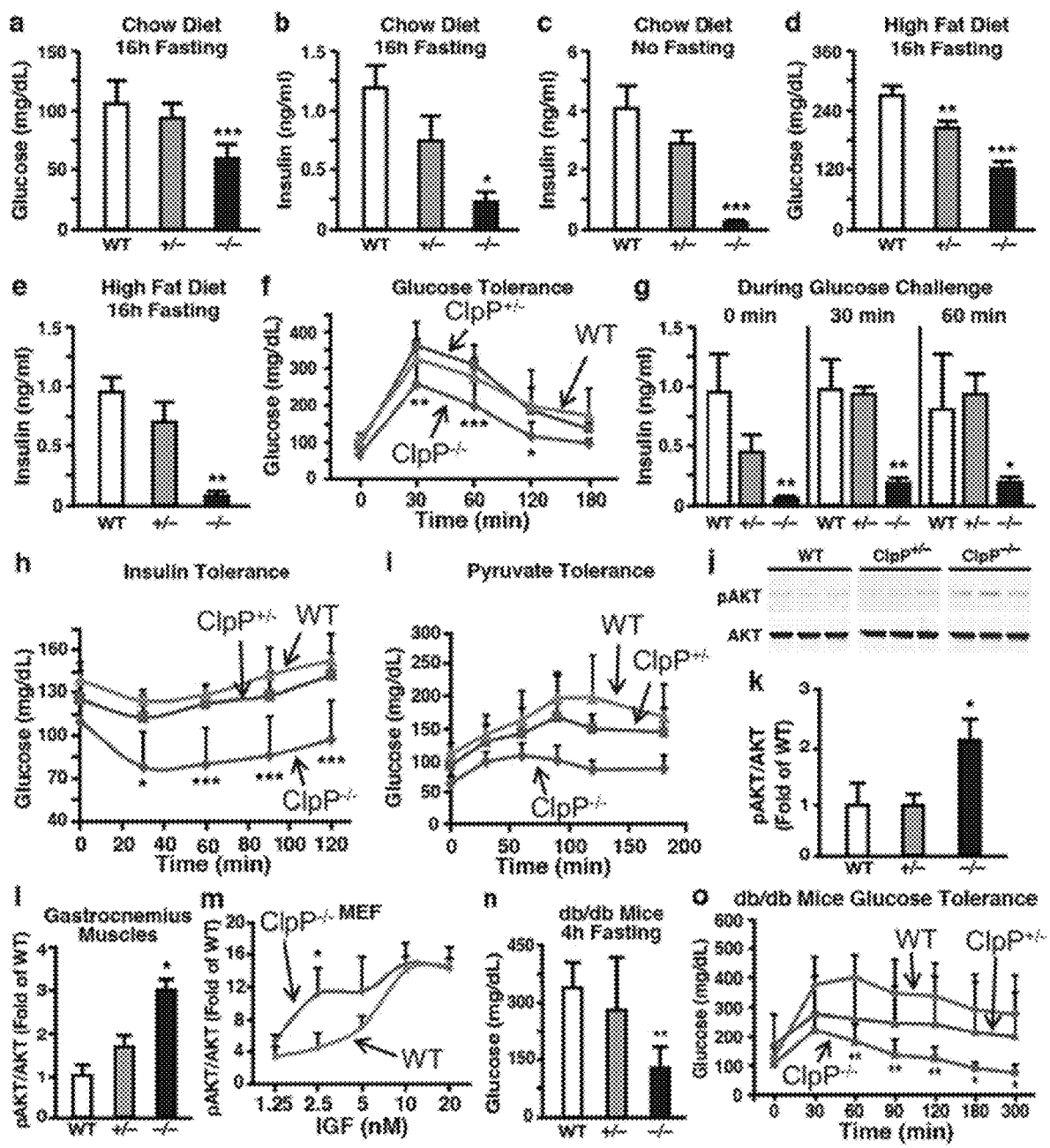
FIG. 3 (panels a-o) provide data showing that ClpP$^{-/-}$ mice had increased insulin sensitivity.

Blood glucose levels and plasma insulin levels in ClpP$^{-/-}$ mice were analyzed. Blood glucose levels were significantly lower in ClpP$^{-/-}$ mice than in ClpP$^{+/-}$ and WT mice (FIG. 3, panel a). Plasma insulin levels were also significantly lower in ClpP$^{-/-}$ mice than in WT controls, with those in ClpP$^{+/-}$ mice being in the middle, under both free-feeding and fasting conditions (FIG. 3, panels b-c). The low insulin levels were unlikely due to a pancreas deficit, based on the morphological data (FIG. 11, panel b). Thus, ClpP$^{-/-}$ mice maintained normal blood glucose levels in spite of having very low insulin levels. After 2 months on HFD, blood glucose levels in WT and ClpP$^{+/-}$ mice increased greatly. In contrast, ClpP$^{-/-}$ mice maintained much lower blood glucose and insulin levels on HFD (FIG. 3, panels d-e). Glucose and insulin tolerance tests further revealed enhanced insulin sensitivity in ClpP$^{-/-}$ mice (FIG. 3, panels f-h). A trend toward increased pyruvate tolerance in ClpP$^{-/-}$ mice was detected, although not reaching significance (FIG. 3, panel i). In support of increased insulin sensitivity, higher p-AKT levels, a main component of the insulin signaling pathway, were found in muscles and fibroblasts of ClpP$^{-/-}$ mice (FIG. 3, panels j-l). Additionally, ClpP$^{-/-}$ fibroblasts were more sensitive than WT fibroblasts to IGF-induced AKT activation in culture (FIG. 3, panel m). These data strongly support the conclusion that eliminating ClpP improves insulin sensitivity in mice.

Figure 14:
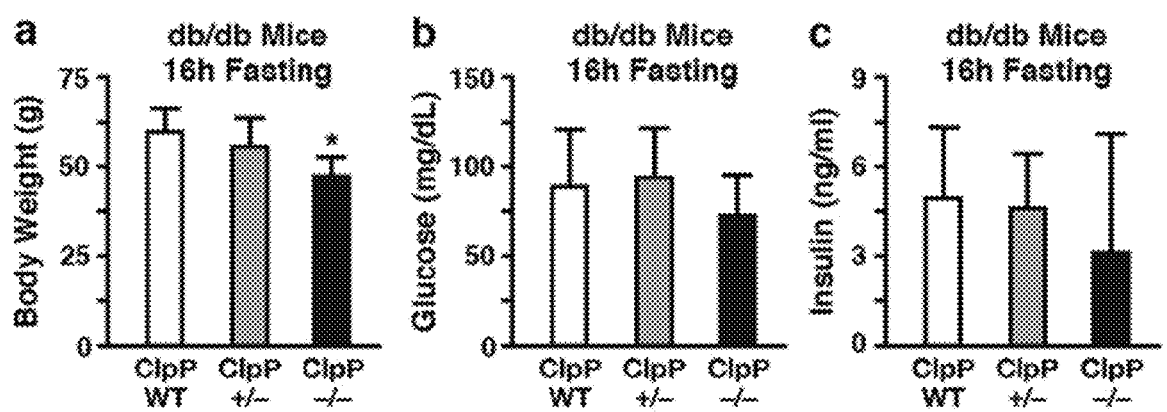
FIG. 14 (panels a-c) provide data related to the effects of knocking out ClpP on obesity and insulin resistance in db/db mice.

ClpP$^{-/-}$ mice were cross-bred with db/db mice (a model of obesity, diabetes, and dyslipidemia) to determine whether and how depleting ClpP affects the obese and diabetic phenotypes of db/db mice. Knocking out ClpP led to a small but significant decrease in body weight of db/db mice (FIG. 14, panel a). ClpP knockout also significantly decreased blood glucose levels in db/db mice after 4 h of fasting (FIG. 3, panel n), although this effect disappeared after 16 h of fasting probably due to the fact that the glucose levels in db/db mice with WT ClpP after 16 h fasting were already dropped to normal levels (FIG. 14, panels b-c). More importantly, eliminating ClpP greatly improved the glucose tolerance of db/db mice (FIG. 3, panel o).

Example 4

Absence of ClpP in Mice Upregulates Mitochondrial Chaperon Levels

Figure 15:
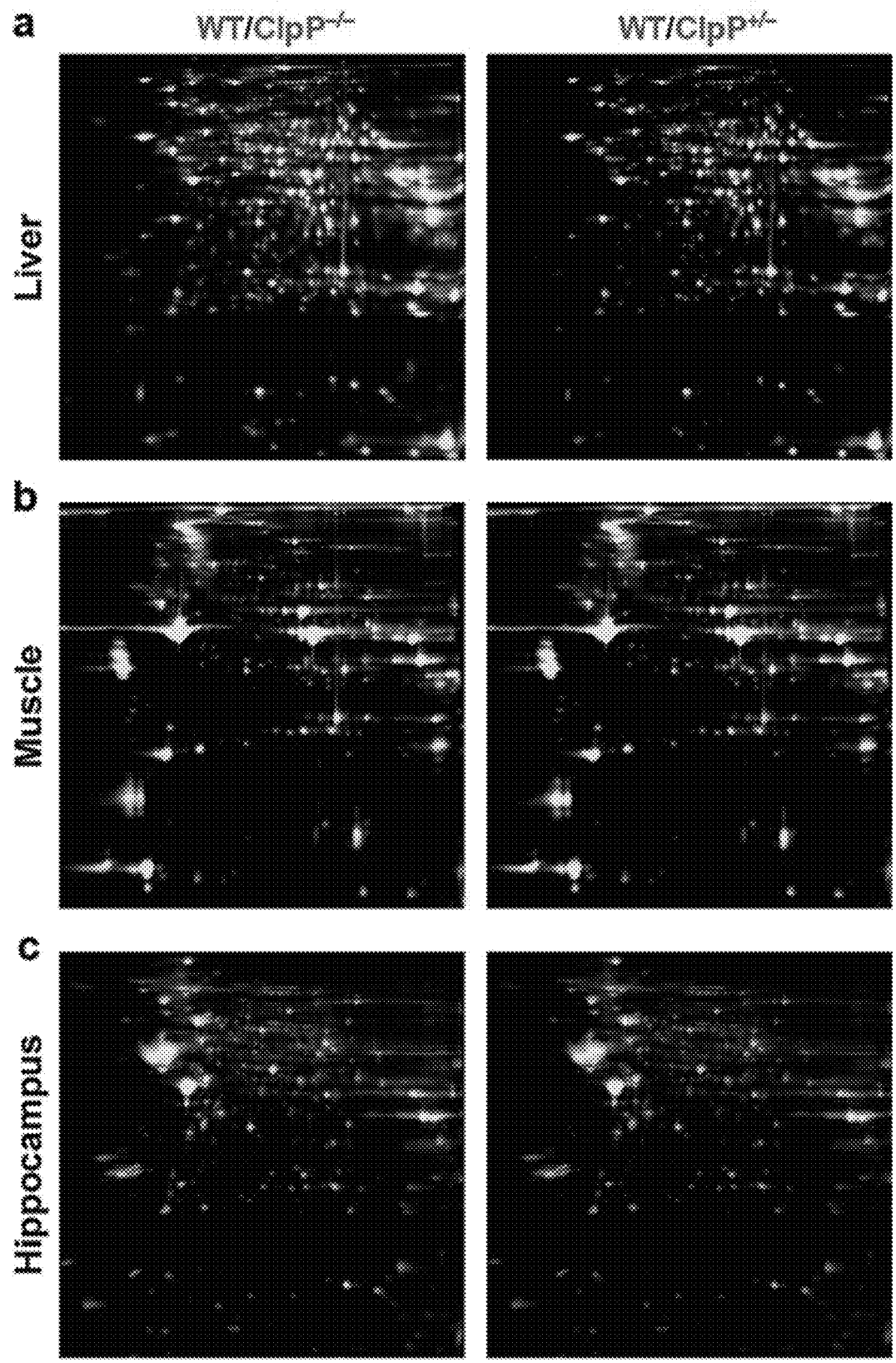
FIG. 15 (panels a-c) provide representative images from comparative 2D fluorescence difference gel electrophoresis (2D-DIGE) on different organs.

To identify downstream effectors of ClpP, two dimensional (2D) fluorescence difference gel electrophoresis (2D-DIGE) was employed to compare the protein profiles of various organs from mice with different ClpP genotypes (FIG. 15). Mass spectrometry was then used to identify the most dramatically changed proteins in different organs of ClpP$^{-/-}$ mice (FIG. 20). Validation by western blots confirmed six potential ClpXP downstream effectors (TRAP1, Grp75, LRPPRC, ClpX, OAT, and LonP; FIG. 21); their protein levels increased greatly in multiple organs (FIG. 4, panels a-h and FIG. 16), but their mRNA levels remained the same in most cases (FIG. 22). Thus, ClpP likely controls the levels of these proteins post-transcriptionally. Significantly increased protein levels were also detected in embryonic day-19 pups (not shown), without a decrease in body weight, suggesting that the accumulation of these proteins is likely the cause, rather than a consequence, of the observed phenotypes. Increased levels of the same proteins were also detected in mouse fibroblasts (FIG. 4, panels i-j), which were subsequently reduced by overexpressing mouse ClpP (FIG. 4, panel k-l), suggesting that ClpP specifically regulates these protein levels in a cell-autonomous manner.

Figure 4:
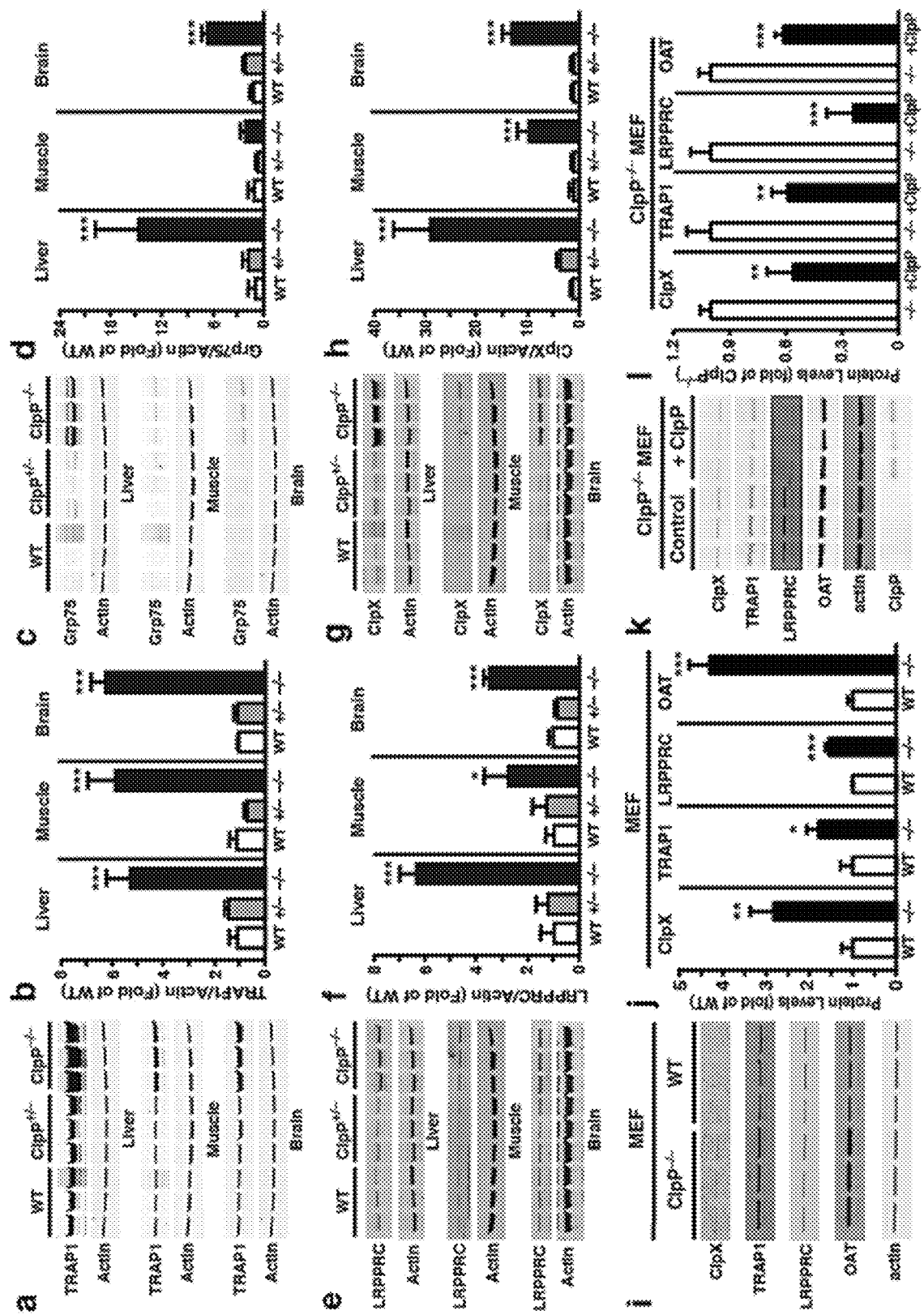
FIG. 4 (panels a-l) provide data showing that ClpP$^{-/-}$ mice had increased mitochondrial chaperone levels.
Figure 16:
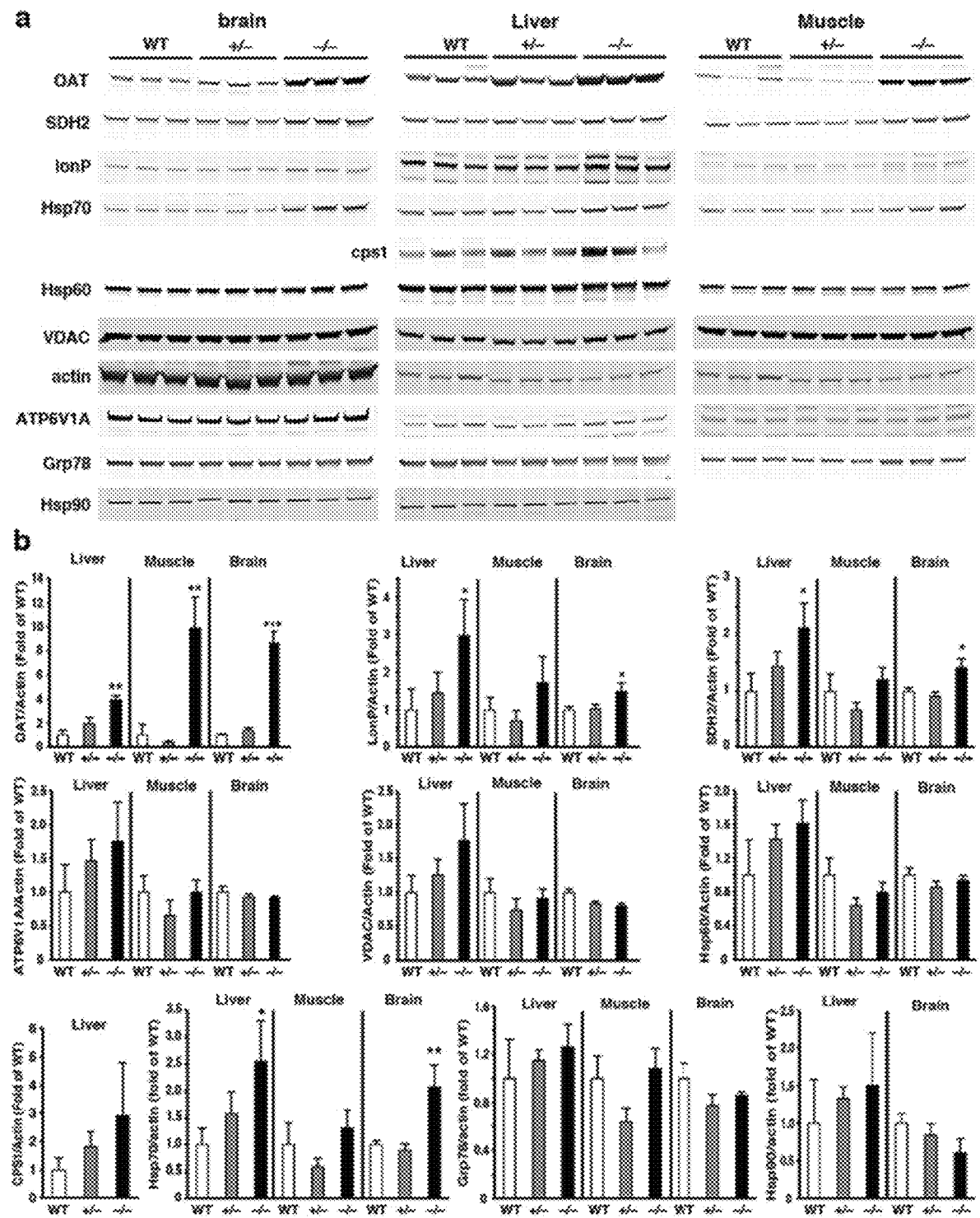
FIG. 16 (panels a-b) provide data showing that the absence of ClpP increases the levels of many mitochondrial proteins in various organs.

Strikingly, many of the potential ClpP downstream effectors are related to mitochondrial protein homeostasis, including the molecular chaperones ClpX (mitochondrial Hsp100), TRAP1 (mitochondrial Hsp90), and Grp75 (mitochondrial Hsp70) as well as mitochondrial protease LonP (FIG. 4, panels a-h, FIG. 16). ClpP knockout had no significant effect on the levels of mitochondrial proteins VDAC and Hsp60 (FIG. 16). Furthermore, there were no significant differences in many cytosol and endoplasmic reticulum (ER) heat shock proteins, such as Bip and Hsp90 (FIG. 16). Thus, either directly or indirectly, ClpP controls a specific group of mitochondrial proteins, especially chaperons.

Example 5

Figure 5:
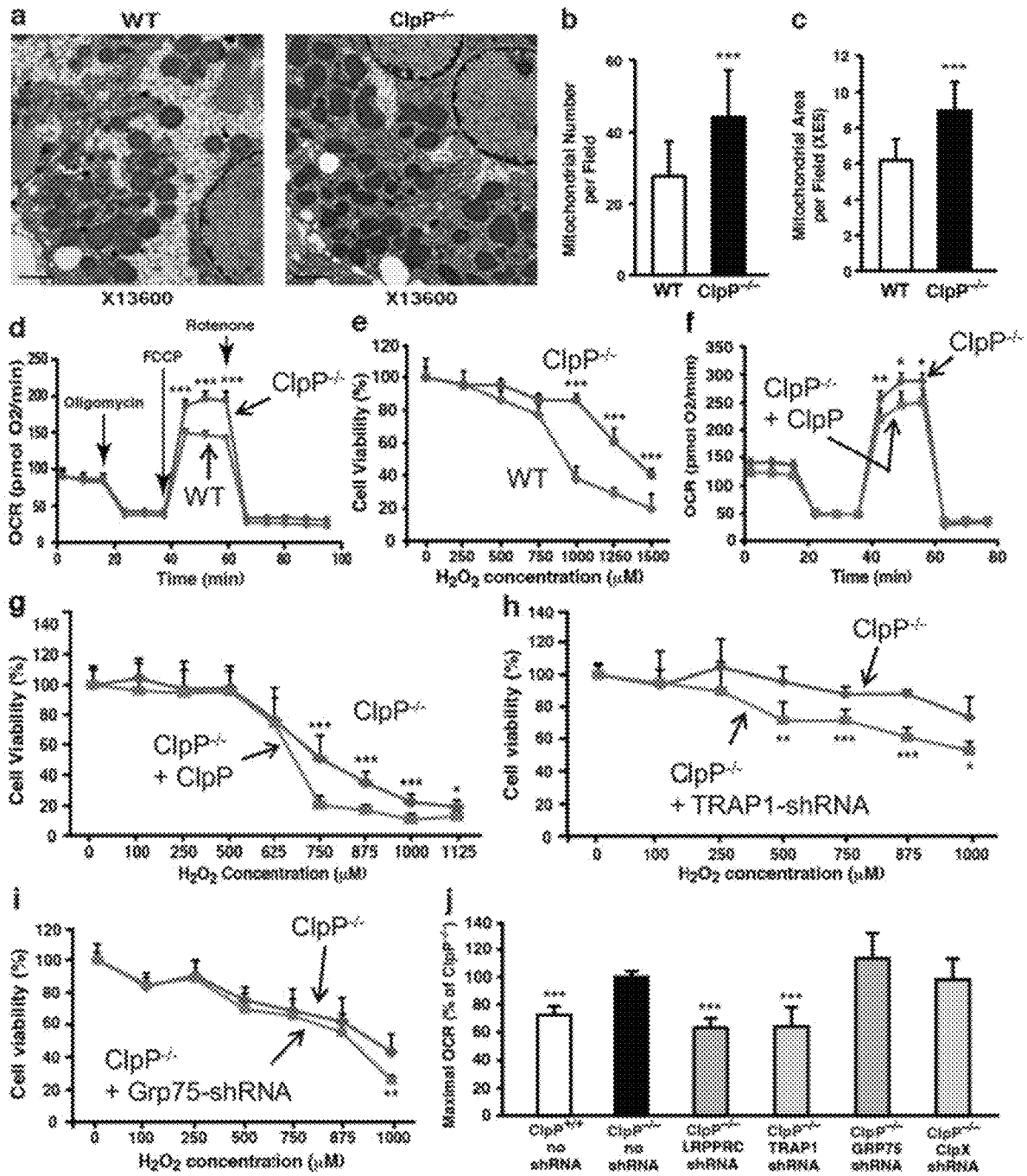
FIG. 5 (panels a-j) provide data showing that ClpP$^{-/-}$ mice had increased mitochondrial numbers, improved mitochondrial function, and enhanced anti-oxidative stress capability.

Absence of ClpP Increased Mitochondrial Numbers and Enhanced Mitochondrial Function and Anti-Stress Capacity Mitochondrial number and function were analyzed in ClpP$^{-/-}$ mice. Electron microscopic (EM) study of ClpP$^{-/-}$ liver sections showed that depletion of ClpP increased mitochondrial numbers and altered mitochondrial morphology in hepatocytes (FIG. 5, panels a-b and FIG. 17, panels a-b). Mitochondrial mass (measured by total mitochondrial area per field) was also significantly increased in ClpP$^{-/-}$ hepatocytes (FIG. 5, panel c, and FIG. 17, panels a-b). The ClpP$^{-/-}$ mitochondria had denser matrixes compared to those of WT (FIG. 5, panel a, and FIG. 17, panels a-b), probably due to increased protein content in ClpP$^{-/-}$ mitochondria. Although the size distribution of mitochondria was similar between ClpP$^{-/-}$ and WT hepatocytes (FIG. 17, panel c), there was a higher percentage of ClpP$^{-/-}$ mitochondria with lower roundness (FIG. 17, panel d), suggesting that more ClpP$^{-/-}$ mitochondria had elongated shapes.

To determine whether ClpP regulates mitochondrial function, the respiratory capacity of fibroblasts from ClpP$^{-/-}$ and WT mice were compared using a Seahorse XF analyzer. ClpP$^{-/-}$ fibroblasts had a similar basal oxygen consumption rate (OCR) but a significantly higher maximal OCR compared with WT fibroblasts (FIG. 5, panel d), indicating enhanced mitochondrial function in the absence of ClpP. ClpP$^{-/-}$ fibroblasts also showed resistance to $H_2O_2$-induced cytotoxicity compared with WT fibroblasts (FIG. 5, panel e), suggesting increased anti-oxidative stress capacity in the absence of ClpP. Overexpression of mouse ClpP in ClpP$^{-/-}$ fibroblasts not only led to decreased levels of the ClpP downstream effectors (FIG. 4, panels k-l) but also abolished the enhancement of mitochondrial function and resistance to $H_2O_2$-induced cytotoxicity observed in ClpP$^{-/-}$ cells (FIG. 5, panels f-g).

Example 6

Figure 18:
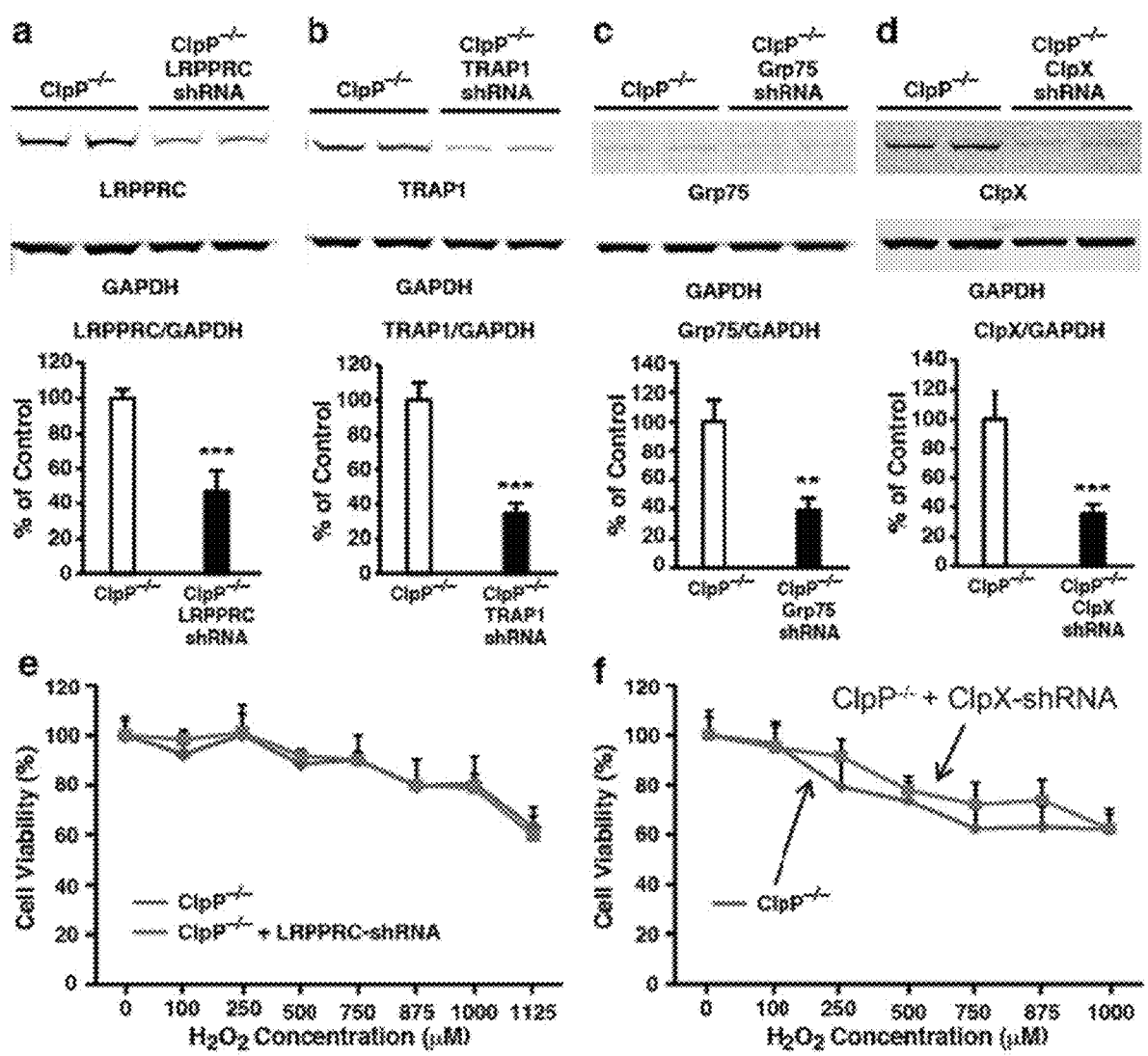
FIG. 18 (panels a-f) provide data related to knocking down ClpP targeting proteins in ClpP$^{-/-}$ fibroblasts and a cell viability assay.

Mitochondrial Effectors TRAP1, Grp75, and LRPPRC Mediated the Effects of ClpP Absence on Mitochondrial Function and Anti-Stress Capacity To determine whether and which of the mitochondrial effectors regulated by ClpP mediated the enhanced mitochondrial function seen in ClpP$^{-/-}$ fibroblasts, lentiviral shRNAs were used to knock down each of them in ClpP$^{-/-}$ fibroblasts. This was followed by functional assays (FIG. 18, panels a-d). Knocking down TRAP1 or Grp75, but not LRPPRC and ClpX, abolished or lowered the resistance of ClpP$^{-/-}$ fibroblasts to $H_2O_2$ cytotoxicity (FIG. 5, panels h-i and FIG. 18, panels e-f). Knocking down either LRPPRC or TRAP1 abolished the enhanced respiratory capacity of ClpP$^{-/-}$ cells, while lowering the level of ClpX or Grp75 had no such an effect (FIG. 5, panel j). These data suggest that ClpP regulates mitochondrial function by controlling its effector levels, specifically TRAP1, Grp75, and LRPPRC. These proteins may affect mitochondrial function via distinct pathways or have synergistic effects on the same pathway.

Example 7

Hepatic ClpP Was Responsible For Regulating Insulin Sensitivity

Figure 6:
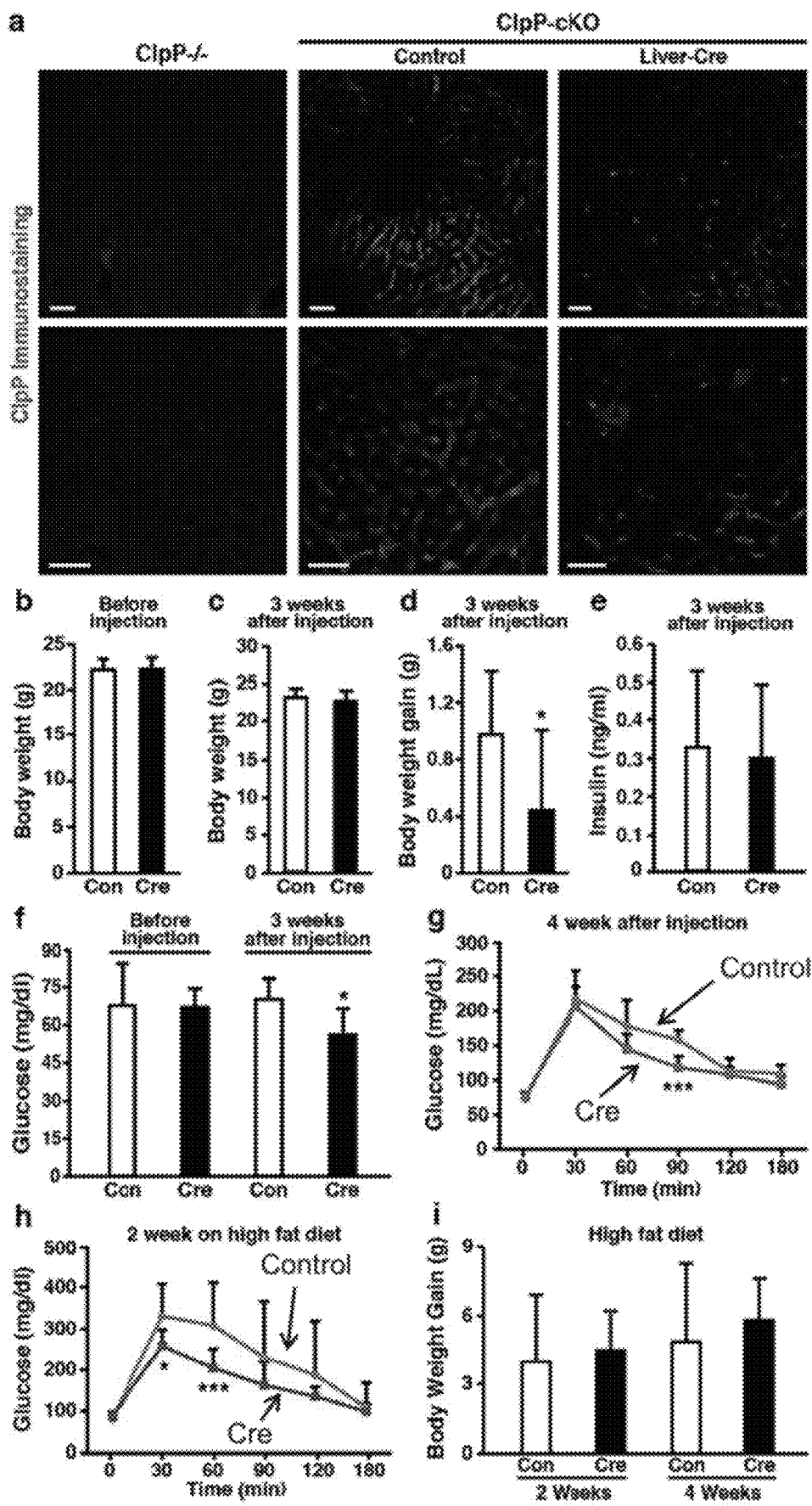
FIG. 6 (panels a-i) provide data showing that AAV-Cre-mediated knockdown of ClpP in livers increased insulin sensitivity in ClpP-cKO mice. 3-5 month-old ClpP-cKO mice were injected with AAV-CMV-Cre (Cre group, n=11) or control AAV (Con group, n=10) through tail vein at a dose of 5×10$^9$ gc/gram.

Multiple tissues can affect insulin sensitivity through different mechanisms. ClpP conditional knockout mice (ClpP-cKO) were employed to further dissect the tissue specific mechanism(s) underlying the phenotypes of ClpP$^{-/-}$ mice. In this mouse model, LoxP sites were inserted to flank the mouse genomic region containing ClpP exons 1-3 for future removal. To delete ClpP specifically in the liver, AAV-CMV-Cre was injected through the tail vein into ClpP-cKO mice. The ClpP levels in livers, detected by immunostaining, were dramatically reduced in Cre-injected mice compared to control AAV-injected mice (FIG. 6, panel a). At three weeks after injection, the Cre-injected mice had a significantly lower body weight gain than the control mice (FIG. 6, panel d), although the total body weights were not significantly different between the two groups of mice (FIG. 6, panels b-c). The blood glucose levels of the Cre-injected mice were also significantly lower than those of the control mice (FIG. 6, panel f), while no difference in plasma insulin levels was detected (FIG. 6, panel e). The enhanced insulin sensitivity of Cre-injected mice was revealed by glucose tolerance test in mice on either chow diet or HFD for two weeks (FIG. 6, panels g-h). Unlike ClpP$^{-/-}$ mice, liver specific knockdown of ClpP did not affect HFD-induced body weight gain (FIG. 6, panel i). These data suggest that hepatic ClpP levels are responsible for regulating the insulin sensitivity observed in ClpP$^{-/-}$ mice, without affecting the adipose content.

Figure 19:
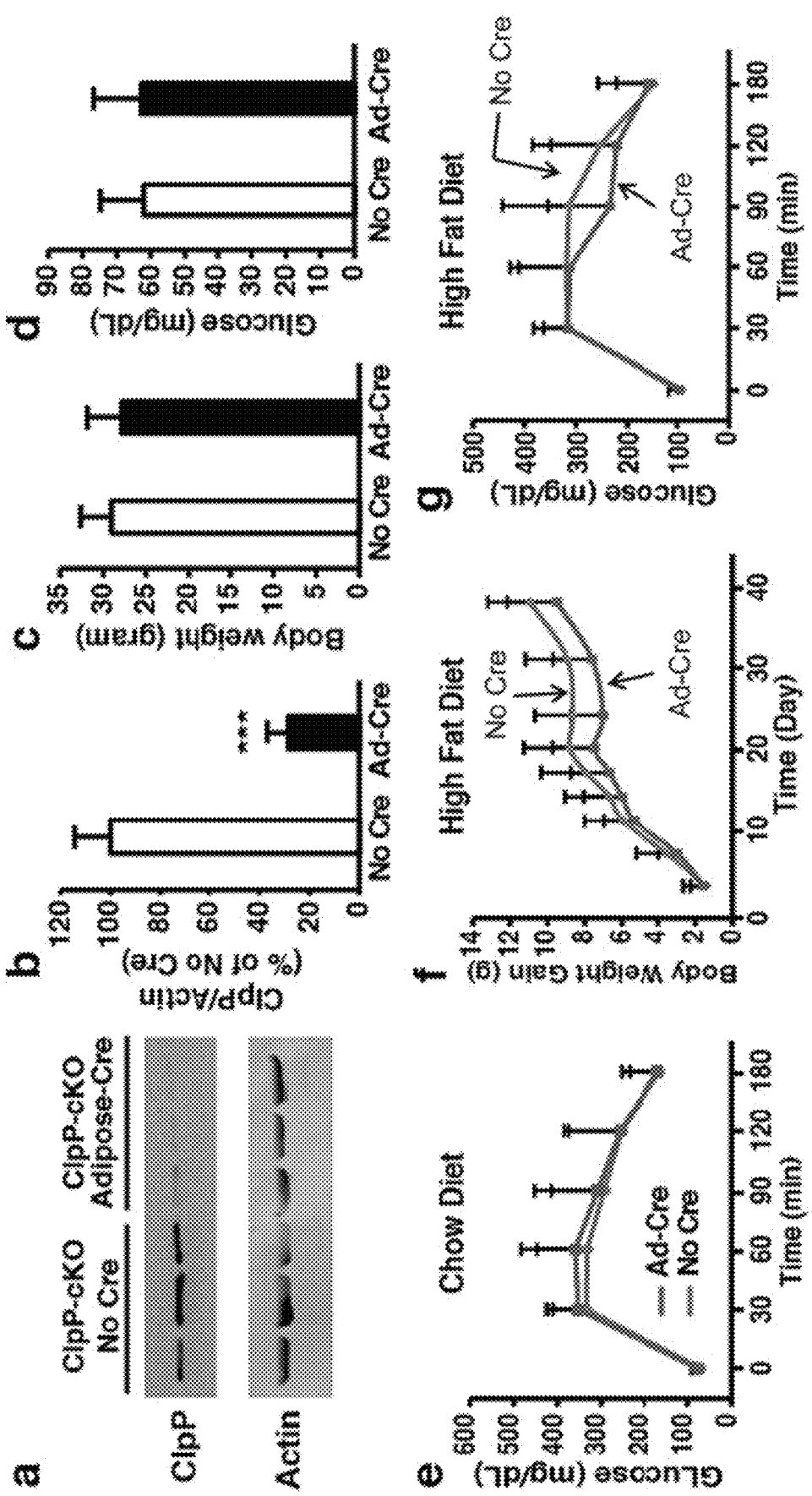
FIG. 19 (panels a-f) provide data showing that adipocyte-specific knockout of ClpP did not affect body weight, blood glucose levels, and insulin sensitivity in mice.
Figure 23:
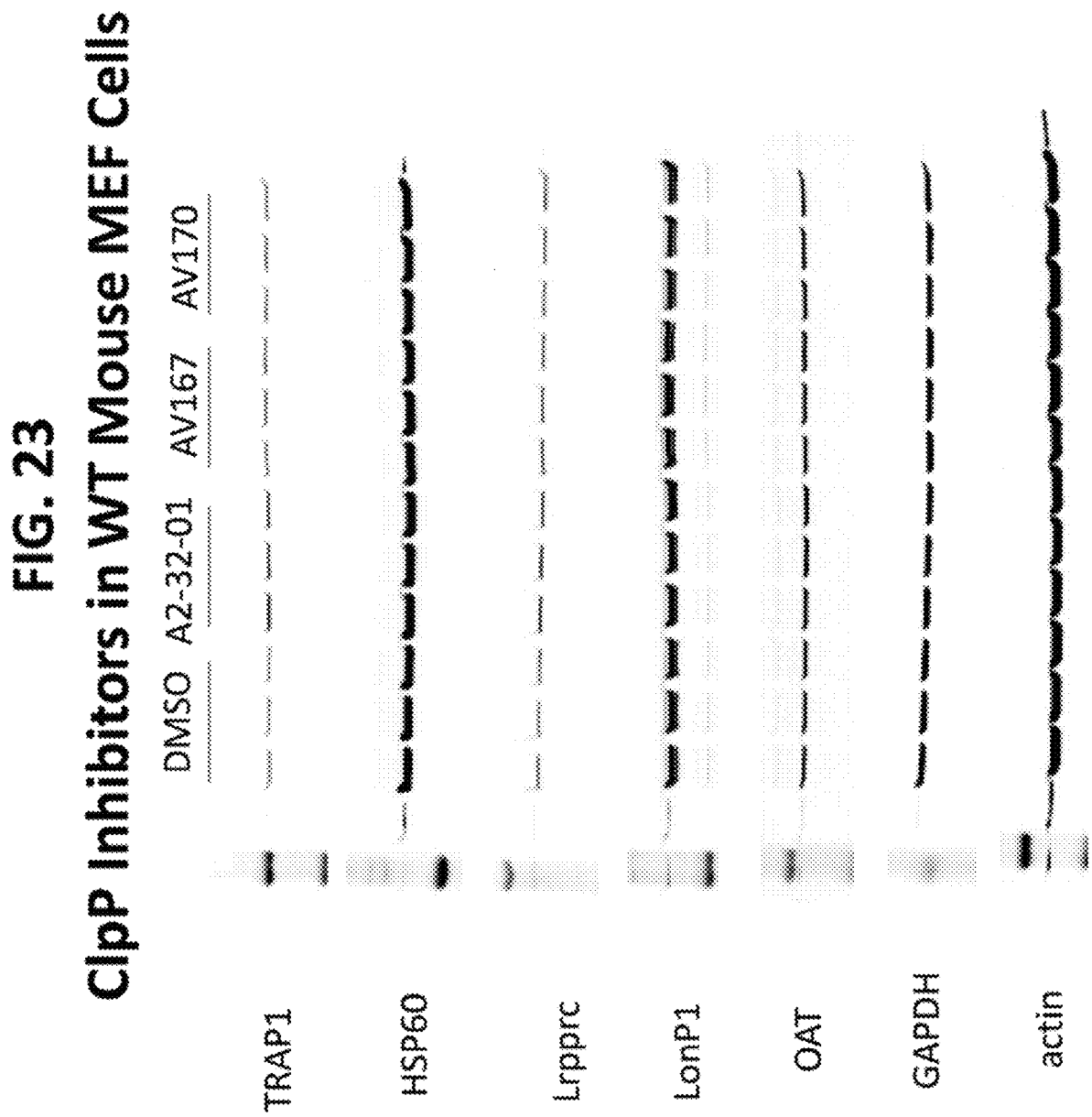
FIG. 23 provides a western blot analysis of ClpP substrates following treatment with the small molecule ClpP inhibitors A2-32-01, AV167, and AV179.

ClpP-cKO mice were also crossed with ap2-Cre mice to establish adipocyte-specific ClpP-KO mice. The ClpP levels in adipose tissues of ClpP-cKO/ap2-Cre mice were about a quarter of those in control mice (FIG. 19, panels a-b). It was not clear whether the residue ClpP levels were due to uncompleted deletion of Clpp by ap2-Cre or contamination of other tissues or cells (such as vascular or immune cells) in the collected adipose tissues. No significant changes in body weights, blood glucose levels, and glucose tolerance were detected in ClpP-cKO/ap2-Cre mice (FIG. 19, panels c-e). The body weight gain and glucose tolerance of ClpP-cKO/ap2-Cre mice on HFD were also similar to those of control mice on the same diet (FIG. 19, panels f-g). Therefore, adipocytic ClpP is unlikely attributable to the reduced adipose deposition and enhanced insulin sensitivity seen in ClpP$^{-/-}$ mice.

Example 8

In-Vitro Analysis of Small Molecule ClpP Inhibitors in Mouse Embryonic Fibroblast (MEF) Cells Wild type mouse MEF cells were seeded at 200,000 cells per well at 6 well plates the day before treatment. Cells were treated with the small molecule ClpP inhibitors A2-32-01, AV167, and AV179 (described previously herein) at 10 μM in OPTI-MEM twice a day for 2 days (48 hr). For each treatment, the old medium will be removed and fresh medium added to the wells. After 48 hr treatment, the cells were harvested for western blot analysis or qPCR assay of ClpP substrates.

Figure 24:
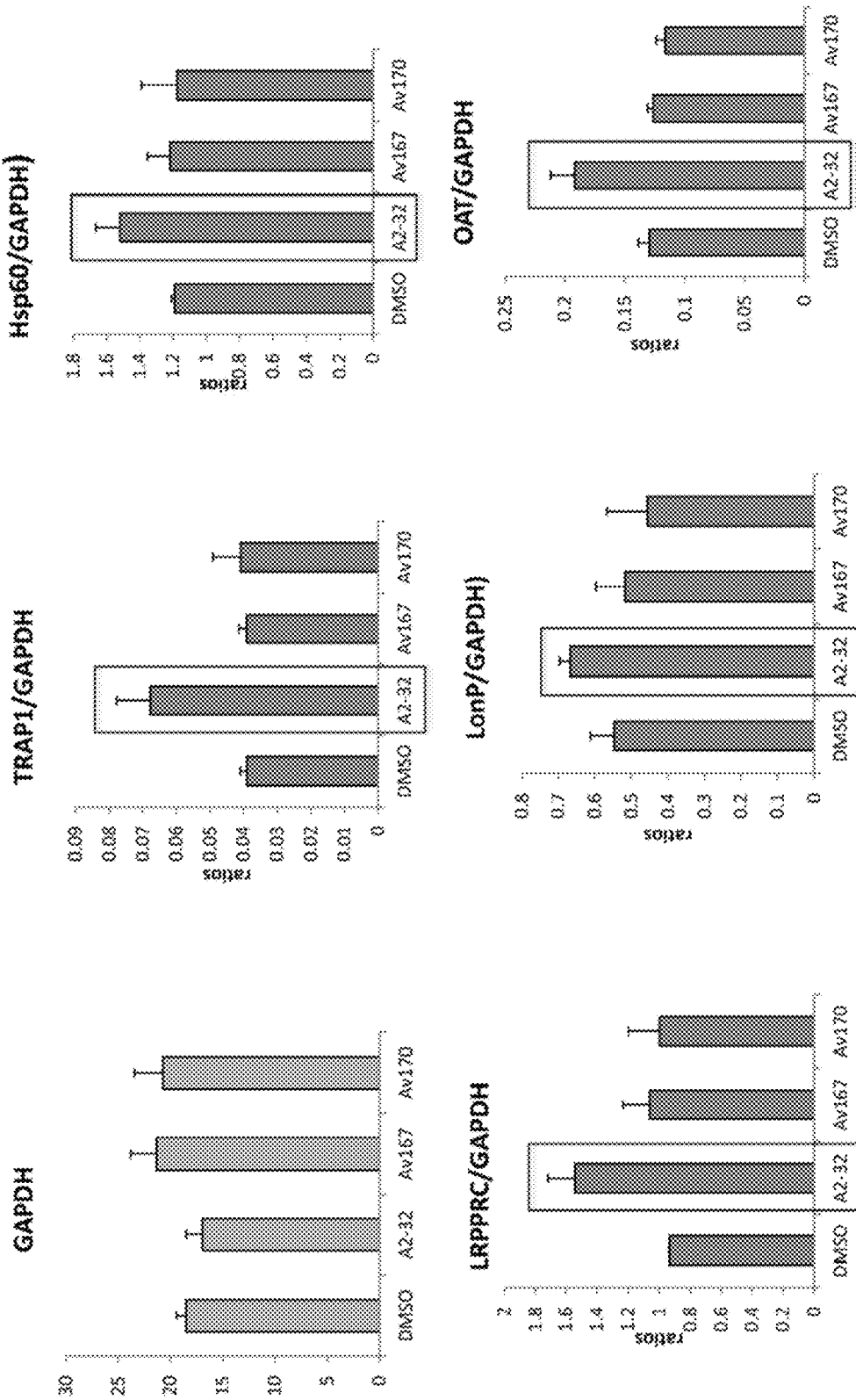
FIG. 24 provides graphs showing protein levels for ClpP substrates (normalized to GAPDH) following treatment with the small molecule ClpP inhibitors A2-32-01, AV167, and AV179.
Figure 25:
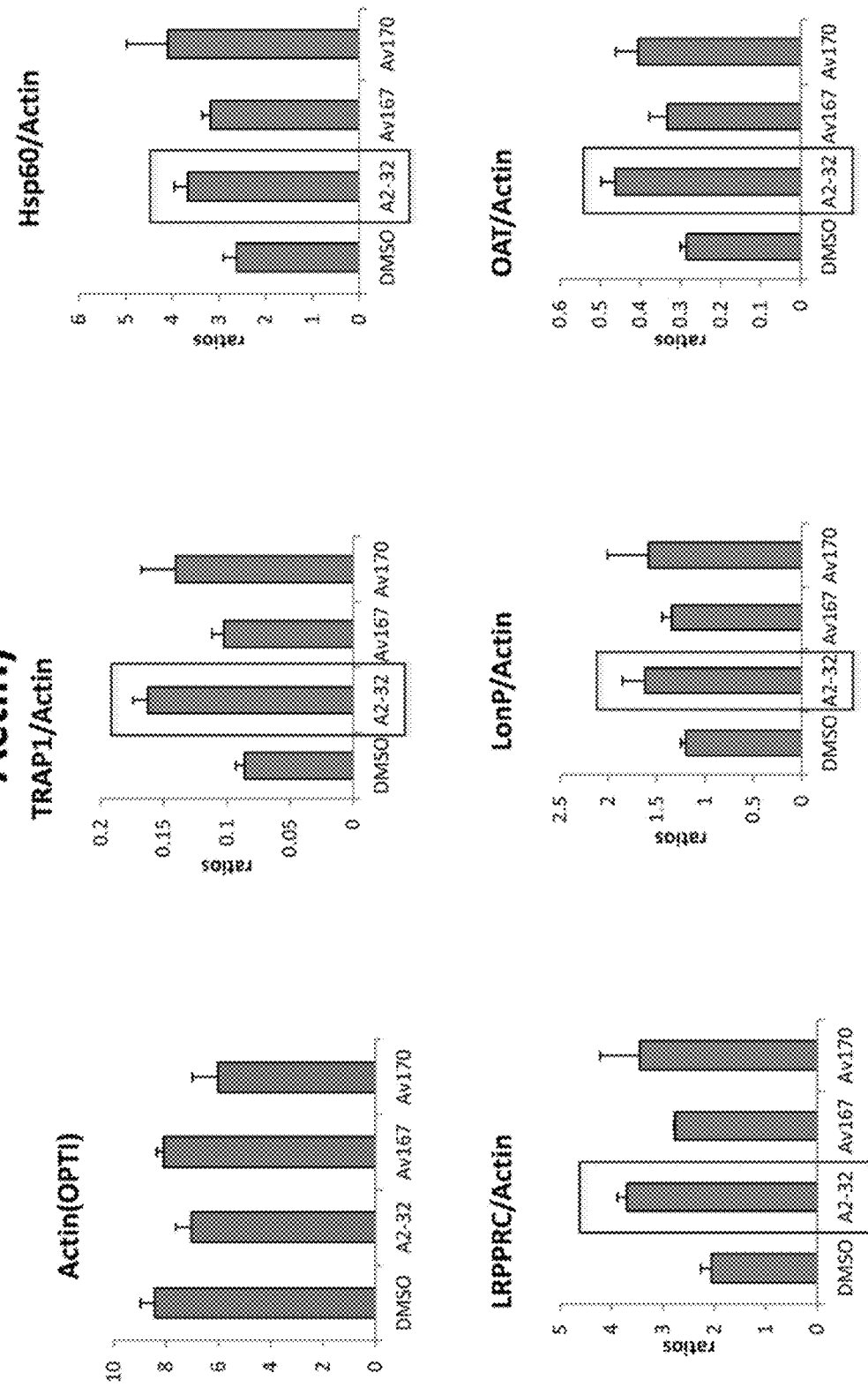
FIG. 25 provides graphs showing protein levels for ClpP substrates (normalized to Actin) following treatment with the small molecule ClpP inhibitors A2-32-01, AV167, and AV179.
Figure 26:
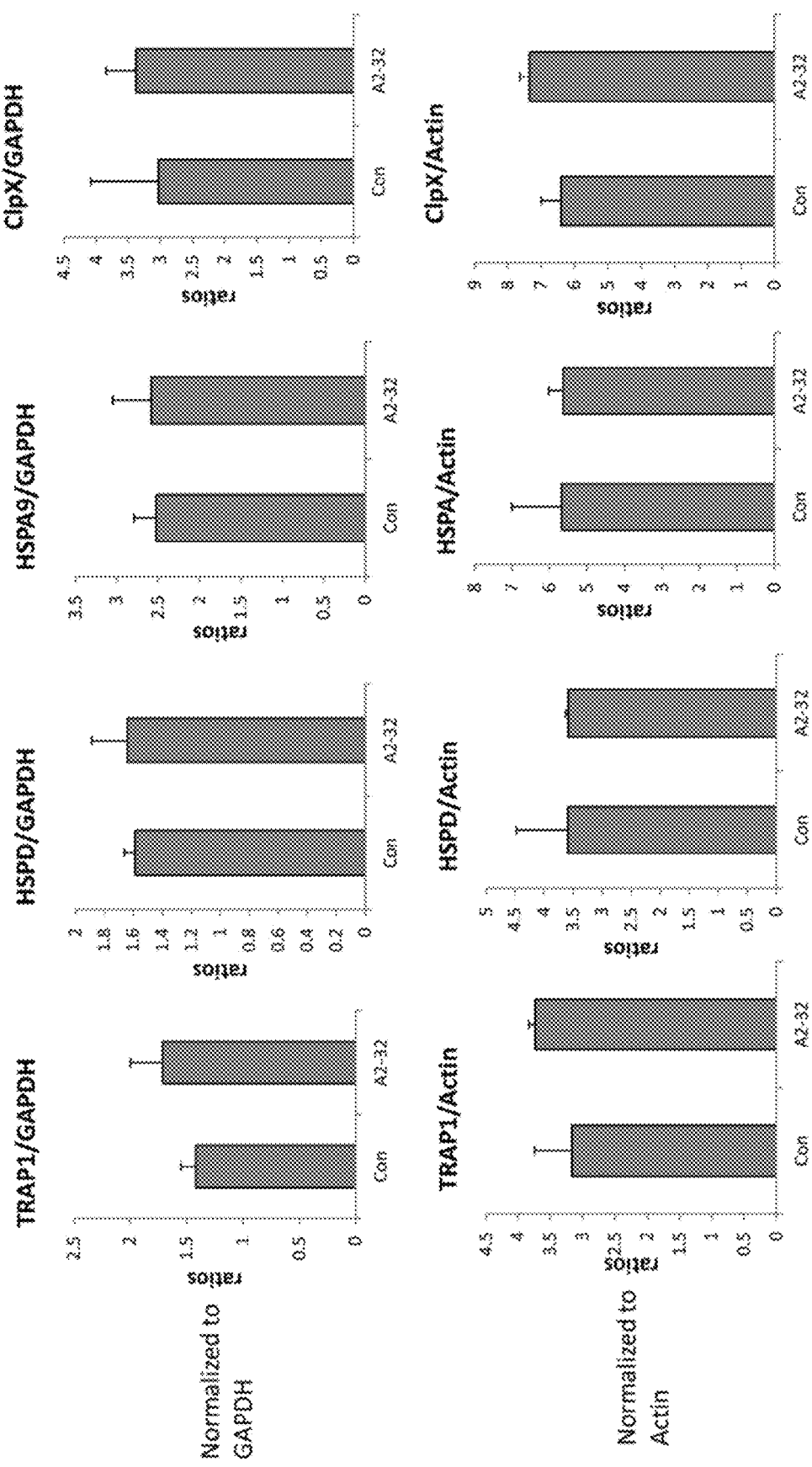
FIG. 26 provides graphs showing mRNA levels for ClpP substrates following treatment with A2-32-01.
Figure 27:
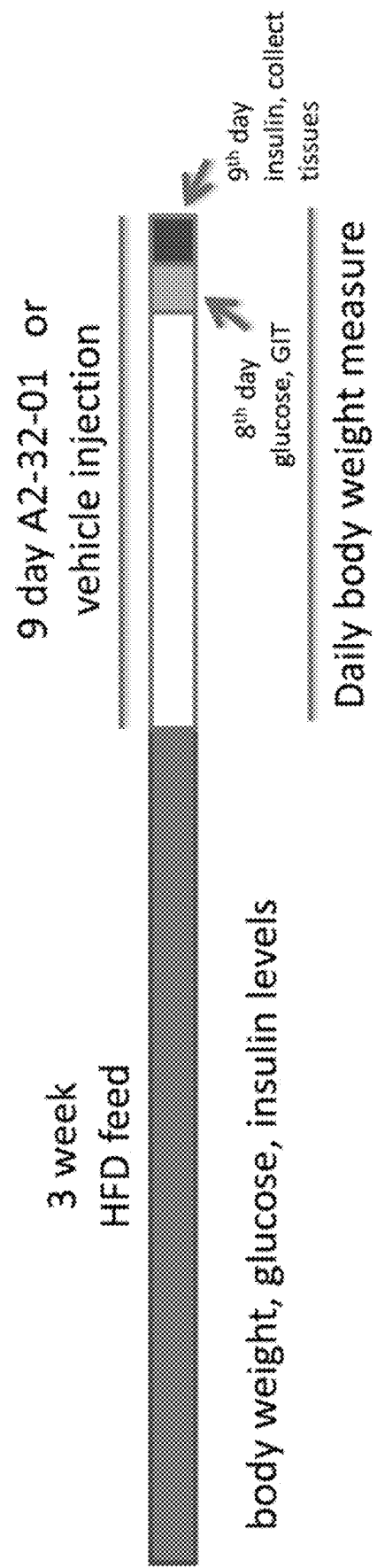
FIG. 27 provides an overview of the in vivo study design of Examples 9 and 10.

As shown in FIGS. 24 and 25, treatment with ClpP inhibitor A2-32-01 increased ClpP substrate protein levels in mouse MEF cells, mimicking the phenotypes observed in ClpP knock out MEF and in ClpP knock out mouse organs. As shown in FIG. 26, the mRNA level of these genes in mouse MEF cells remained unchanged after A2-32-01 treatment, which excluded potential off-target effects of A2-32-01 through transcription regulation.

Based on these in vitro data, further in vivo testing of A2-32-01 in high fat diet (HFD)-induced obesity and diabetes mouse models was performed as described in Example 9 below.

Example 9

Figure 28:
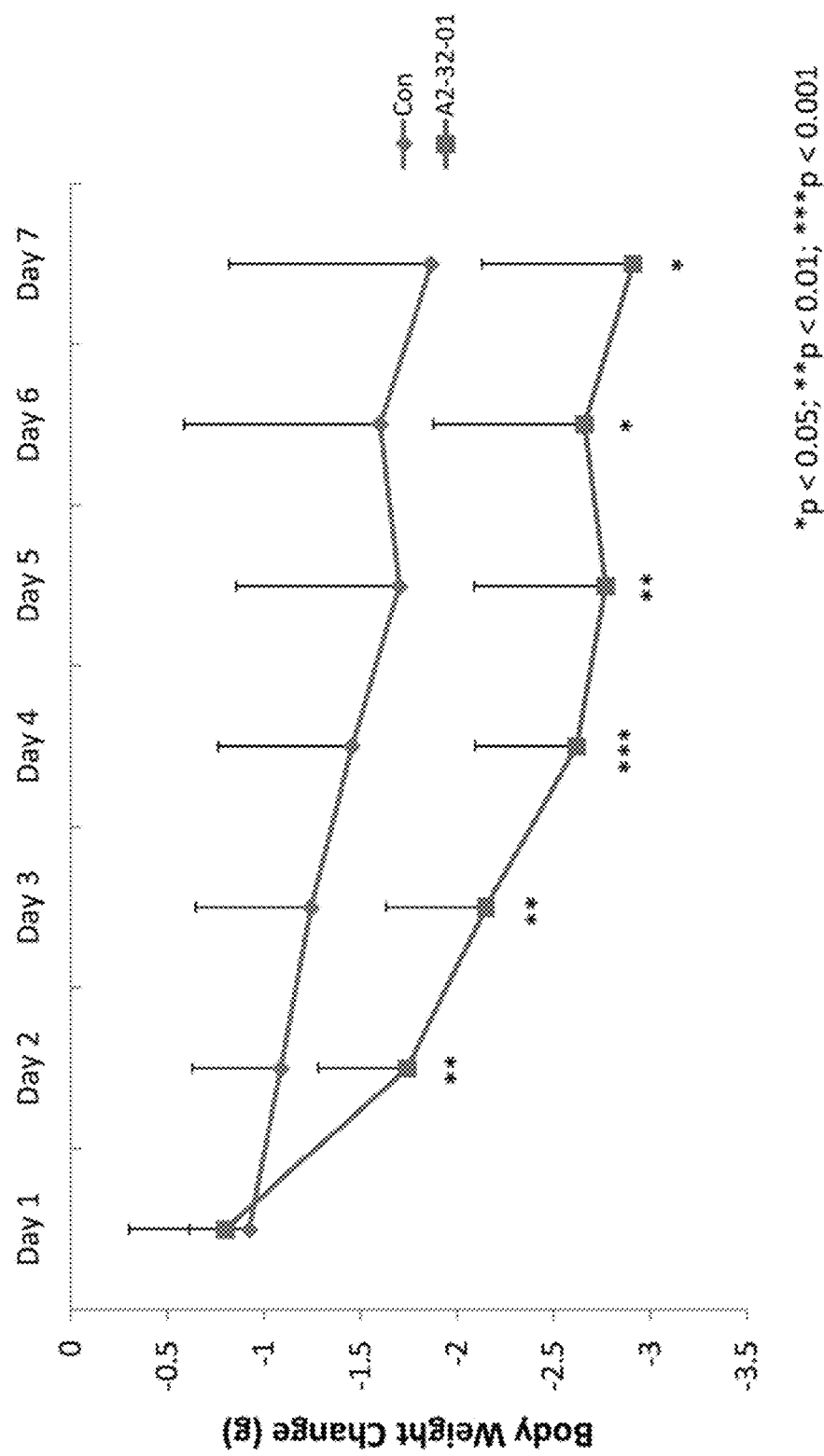
FIG. 28 provides a graph showing body weight data from the first two days of in vivo 12-32-01 treatment from Example 9.
Figure 29:
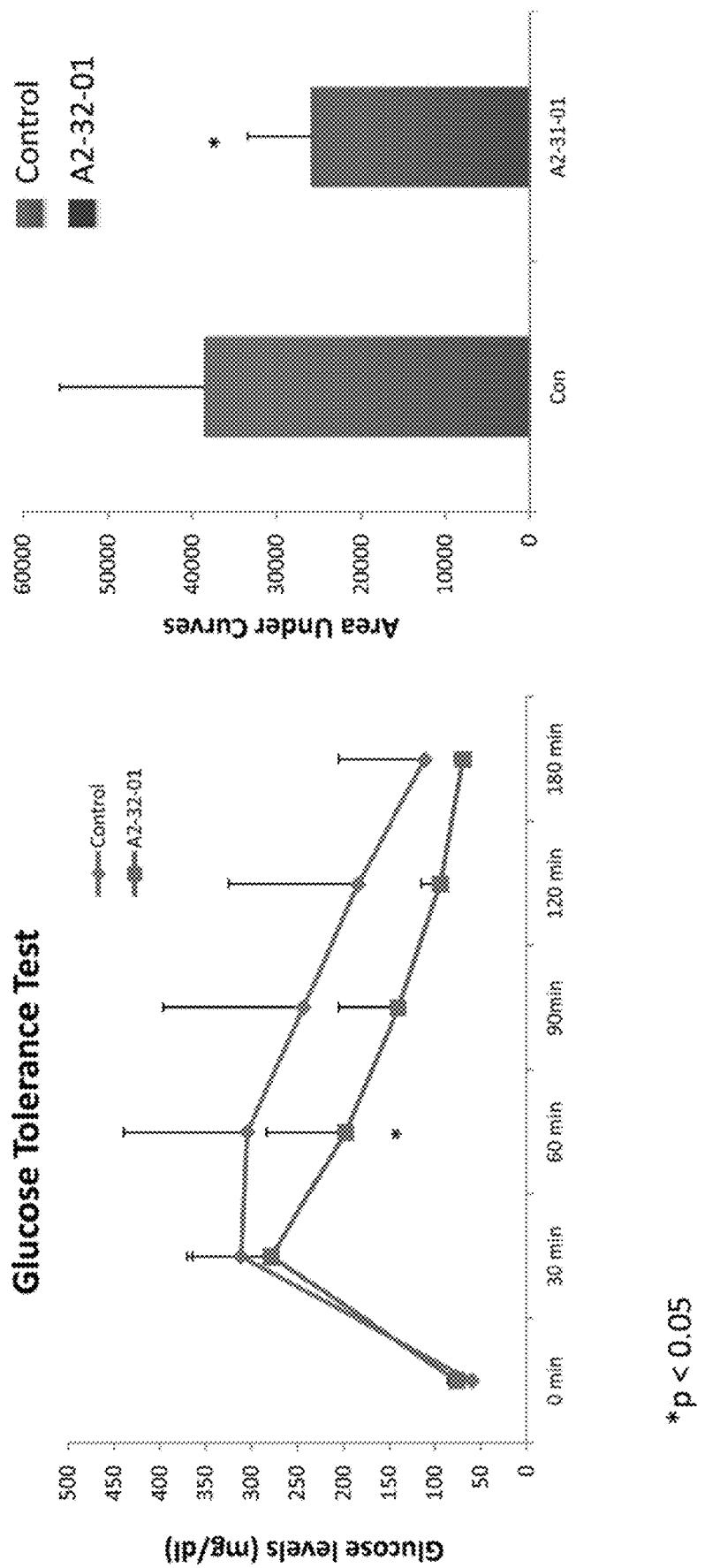
FIG. 29 provides graphs showing the results of a glucose tolerance test following in vivo administration of a ClpP inhibitor in a high fat diet (HFD)-induced obesity and diabetes mouse model.

In-Vivo Analysis of Small Molecule ClpP Inhibitor A2-32-01 in High Fat Diet (HFD)-Induced Obesity and Diabetes Mouse Models 7-9 month old WT female (20 mice), were fed with high fat diet for 3 weeks. Body weight change and blood glucose/plasma insulin levels in response to HFD were measured. At the beginning of the $4^{th}$ week, for treatment group, A2-32-01 was injected peritoneally twice daily at 300 mg/kg for 8 days. For the control group, corn oil (vehicle) was injected. The mice were maintained on HFD. The body weight change was followed every day. At the $8^{th}$ day of A2-32-01 injection, blood glucose levels were measured, and a glucose tolerance test was applied to measure insulin sensitivity. Body weight data from the first seven days of in vivo A2-32-01 treatment is provided in FIG. 28, which show a significant decrease in body weight on day 2 through day 7 as compared to the vehicle control group. A glucose tolerance test, which reflects insulin sensitivity, was performed on day 8 and the data are provided in FIG. 29, which show a significant improvement of insulin sensitivity in A2-32-01-treated mice as compared to the vehicle control mice.

Example 10

Continued In-Vivo Analysis of Small Molecule ClpP Inhibitor A2-32-01 in High Fat Diet (HFD)-Induced Obesity and Diabetes Mouse Models (Prophetic)

The in-vivo analysis of Example 9 is continued, with collection of the blood and multiple organs (liver/muscle/brain) at day 9 of A2-32-01 injection. Mitochondria are isolated from mouse liver and ClpP activity is tested using peptide substrates, e.g., as described herein. Western blot analysis is performed to detect ClpP substrate levels.

Example 11

Figure 30:
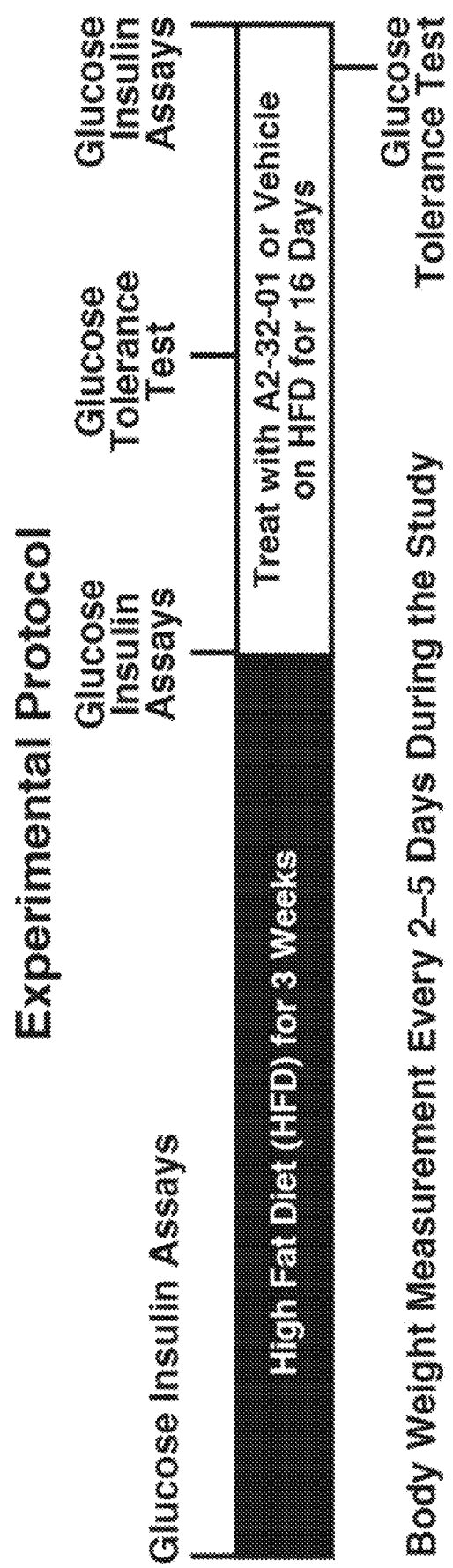
FIG. 30 provides a schematic showing an experimental scheme of HFD, A2-32-01 treatment, and metabolic assays.
Figure 31:
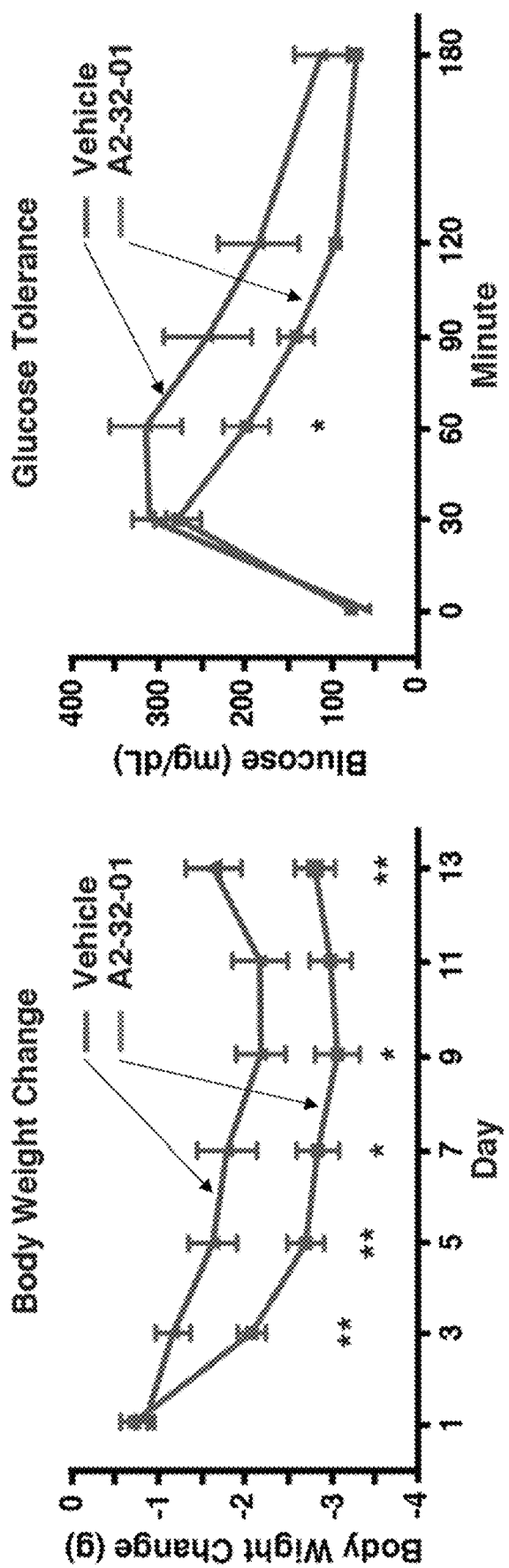
FIG. 31 provides a graph showing body weight change of HFD-fed WT mice in response to A2-32-01 treatment (n=9 for vehicle group, n=10 for A2-32-01 group) (left panel).
Figure 32:
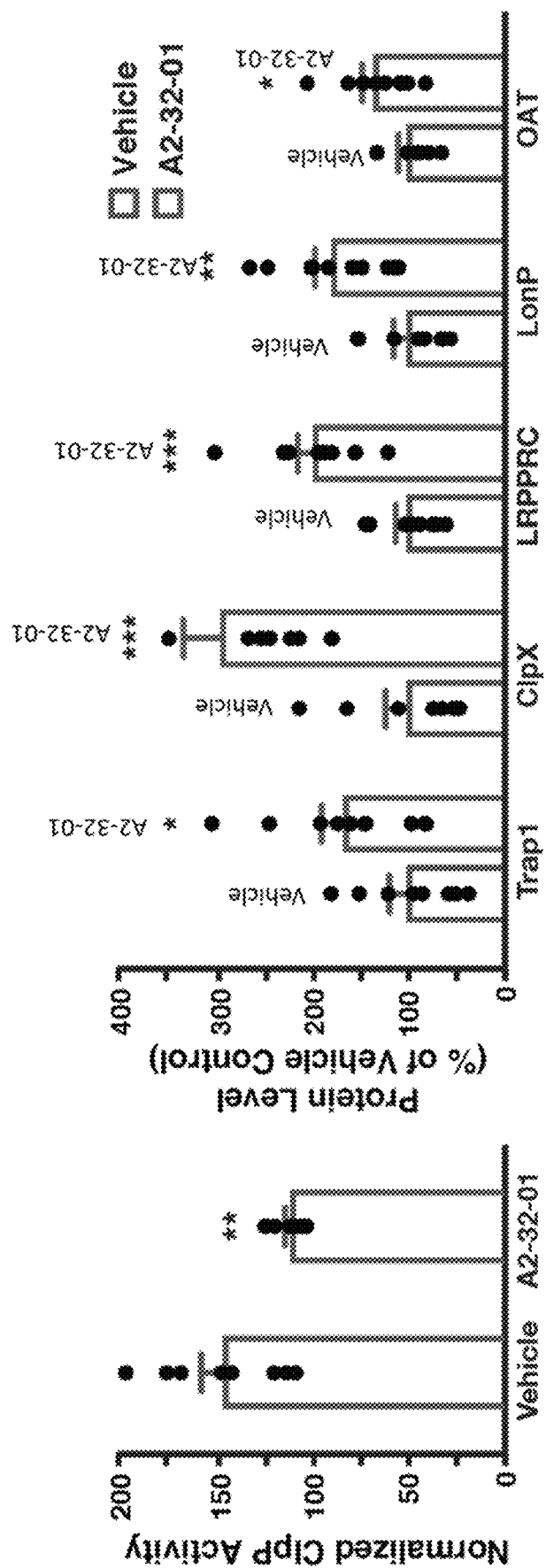
FIG. 32 provides a graph showing ClpP activity was lower in liver mitochondrion lysates from A2-32-01-treated mice compared to those from vehicle-treated mice (n=8 for vehicle group, n=10 for A2-32-01 group) (left panel).
Figure 33:
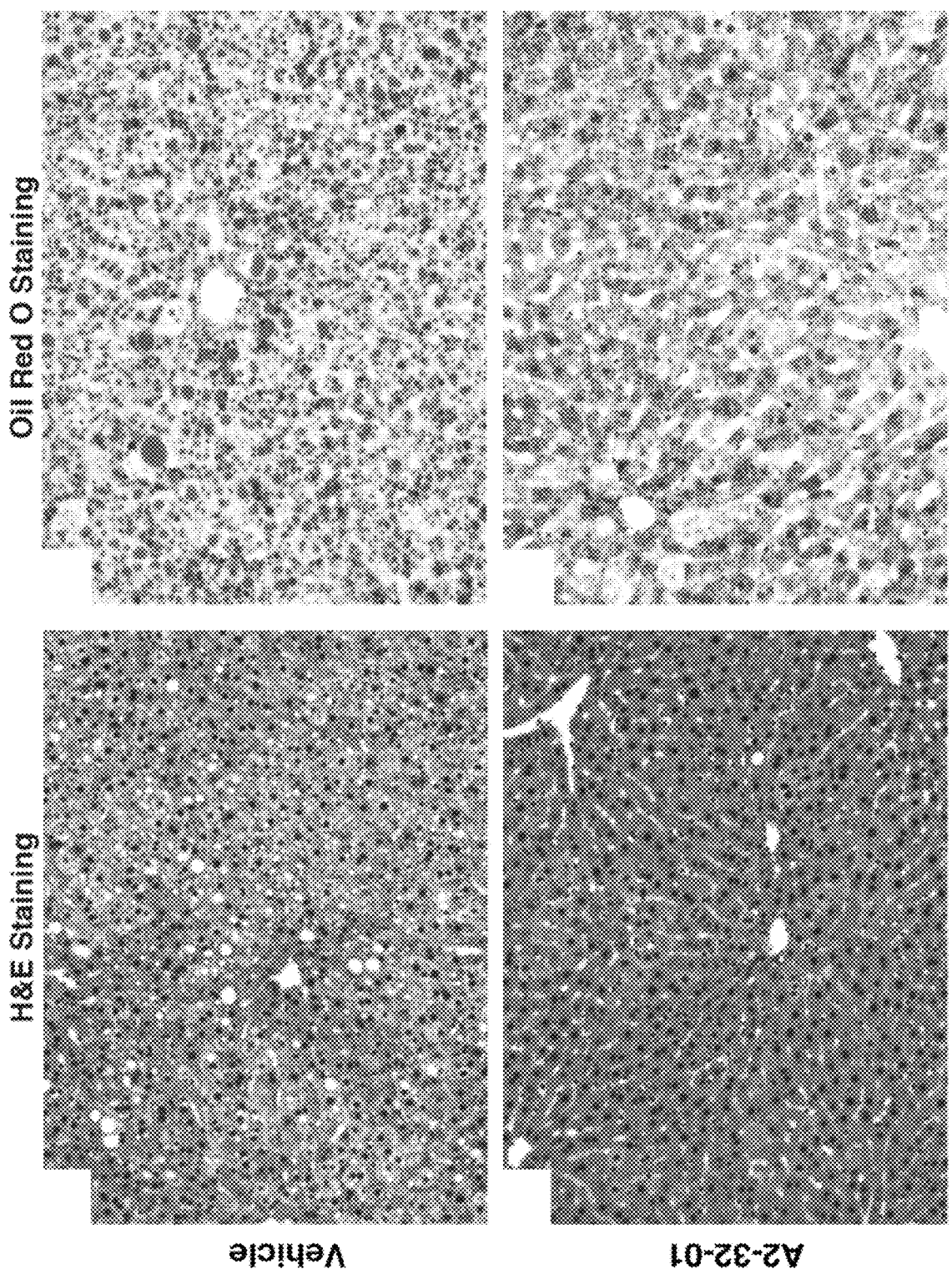
FIG. 33 provides representative H&E and oil red staining of liver sections from vehicle or A2-32-01 treated WT mice on HFD. The micrographs showed that A2-32-01 treatment lowered the lipid accumulation in liver cells and restored normal morphology of liver cells in WT mice on HFD, as compared to vehicle-treated WT mice on HFD.

Continued In-Vivo Analysis of Small Molecule ClpP Inhibitor A2-32-01 in High Fat Diet (HFD)-Induced Obesity and Diabetes Mouse Models The in-vivo analysis described in Examples 9 and 10 was continued in accordance with the experimental protocol shown in FIG. 30. As shown in FIG. 31 (left panel), the A2-32-01-treated mice on HFD had significantly decreased body weight compared to vehicle-treated mice on HFD. As shown in FIG. 31 (right panel), glucose tolerance tests showed increased insulin sensitivity in HFD-fed WT mice treated with A2-32-01 compared to those treated with vehicle. ClpP activity was lower in liver mitochondrion lysates from A2-32-01-treated mice compared to those from vehicle-treated mice as shown in FIG. 32, left panel. As shown in FIG. 32, right panel, the levels of tentative ClpP effectors (Trap1, ClpX, LRPPRC, LonP, and OAT), measured by western blot, were higher in liver mitochondrion lysates from A2-32-01-treated mice compared to those from vehicle-treated mice. Finally, FIG. 33 shows liver morphology from vehicle or A2-32-01-treated WT mice on HFD, indicating that A2-32-01 treatment lowered the lipid accumulation in liver cells and restored normal morphology of liver cells in WT mice on HFD, as compared to vehicle-treated WT mice on HFD. Overall, these data demonstrate that treatment with the ClpP inhibitor A2-32-01 in high fat diet (HFD)-fed wildtype (WT) mice significantly lowers body weight, increases insulin sensitivity, and restores normal liver morphology.

Example 12

In-Vivo Analysis of Small Molecule ClpP Inhibitor A2-32-01 in db/db Mice

Figure 34:
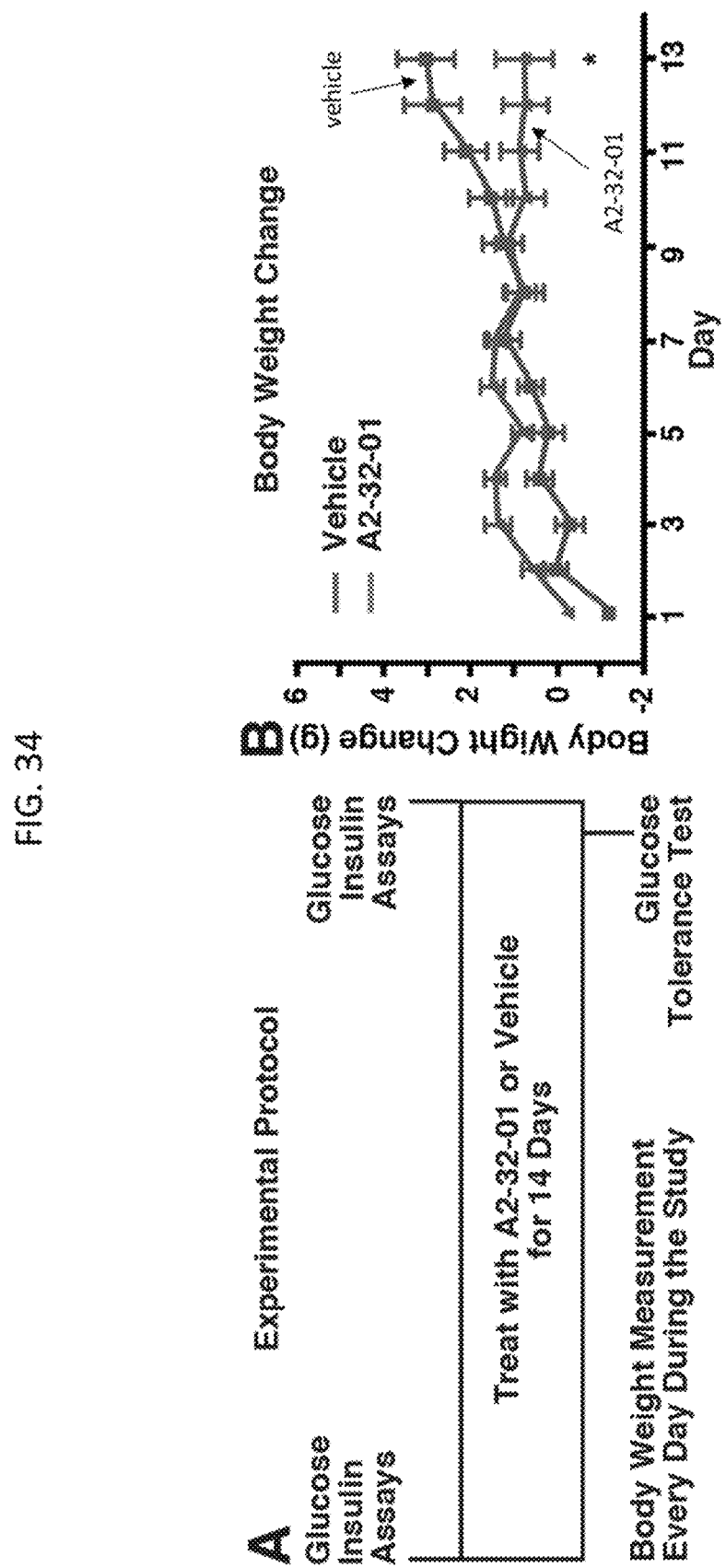
FIG. 34, Panel A, provides a schematic showing an experimental scheme of A2-32-01 treatment and metabolic assays in db/db mice.
Figure 35:
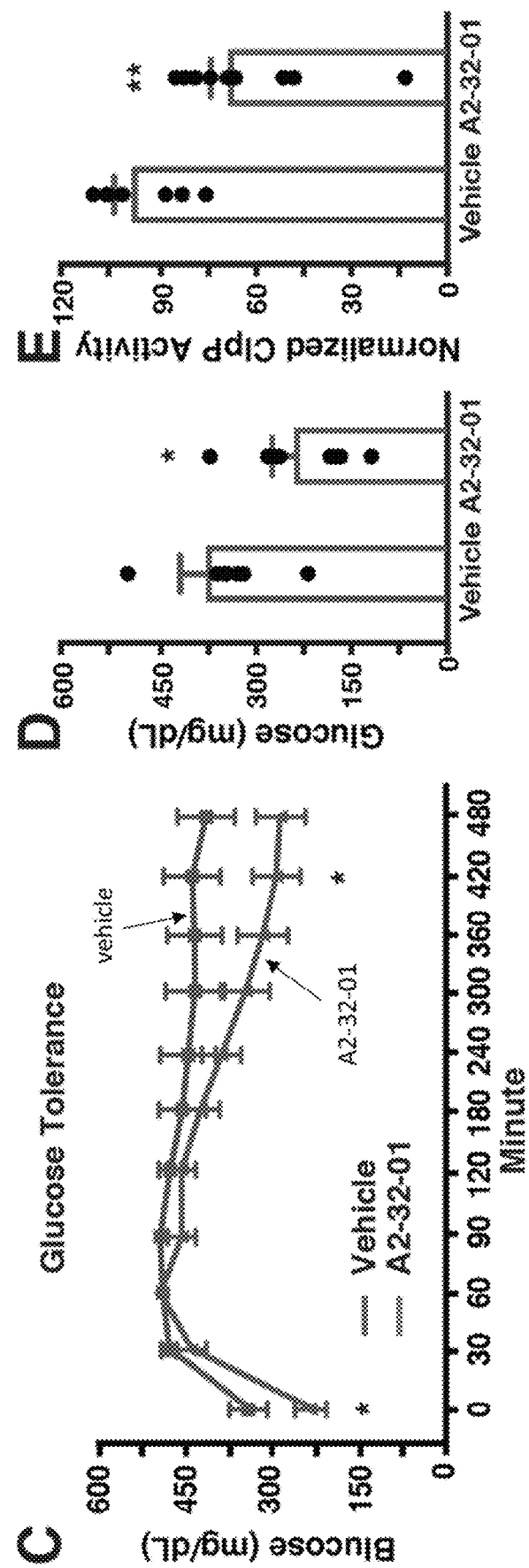
FIG. 35 provides, Panel C, provides a graph showing results of a glucose tolerance test showing increased insulin sensitivity in db/db mice treated with A2-32-01 compared with those treated with vehicle (n=7 for vehicle group, n=9 for A2-32-01 group).
Figure 36:
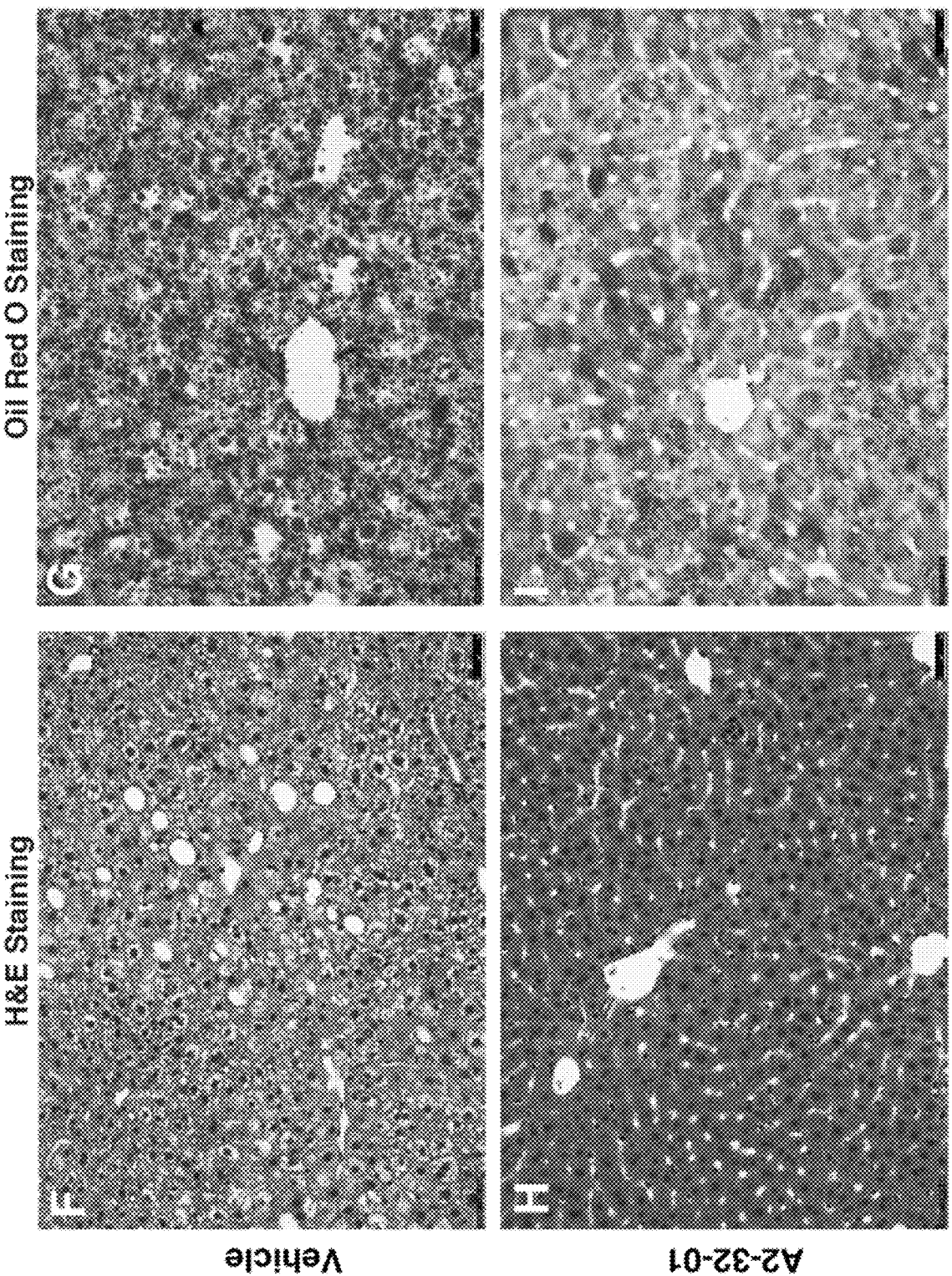
FIG. 36, panels F-I, provide representative H&E (Panels F, H) and oil red staining (Panels G, I) of liver sections from vehicle or A2-32-01 treated db/db mice. The micrographs showed that A2-32-01 treatment lowered the lipid accumulation in liver cells and restored normal morphology of liver cells in db/db mice, as compared to vehicle-treated db/db mice.

The following in-vivo analysis of db/db mice (a model of obesity, diabetes, and dyslipidemia—see, e.g., Kobayashi et al. *Metabolism*. 2000 January; 49(1):22-31.) was conducted according to the experimental scheme set forth in FIG. 34, panel A. As shown in FIG. 34, panel B, the A2-32-01-treated db/db mice had significantly decreased body weight compared to vehicle-treated db/db mice at the end of the treatment. In addition, glucose tolerance tests showed increased insulin sensitivity in db/db mice treated with A2-32-01 compared with those treated with vehicle (FIG. 35, panel C). Fasting blood glucose levels in db/db mice treated with A2-32-01 were significantly lower than those treated with vehicle as shown in FIG. 35, panel D. ClpP activity was lower in liver mitochondria lysates from db/db mice treated with A2-32-01 compared to those treated with vehicle as shown in FIG. 35, panel E. FIG. 36, panels F-I, show liver morphology from vehicle or A2-32-01-treated db/db mice, indicating that A2-32-01 treatment lowered the lipid accumulation in liver cells and restored normal morphology of liver cells in db/db mice, as compared to vehicle-treated db/db mice. Overall, these data demonstrate that treatment with ClpP inhibitor A2-32-01 in db/db mice significantly lowers body weight, increases insulin sensitivity, and restores normal liver morphology.

What is claimed is:

1. A method of identifying a candidate agent for treating obesity, liver disease, and/or diabetes, the method comprising:
   (a) obtaining an expression level and/or activity level of ClpP in a sample of mammalian cells derived from a subject to obtain a reference value;
   (b) contacting a sample of cells from said subject of (a) with a test agent;
   (c) measuring an expression level and/or activity level of ClpP in the sample of cells of (b) following the contacting;
   (d) determining that the test agent caused a decrease in the expression level and/or activity level of ClpP in the sample of cells of (b) as compared to the reference value of (a); and
   (e) administering to said subject a composition comprising the test agent, wherein the test agent is an inhibitor of ClpP, wherein the test agent is a β-Lactone.

2. The method according to claim 1, wherein the mammalian cell is a mouse cell.

3. The method according to claim 1, wherein the mammalian cell is a human cell.

4. The method according to claim 1, wherein the mammalian cell is in vitro.

5. The method according to claim 1, wherein the mammalian cell is ex vivo.

6. The method according to claim 1, wherein the mammalian cell is in vivo.

7. The method according to claim 1, wherein the mammalian cell is a hepatocyte.

8. The method according to claim 1, further comprising, after administering the identified candidate agent to the individual, measuring one or more features of the individual selected from: insulin sensitivity, blood glucose level, glucose tolerance, body fat mass, an amount of fat tissue, an amount of white adipose tissue; percent fat mass, body weight, visceral adipose adipocyte size, plasma leptin level, growth hormone level, basal energy expenditure, a level of phosphorylated AKT (p-AKT) in muscles and/or fibroblasts, percent lean mass, mitochondrial number in hepatocytes, mitochondrial mass in hepatocytes, mitochondrial morphology in hepatocytes, fibroblast respiratory capacity, fibroblast maximal oxygen consumption rate (OCR), and fibroblast resistance to $H_2O_2$-induced cytotoxicity.

9. The method according to claim 1, comprising measuring an expression level of ClpP, wherein the expression level is an RNA expression level and the measuring comprises the use of quantitative RT-PCR, a microarray, or RNA sequencing.

10. The method according to claim 1, comprising measuring an expression level of ClpP, wherein the expression level is a protein expression level and the measuring comprises detecting ClpP protein using an anti-ClpP antibody, mass spectrometry, and/or an enzymelinked immunosorbent assay (ELISA) assay.

11. The method of claim 1, wherein the expression level and/or activity level is reduced by 10% or more compared to the reference value.

* * * * *

UNITED STATES PATENT AND TRADEMARK OFFICE
CERTIFICATE OF CORRECTION

PATENT NO. : 11,376,242 B2
APPLICATION NO. : 16/129296
DATED : July 5, 2022
INVENTOR(S) : Huang et al.

It is certified that error appears in the above-identified patent and that said Letters Patent is hereby corrected as shown below:

On the Title Page

On page 2, in Column 1, item (56) under "Other Publications", Line 8, delete "CIpP:" and insert --ClpP:-- therefor On page 2, in Column 2, item (56) under "Other Publications", Line 61, delete "CipP," and insert --ClpP,-- therefor On page 2, in Column 2, item (56) under "Other Publications", Line 62, delete "leuekmia"," and insert --leukemia",-- therefor In the Claims In Column 50, Line 15, in Claim 8, delete "tissue;" and insert --tissue,-- therefor In Column 50, Line 34, in Claim 10, delete "enzymelinked" and insert --enzyme-linked-- therefor Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 7

<210> SEQ ID NO 1
<211> LENGTH: 277
<212> TYPE: PRT
<213> ORGANISM: Homo Sapiens

<400> SEQUENCE: 1

Met Trp Pro Gly Ile Leu Val Gly Gly Ala Arg Val Ala Ser Cys Arg
1               5                   10                  15

Tyr Pro Ala Leu Gly Pro Arg Leu Ala Ala His Phe Pro Ala Gln Arg
            20                  25                  30
```

Pro Pro Gln Arg Thr Leu Gln Asn Gly Leu Ala Leu Gln Arg Cys Leu
        35                  40                  45

His Ala Thr Ala Thr Arg Ala Leu Pro Leu Ile Pro Ile Val Val Glu
 50                  55                  60

Gln Thr Gly Arg Gly Glu Arg Ala Tyr Asp Ile Tyr Ser Arg Leu Leu
 65                  70                  75                  80

Arg Glu Arg Ile Val Cys Val Met Gly Pro Ile Asp Asp Ser Val Ala
                 85                  90                  95

Ser Leu Val Ile Ala Gln Leu Leu Phe Leu Gln Ser Glu Ser Asn Lys
            100                 105                 110

Lys Pro Ile His Met Tyr Ile Asn Ser Pro Gly Gly Val Val Thr Ala
            115                 120                 125

Gly Leu Ala Ile Tyr Asp Thr Met Gln Tyr Ile Leu Asn Pro Ile Cys
130                 135                 140

Thr Trp Cys Val Gly Gln Ala Ala Ser Met Gly Ser Leu Leu Leu Ala
145                 150                 155                 160

Ala Gly Thr Pro Gly Met Arg His Ser Leu Pro Asn Ser Arg Ile Met
                165                 170                 175

Ile His Gln Pro Ser Gly Gly Ala Arg Gly Gln Ala Thr Asp Ile Ala
            180                 185                 190

Ile Gln Ala Glu Glu Ile Met Lys Leu Lys Gln Leu Tyr Asn Ile
            195                 200                 205

Tyr Ala Lys His Thr Lys Gln Ser Leu Gln Val Ile Glu Ser Ala Met
        210                 215                 220

Glu Arg Asp Arg Tyr Met Ser Pro Met Glu Ala Gln Glu Phe Gly Ile
225                 230                 235                 240

Leu Asp Lys Val Leu Val His Pro Pro Gln Asp Gly Glu Asp Glu Pro
                245                 250                 255

Thr Leu Val Gln Lys Glu Pro Val Glu Ala Ala Pro Ala Ala Glu Pro
            260                 265                 270

Val Pro Ala Ser Thr
            275

<210> SEQ ID NO 2
<211> LENGTH: 272
<212> TYPE: PRT
<213> ORGANISM: Mus musculus

<400> SEQUENCE: 2

Met Trp Pro Arg Val Leu Leu Gly Glu Ala Arg Val Ala Val Asp Gly
 1               5                  10                  15

Cys Arg Ala Leu Leu Ser Arg Leu Ala Val His Phe Ser Pro Pro Trp
                20                  25                  30

Thr Ala Val Ser Cys Ser Pro Leu Arg Arg Ser Leu His Gly Thr Ala
            35                  40                  45

Thr Arg Ala Phe Pro Leu Ile Pro Ile Val Val Glu Gln Thr Gly Arg
 50                  55                  60

Gly Glu Arg Ala Tyr Asp Ile Tyr Ser Arg Leu Leu Arg Glu Arg Ile
65                  70                  75                  80

Val Cys Val Met Gly Pro Ile Asp Asp Ser Val Ala Ser Leu Val Ile
                85                  90                  95

Ala Gln Leu Leu Phe Leu Gln Ser Glu Ser Asn Lys Lys Pro Ile His
            100                 105                 110

Met Tyr Ile Asn Ser Pro Gly Gly Val Val Thr Ala Gly Leu Ala Ile
            115                 120                 125

Tyr Asp Thr Met Gln Tyr Ile Leu Asn Pro Ile Cys Thr Trp Cys Val
            130                 135                 140

Gly Gln Ala Ala Ser Met Gly Ser Leu Leu Ala Ala Gly Ser Pro
145                 150                 155                 160

Gly Met Arg His Ser Leu Pro Asn Ser Arg Ile Met Ile His Gln Pro
                165                 170                 175

Ser Gly Gly Ala Arg Gly Gln Ala Thr Asp Ile Ala Ile Gln Ala Glu
            180                 185                 190

Glu Ile Met Lys Leu Lys Lys Gln Leu Tyr Asn Ile Tyr Ala Lys His
            195                 200                 205

Thr Lys Gln Ser Leu Gln Val Ile Glu Ser Ala Met Glu Arg Asp Arg
210                 215                 220

Tyr Met Ser Pro Met Glu Ala Gln Glu Phe Gly Ile Leu Asp Lys Val
225                 230                 235                 240

Leu Val His Pro Pro Gln Asp Gly Glu Asp Glu Pro Glu Leu Val Gln
                245                 250                 255

Lys Glu Thr Ala Thr Ala Pro Thr Asp Pro Pro Ala Pro Thr Ser Thr
            260                 265                 270

<210> SEQ ID NO 3
<211> LENGTH: 1194
<212> TYPE: DNA
<213> ORGANISM: Homo Sapiens

<400> SEQUENCE: 3
ccttaatggc gcccgcccag actcctggaa gtgagcggcc tagcgagcga gctcccaggc      60
gcaaagcacg ccggaagctg tagttccgcc atcgacgga agccgaccgg ggcgtgcgga     120
gggatgtggc ccggaatatt ggtaggggggg ccccgggtgg cgtcatgcag gtaccccgcg    180
ctggggcctc gcctcgccgc tcactttcca gcgcagcggc cgccgcagcg gacactccag    240
aacggcctgg ccctgcagcg gtgcctgcac gcgacggcga cccgggctct cccgctcatt    300
cccatcgtgg tggagcagac gggtcgcggc gagcgcgcct atgacatcta ctcgcggctg    360
ctgcgggagc gcatcgtgtg cgtcatgggc ccgatcgatg acagcgttgc cagccttgtt    420
atcgcacagc tcctcttcct gcaatccgag agcaacaaga agcccatcca catgtacatc    480
aacagccctg gtggtgtggt gaccgcgggc ctggccatct acgacacgat gcagtacatc    540
ctcaacccga tctgcacctg gtgcgtgggc caggccgcca gcatgggctc cctgcttctc    600
gccgccggca ccccaggcat gcgccactcg ctccccaact cccgtatcat gatccaccag    660
cccctcagga gcgcccgggg ccaagccaca gacattgcca tccaggcaga ggagatcatg    720
aagctcaaga agcagctcta taacatctac gccaagcaca ccaaacagag cctgcaggtg    780
atcgagtccg ccatggagag ggaccgctac atgagcccca tggaggccca ggagtttggc    840
atcttagaca aggttctggt ccaccctccc caggacggtg aggatgagcc acgctggtg     900 cagaaggagc tgtagaagc agcgccggca gcagaacctg tcccagctag cacctgagag    960
ctgggcctcc tctccagaat catgtggagg ggccagaggc ctgccagacc cccagctggg   1020
ccctgctcac cccttgttgc tgggcttgga ggggcctctt gaggaacttt taatttgcag   1080
gggtgcccgc tatggacggg gcattccagc tgagacactg tgattttaaa ttaaatcttt   1140
gtggtctttg caaaaaaaaa aaaaaaaaaa aaaaaaaaaa aaaa                     1194

-continued

```
<210> SEQ ID NO 4
<211> LENGTH: 1207
<212> TYPE: DNA
<213> ORGANISM: Mus musculus

<400> SEQUENCE: 4
agtgactccc gcaaagcacg ccgggtgttg tagttccgga agccaagccg gagtgcgcgt      60
cgtcatgtgg cccagagtgc tgctggggga ggcccgggtg gctgtggacg gatgtcgcgc     120
tctgttgtct cgccttgccg tgcatttctc cccgccatgg actgctgtga gctgctcacc     180
cctgcggagg agcctgcatg gaactgcgac gcgagctttc ccgctcatcc ccatagtggt     240
ggagcagacg gtcgaggcg agcgcgctta tgacatatac tcgaggctgt tgcgggaacg      300
catcgtgtgc gtcatgggcc cgattgacga cagtgtggcc agtctggtca ttgcccagct     360
gttgttctta cagtctgaaa gcaacaagaa gcccattcat atgtatatca acagcccagg     420
tggtgtggta actgcgggcc tggccatcta cgacacaatg cagtacatcc tgaaccccat     480
ctgcacgtgg tgtgttggac aggctgccag catgggctcc ctgctcctcg ctgctggcag     540
cccgggcatg cgccattcac tgcccaattc agaatcatg atccaccagc cctctggagg      600
agccaggggc caagccacag acatcgccat ccaggcagag gaaatcatga agctgaaaaa     660
gcagctatac aacatctacg ccaaacacac caagcagagc ctacaggtga tcgagtcagc     720
aatggagagg gaccgctaca tgagccccat ggaggcccaa gagtttggca tcttggacaa     780
ggtcttggtc cacccacctc aggacgggga ggatgagcca gaactggtac agaaggagac     840
tgccacagcg ccgacggatc ctcctgcccc gacaagcacc taaggagtgg agaccagact     900
gaaacttcct ctgctgggcc caagaacaac ccctagagga gatgtggatt gaggttgccc     960
tcagagcagg gcagactgcc tgagacactg tgatttaaat taaatctttg tagtctttgt    1020
cccatgtctg aagcaccttc cattacttct ccaagacagc aggcctcctt caccttgaca    1080
aaccacttca gtaagcaaac cctggctctc ctggaactaa accaatctag cctcagactc    1140
aggtacccac ctgcctcacc tcctgagtgc taggattaaa ggtgtacacc accacacctg    1200
acttcaa                                                              1207

<210> SEQ ID NO 5
<211> LENGTH: 21
<212> TYPE: DNA
<213> ORGANISM: Artificial sequence
<220> FEATURE:
<223> OTHER INFORMATION: Synthetic primer

<400> SEQUENCE: 5
gcccatccac atgtacatca a                                                21

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
cacgatgcag tacatcctca a                                                21

<210> SEQ ID NO 7
<211> LENGTH: 21
<212> TYPE: DNA
<213> ORGANISM: Artificial sequence
```

```
<220> FEATURE:
<223> OTHER INFORMATION: Synthetic primer

<400> SEQUENCE: 7
gctcaagaag cagctctata a                                              21
```